US007585497B2

(12) United States Patent
Oh et al.

(10) Patent No.: US 7,585,497 B2
(45) Date of Patent: Sep. 8, 2009

(54) INDUCTION OF APOPTOSIS AND CELL GROWTH INHIBITION BY PROTEIN 4.33

(75) Inventors: Youngman Oh, Richmond, VA (US); Ron Rosenfeld, Palo Alto, CA (US); Angela Renae Ingermann, Beaverton, OR (US)

(73) Assignee: Oregon Health & Science University, Portland, OR (US)

( * ) Notice: Subject to any disclaimer, the term of this patent is extended or adjusted under 35 U.S.C. 154(b) by 31 days.

(21) Appl. No.: 10/276,491

(22) PCT Filed: May 17, 2001

(86) PCT No.: PCT/US01/16437

§ 371 (c)(1), (2), (4) Date: Feb. 20, 2003

(87) PCT Pub. No.: WO01/87238

PCT Pub. Date: Nov. 22, 2001

(65) Prior Publication Data

US 2004/0072285 A1 Apr. 15, 2004

Related U.S. Application Data

(60) Provisional application No. 60/204,949, filed on May 17, 2000.

(51) Int. Cl.
*A01N 43/04* (2006.01)
*A01N 63/00* (2006.01)
*A61K 31/715* (2006.01)

(52) U.S. Cl. ........................................ 424/93.2; 514/44

(58) Field of Classification Search .................. 436/64, 436/813; 514/44; 424/93.2
See application file for complete search history.

(56) References Cited

U.S. PATENT DOCUMENTS

| 4,376,110 A | 3/1983 | David et al. |
| 4,745,051 A | 5/1988 | Smith et al. |
| 4,946,778 A | 8/1990 | Ladner et al. |
| 5,399,346 A | 3/1995 | Anderson et al. |
| 5,460,959 A | 10/1995 | Mulligan et al. |
| 5,840,673 A * | 11/1998 | Buckbinder et al. ......... 510/392 |

FOREIGN PATENT DOCUMENTS

| WO | WO 88/04300 | 6/1988 |
| WO | WO 88/09810 | 12/1988 |
| WO | WO 89/10134 | 11/1989 |
| WO | WO 90/11364 | 10/1990 |
| WO | WO 99/61471 A2 * | 9/1999 |
| WO | WO99/61471 | 12/1999 |

OTHER PUBLICATIONS

Freshney, Culture of Animal Cells, A Manual of Basic Technique, Alan R. Liss, Inc., 1983, New York, pp. 3-4.*
Dermer, Bio/Technology, 1994, 12:320.*
MSNBC News Services, "Mixed results on new cancer drug", Nov. 9, 2000.*
Gura, Science, 1997, 278(7):1041-1042.*
Jain, Scientific American, 1994, pp. 58-65).*
Crystal, R.G., Science, 270: 404-401, 1995.*
Izquierdo, M. Cancer Gene Therapy, 12: 217-227, 2005.*
Shankar, P. et al. JAMA, 293(11): 1367-73, 2005.*
Heidenreich, O., Current Pharmaceutical Biotechnology, 5: 349-354, 2004.*
U.S. Appl. No. 60/204,949, filed May 17, 2000, Youngman et al.
Baxter et al., "Modulation of Human IGF Binding Protein-3 Activity by Structural Modification," Progress in Growth Factor Research, 1995, pp. 215-222, vol. 6.
Been et al., "One Binding Site Determines Sequence Specificity of Tetrahymena Pre-rRNA Self-Splicing, Trans-Splicing, and RNA Enzyme Activity," Cell, 1986, pp. 207-216, vol. 47.
Benoist et al., "In vivo sequence requirements of the SV40 early promoter region," Nature, 1981, pp. 304-310, vol. 290.
Bird, "Single-Chain Antigen-Binding Proteins," Science, 1988, pp. 423-426, vol. 242.
Bitter et al, "Expression and Secretion Vectors for Yeast," Methods in Enzymology, 1987, pp. 516-544, vol. 153.
Brinster et al., "Regulation of metallothionein-thymidine kinase fusion plasmids injected into mouse eggs," Nature, 1982, pp. 39-42, vol. 296.
Colbère-Garapin et al., "A New Dominant Hybrid Selective Marker for Higher Eukaryotic Cells," The Journal of Molecular Biology, 1981, pp. 1-14, vol. 150.
Cole et al., "'The EBV-Hybridoma Technique and Its Application to Human Lung Cancer," Monoclonal Antibodies and Cancer Therapy," Alan R. Liss, Inc., 1985, pp. 77-96.

(Continued)

Primary Examiner—Michael C. Wilson
(74) Attorney, Agent, or Firm—Barry L. Davison; Davis Wright Temaine LLP

(57) ABSTRACT

There is disclosed an isolated cDNA sequence (SEQ ID NO:1) encoding a P4.33 polypeptide and comprising a coding region (SEQ ID NO:2) of the sequence described in SEQ ID NO:1, or a sequence having at least 90% homology with the coding region of SEQ ID NO:1. The P4.33 polypeptide functions as a specific cell-surface receptor for IGFBP-3, and undergoes nuclear translocation in combination with IGFBP-3. IGFBP-3 and P4.33 (IGFBP-3R) cooperatively suppress DNA synthesis and cell growth, and induce caspase activation and apoptosis in cancer cells, indicating that P4.33 is an important mediator of IGF-independent growth inhibitory actions of IGFBP-3. The P4.33:IGFBP-3 system of the present invention can be used, inter alia, in screening and diagnostic assays, and for therapeutic methods for cancer treatment and tumor suppression.

12 Claims, 30 Drawing Sheets

OTHER PUBLICATIONS

Cote et al., "Generation of human monoclonal antibodies reactive with cellular antigens," The Proceedings of the National Academy of Sciences, 1983, pp. 2026-2030, vol. 80.
Cubbage et al., "Insulin-like Growth Factor Binding Protein-3," The Journal of Biological Chemistry, 1990, pp. 12642-12649, vol. 265.
Database Genbank, Accession No. AAZ24419, DE19818619-A1 (Metagen Ges Genomforschung MBH), Oct. 28, 1999.
Database Genbank, Accession No. AAY57877, WO 99/61471-A2 (Incyte Pharm Inc.), Dec. 02, 1999.
Database Genbank, Accession No. AAY66189, DE19818619-A1 (Metagen Ges Genomforschung MBH), Oct. 28, 1999.
Gautier et al., "α-DNA IV: α-anomeric and β-anomeric tetrathymidylates covalently linked to intercalating oxazolopyridocarbazole. Synthesis, physicochemical properties and poly (rA) binding," Nucleic Acids Research, 1987, pp. 6625-6641, vol. 15.
Gavrieli et al., "Identification of Programmed Cell Death In Situ via Specific Labeling of Nuclear DNA Fragmentation," The Journal of Cell Biology, 1992, p. 493-501, vol. 119.
Greenspan et al., "Idiotypes: structure and immunogenicity," The FASEB Journal, 1993, pp. 437-444, vol. 75.
Haseloff et al., "Simple RNA enzymes with new and highly specific endoribonuclease activities," Nature, 1988, pp. 585-591, vol. 334.
Hélène, "The anti-gene strategy: control of gene expression by triplex-forming-oligonucleotides," Anti-Cancer Drug Design, 1991, pp. 569-584, vol. 6.
Hélène et al., "Control of Gene Expression by Triple Helix-Forming Oligonucleotides," The Annals of the New York Academy of Sciences, 1992, pp. 27-36, vol. 660.
Hengartner, "The biochemistry of apoptosis," Nature, 2000, pp. 770-776, vol. 407.
Hoeck et al., "Identification of the Major Sites of Phosphorylation in IGF Binding Protein-3," Journal of Cellular Biochemistry, 1994, pp. 262-273, vol. 56.
Houghten et al., "Generation and use of synthetic peptide combinatorial libraries for basic research and drug discovery," Nature, 1991, pp. 84-86, vol. 354.
Huse et al., "Generation of a Large Combinatorial Library of the Immunoglobulin Repertoire in Phage Lambda," Science, 1989, pp. 1275-1281, vol. 246.
Huston et al., "Protein engineering of antibody binding sites: recovery of specific activity in an anti-digoxin single-chain Fv analogue produced in *Escherichia coli*," The Proceedings of the National Academy of Sciences, 1988, pp. 5879-5883, vol. 85.
Inoue et al., "Sequence-dependent hydrolysis of RNA using modified oligonucleotide splints and RNase H," FEBS Letters, 1987, pp. 327-330, vol. 215.
Inoue et al., "Synthesis and hybridization studies on two complementary nona(2'-O-methyl)ribonucleotides," Nucleic Acids Research, 1987, pp. 6131-6148, vol. 15.
Inouye et al., "Up-promoter mutations in the Ipp gene of *Escherichia coli*," Nucleic Acids Research, 1985, pp. 3101-3110, vol. 13.
Janknecht et al., "Rapid and efficient purification of native histidine-tagged protein expressed by recombinant vaccinia virus," The Proceedings of the National Academy of Sciences, 1991, pp. 8972-8976, vol. 88.
Köhler et al., "Continuous cultures of fused cells secreting antibody of predefined specificity," Nature, 1975, pp. 495-497, vol. 256.
Kozbor et al., "The production of monoclonal antibodies from human lymphocytes," Immunology Today, 1983, pp. 72-79, vol. 4.
Lam et al., "A new type of synthetic peptide library for identifying ligand-binding activity," Nature, 1991, pp. 82-84, vol. 354.
Lemaitre et al., "Specific antiviral activity of a poly(L-lysine)-conjugated oligodeoxyribonucleotide sequence complementary to vesicular stomatitis virus N protein mRNA initiation site," The Proceedings of the National Academy of Sciences, 1987, pp. 648-652, vol. 84.
Letsinger et al., "Cholesteryl-conjugated oligonucleotides: Synthesis, properties, and activity as inhibitors of replication of human immunodeficiency virus in cell culture," The Proceedings of the National Academy of Sciences, 1989, pp. 6553-6556, vol. 86.

Logan et al., "Adenovirus tripartite leader sequence enhances translation of mRNAs late after infection," The Proceedings of the National Academy of Sciences, 1984, pp. 3655-3659, vol. 81.
Lowy et al., "Isolation of Transforming DNA: Cloning the Hamster aprt Gene," Cell, 1980, pp. 817-823, vol. 22.
Maher, "DNA Triple-Helix Formation: An Approach to Artificial Gene Repressors?," BioEssays, 1992, pp. 807-815, vol. 14.
Morrison et al., "Chimeric Human Antibody Molecules: Mouse Antigen-Binding Domains with Human Constant Region Domains," The Proceedings of the National Academy of Sciences, 1984, pp. 6851-6855, vol. 81.
Mulligan et al., "Selection for animals cells that express the *Escherichia coli* gene coding for xanthine-guanine phosphoribosyltransferase," The Proceedings of the National Academy of Sciences, 1981, pp. 2072-2076, vol. 78.
Neuberger et al., "Recombinant antibodies possessing novel effector functions," Nature, 1984, pp. 604-608, vol. 312.
Nisonoff, "Idiotypes: Concepts and Applications," Journal of Immunology, 1991, pp. 2429-2438, vol. 147.
O'Hare et al., "Transformation of mouse fibroblasts to methotrexate resistance by a recombinant plasmid expressing a prokaryotic dihydrofolate reductase," The Proceedings of the National Academy of Sciences, 1981, pp. 1527-1531, vol. 78.
Rüther et al., "Easy identification of cDNA clones," The EMBO Journal, 1983, pp. 1791-1794, vol. 2.
Santerre et al., "Expression of prokaryotic genes for hygromycin B and G418 resistance as dominant-selectino markers in mouse L cells," Gene, 1984, pp. 147-156, vol. 30.
Sarin et al., "Inhibition of acquired immunodeficiency syndrome virus by oligodeoxynucleoside methylphosphonates," The Proceedings of the National Academy of Sciences, 1988, pp. 7448-7451, vol. 85.
Sarver et al., "Ribozymes as Potential Anti-HIV-1 Therapeutic Agents," Science, 1990, pp. 1222-1225, vol. 247.
Smith et al., "Molecular Engineering of the Autographa californica Nuclear Polyhedrosis Virus Genome: Deletion Mutations Within the Polyhedrin Gene," Journal of Virology, 1983, pp. 584-593, vol. 46.
Smithies et al., "Insertion of DNA sequences into the human chromosomal β-globin locus by homologous recombination," Nature, 1985, pp. 230-234, vol. 317.
Songyang et al., "SH2 Domains Recognize Specific Phosphopeptide Sequences," Cell, 1993, pp. 767-778, vol. 72.
Stein et al., "Physicochemical properties of phosphorothioate oligodeoxynucleotides," Nucleic Acids Research, 1988, pp. 3209-3221, vol. 16.
Szybalska et al., "Genetics of Human Cell Lines, IV. DNA-Mediated Heritable Transformation of a Biochemical Trait," The Proceedings of the National Academy of Sciences, 1962, pp. 2026-2034, vol. 48.
Takeda et al., "Construction of chimaeric processed immunoglobulin genes containing mouse variable and human constant region sequences," Nature, 1985, pp. 452-454, vol. 314.
Thomas et al., "Site-Directed Mutagenesis by Gene Targeting in Mouse Embryo-Derived Stem Cells," Cell 1987, pp. 503-512, vol. 51.
Thompson et al., "Germ Line Transmission and Expression of a Corrected HPRT Gene Produced by Gene Targeting in Embryonic Stem Cells," Cell, 1989, pp. 313-321, vol. 56.
Van Der Krol et al. "Modulation of Eukaryotic Gene Expression by Complementary RNA or DNA Sequences," BioTechniques, 1988, pp. 958-976, vol. 6.
Van Heeke et al., "Expression of Human Asparagine Synthetase in *Escherichia coli*," The Journal of Biological Chemistry, 1989, pp. 5503-5509, vol. 264.
Wagner, "Gene inhibition using antisense oligodeoxynucleotides," Nature, 1994, pp. 333-335, vol. 372.
Wagner et al., "Nucleotide sequence of the thymidine kinase gene of herpes simplex virus type 1," The Proceedings of the National Academy of Sciences, 1981, pp. 1441-1445, vol. 78.
Ward et al., "Binding activities of a repertoire of single immunoglobulin variable domains secreted from *Escherichia coli*," Nature, 1989, pp. 544-546, vol. 341.
Wigler et al., "Transfer of Purified Herpes Virus Thymidine Kinase Gene to Cultured Mouse Cells," Cell, 1977, pp. 223-232, vol. 11.

Wigler et al., "Transformation of mammalian cells with an amplifiable dominant-acting gene," The Proceedings of the National Academy of Sciences, 1980, pp. 3567-3570, vol. 77.

Yamamoto et al., "Identification of a Functional Promoter in the Long Terminal Repeat of Rous Sarcoma Virus," Cell, 1980, pp. 787-797, vol. 22.

Zaug et al., "The Intervening Sequence RNA of Tetrahymena Is an Enzyme," Science, 1986, pp. 470-475, vol. 231.

Zaug et al., "A Labile Phosphodiester Bond at the Ligation Junction in a Circular Intervening Sequence RNA," Science, 1984, pp. 574-578, vol. 224.

Zaug et al., "The Tetrahymena ribozyme acts like an RNA restriction endonuclease," Nature, 1986, pp. 429-433, vol. 324.

Zon, "Oligonucleotide Analogues as Potential Chemotherapeutic Agents," Pharmaceutical Research, 1988, pp. 539-549, vol. 5.

* cited by examiner

| C |

```
GGGCTCTCCCCGGAGGCTCAGCCCCCTCTGCTCCCCATGGGCAACTGCCAGGCAGGGCACAACCTGCACCTGTGTCTGGC    80
CCACCACCCACCTCTGGTCTGTGCCACTTTGATCCTGCTGCTCCTTGGCCTCTCTGGCCTGGGCCTTGGCAGCTTCCTCC   160
TCACCCACAGGACTGGCCTGCGCAGCCCTGACATCCCCCAGGACTGGGTCTCTTTTTTGAGATCTTTTGGCCAGCTGACC   240
CTGTGTCCCAGGAATGGGACAGTCACAGGGAAGTGGCGAGGGTCTCACGTCGTGGGCTTGCTGACCACCTTGAACTTCGG   320
AGACGGTCCAGACAGGAACAAGACCCGGACATTCCAGGCCACAGTCCTGGGAAGTCAGATGGGATTGAAAGGATCTTCTG   400
CAGGACAACTGGTCCTTATCACAGCCAGGGTGACCACAGAAAGGACTGCAGGAACCTGCCTATATTTTAGTGCTGTTCCA   480
GGAATCCTACCCTCCAGCCAGCCACCCATATCCTGCTCAGAGGAGGGGGCTGGAAATGCCACCCTGAGCCCTAGAATGGG   560
TGAGGAATGTGTTAGTGTCTGGAGCCATGAAGGCCTTGTGCTGACCAAGCTGCTCACCTCGGAGGAGCTGGCTCTGTGTG   640
GCTCCAGGCTGCTGGTCTTGGGCTCCTTCCTGCTTCTCTTCTGTGGCCTTCTCTGCTGTGTCACTGCTATGTGCTTCCAC   720
CCGCGCCGGGAGTCCCACTGGTCTAGAACCCGGCTCTGAGGGCACTGGCCTAGTTCCCGACTTGTTTCTCAGGTGTGAAT   800
CAACTTCTTGGGCCTTGGCTCTGAGTTGGAAAAGGTTTTAGAAAAAGTGAAGAGCTGGAATGTGGGGAAAATAAAAAGC    880
TTTTTTGCCCAAAAAAAAAAAAAAAAAAAAAAAAAA                                              915
```

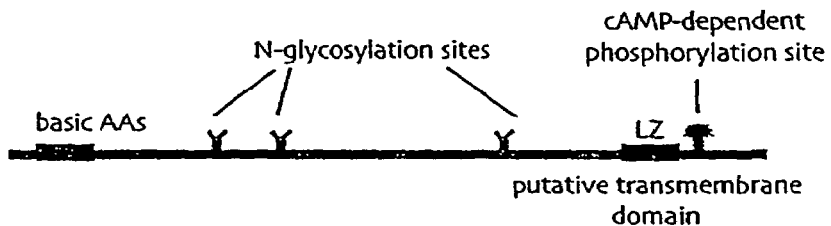

*Fig. 2C*

Transfection:

| | | | | | | |
|---|---|---|---|---|---|---|
| EGFP | + | + | – | – | – | – |
| EGFP::IGFBP-3R | – | – | + | + | + | + |
| IGFBP-3$^F$ | – | – | – | – | + | + |
| IP: αFLAG M2 | – | + | – | + | – | + |

(kDa)
53 –   ← EGFP::4-33
29 –   ← unfused EGFP

IP: αGFP  – + – + – +

(kDa)
53 –
29 –   ← IGFBP-3$^F$

A
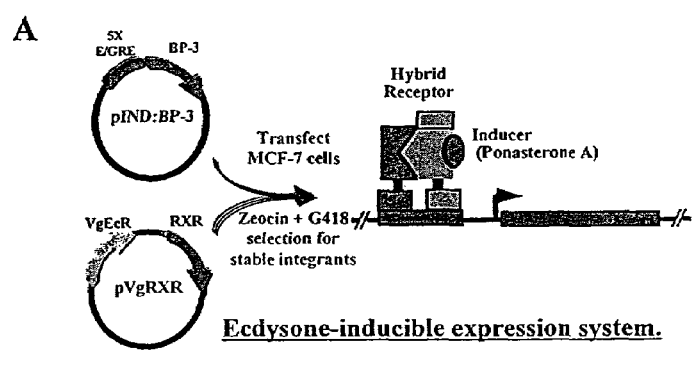
B
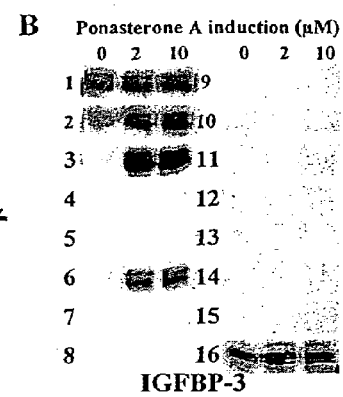
*Fig. 7B-1*
*Fig. 7B-2*

*Fig. 11*

| Cell Lines | A492 Reading (Arbitrary Unit) | | Growth Inhibition (% of Control) |
|---|---|---|---|
| | Control | +IGFBP-3R | |
| Hs578T | 1.86 ± 0.16 | 0.79 ± 0.13 | *42 ± 2.0 |
| MDA231 | 0.38 ± 0.18 | 0.08 ± 0.05 | *21 ± 4.0 |
| PC-3 | 0.62 ± 0.13 | 0.06 ± 0.06 | *10 ± 2.9 |
| H157 | 1.82 ± 0.38 | 0.53 ± 0.19 | *29 ± 3.0 |

*$p < 0.001$

Anti-proliferative Effect of the IGFBP-3R
after Co-expression of IGFBP-3 in MCF-7 Cells New Class of Cell Death Receptor: IGFBP-3 Receptor

SEQUENCE LISTING

<160> NUMBER OF SEQ ID NOS: 17

<210> SEQ ID NO 1
<211> LENGTH: 915
<212> TYPE: DNA
<213> ORGANISM: Homo sapiens
<220> FEATURE:
<221> NAME/KEY: CDS
<222> LOCATION: (37)..(759)
<223> OTHER INFORMATION: coding sequence

<400> SEQUENCE: 1

```
gggctctccc cggaggctca gcccccctctg ctcccc atg ggc aac tgc cag gca        54
                                         Met Gly Asn Cys Gln Ala
                                          1               5 ggg cac aac ctg cac ctg tgt ctg gcc cac cac cca cct ctg gtc tgt        102
Gly His Asn Leu His Leu Cys Leu Ala His His Pro Pro Leu Val Cys
             10                  15                  20 gcc act ttg atc ctg ctg ctc ctt ggc ctc tct ggc ctg ggc ctt ggc        150
Ala Thr Leu Ile Leu Leu Leu Leu Gly Leu Ser Gly Leu Gly Leu Gly
         25                  30                  35 agc ttc ctc ctc acc cac agg act ggc ctg cgc agc cct gac atc ccc        198
Ser Phe Leu Leu Thr His Arg Thr Gly Leu Arg Ser Pro Asp Ile Pro
     40                  45                  50 cag gac tgg gtc tct ttt ttg aga tct ttt ggc cag ctg acc ctg tgt        246
Gln Asp Trp Val Ser Phe Leu Arg Ser Phe Gly Gln Leu Thr Leu Cys
 55                  60                  65                  70 ccc agg aat ggg aca gtc aca ggg aag tgg cga ggg tct cac gtc gtg        294
Pro Arg Asn Gly Thr Val Thr Gly Lys Trp Arg Gly Ser His Val Val
                 75                  80                  85 ggc ttg ctg acc acc ttg aac ttc gga gac ggt cca gac agg aac aag        342
Gly Leu Leu Thr Thr Leu Asn Phe Gly Asp Gly Pro Asp Arg Asn Lys
             90                  95                 100 acc cgg aca ttc cag gcc aca gtc ctg gga agt cag atg gga ttg aaa        390
Thr Arg Thr Phe Gln Ala Thr Val Leu Gly Ser Gln Met Gly Leu Lys
        105                 110                 115 gga tct tct gca gga caa ctg gtc ctt atc aca gcc agg gtg acc aca        438
Gly Ser Ser Ala Gly Gln Leu Val Leu Ile Thr Ala Arg Val Thr Thr
    120                 125                 130 gaa agg act gca gga acc tgc cta tat ttt agt gct gtt cca gga atc        486
Glu Arg Thr Ala Gly Thr Cys Leu Tyr Phe Ser Ala Val Pro Gly Ile
135                 140                 145                 150 cta ccc tcc agc cag cca ccc ata tcc tgc tca gag gag ggg gct gga        534
Leu Pro Ser Ser Gln Pro Pro Ile Ser Cys Ser Glu Glu Gly Ala Gly
                155                 160                 165 aat gcc acc ctg agc cct aga atg ggt gag gaa tgt gtt agt gtc tgg        582
Asn Ala Thr Leu Ser Pro Arg Met Gly Glu Glu Cys Val Ser Val Trp
            170                 175                 180 agc cat gaa ggc ctt gtg ctg acc aag ctg ctc acc tcg gag gag ctg        630
Ser His Glu Gly Leu Val Leu Thr Lys Leu Leu Thr Ser Glu Glu Leu
        185                 190                 195 gct ctg tgt ggc tcc agg ctg ctg gtc ttg ggc tcc ttc ctg ctt ctc        678
Ala Leu Cys Gly Ser Arg Leu Leu Val Leu Gly Ser Phe Leu Leu Leu
    200                 205                 210 ttc tgt ggc ctt ctc tgc tgt gtc act gct atg tgc ttc cac ccg cgc        726
Phe Cys Gly Leu Leu Cys Cys Val Thr Ala Met Cys Phe His Pro Arg
215                 220                 225                 230 cgg gag tcc cac tgg tct aga acc cgg ctc tga gggcactggc ctagttcccg    779
Arg Glu Ser His Trp Ser Arg Thr Arg Leu
                235                 240
```

-continued

```
acttgtttct caggtgtgaa tcaacttctt gggccttggc tctgagttgg aaaaggtttt      839
agaaaaagtg aagagctgga atgtggggga aaataaaaag cttttttgcc caaaaaaaa       899 aaaaaaaaaa aaaaa                                                       915
```

<210> SEQ ID NO 2
<211> LENGTH: 240
<212> TYPE: PRT
<213> ORGANISM: Homo sapiens

<400> SEQUENCE: 2

```
Met Gly Asn Cys Gln Ala Gly His Asn Leu His Leu Cys Leu Ala His
1               5                   10                  15

His Pro Pro Leu Val Cys Ala Thr Leu Ile Leu Leu Leu Gly Leu
            20                  25                  30

Ser Gly Leu Gly Leu Gly Ser Phe Leu Leu Thr His Arg Thr Gly Leu
        35                  40                  45

Arg Ser Pro Asp Ile Pro Gln Asp Trp Val Ser Phe Leu Arg Ser Phe
    50                  55                  60

Gly Gln Leu Thr Leu Cys Pro Arg Asn Gly Thr Val Thr Gly Lys Trp
65                  70                  75                  80

Arg Gly Ser His Val Val Gly Leu Leu Thr Thr Leu Asn Phe Gly Asp
                85                  90                  95

Gly Pro Asp Arg Asn Lys Thr Arg Thr Phe Gln Ala Thr Val Leu Gly
            100                 105                 110

Ser Gln Met Gly Leu Lys Gly Ser Ser Ala Gly Gln Leu Val Leu Ile
        115                 120                 125

Thr Ala Arg Val Thr Thr Glu Arg Thr Ala Gly Thr Cys Leu Tyr Phe
    130                 135                 140

Ser Ala Val Pro Gly Ile Leu Pro Ser Ser Gln Pro Pro Ile Ser Cys
145                 150                 155                 160

Ser Glu Glu Gly Ala Gly Asn Ala Thr Leu Ser Pro Arg Met Gly Glu
                165                 170                 175

Glu Cys Val Ser Val Trp Ser His Glu Gly Leu Val Leu Thr Lys Leu
            180                 185                 190

Leu Thr Ser Glu Glu Leu Ala Leu Cys Gly Ser Arg Leu Leu Val Leu
        195                 200                 205

Gly Ser Phe Leu Leu Leu Phe Cys Gly Leu Leu Cys Cys Val Thr Ala
    210                 215                 220

Met Cys Phe His Pro Arg Arg Glu Ser His Trp Ser Arg Thr Arg Leu
225                 230                 235                 240
```

<210> SEQ ID NO 3
<211> LENGTH: 20
<212> TYPE: DNA
<213> ORGANISM: artificial sequence
<220> FEATURE:
<223> OTHER INFORMATION: antisense oligonucleotide

<400> SEQUENCE: 3

```
ctcagccccc tctgctcccc                                                   20
```

<210> SEQ ID NO 4
<211> LENGTH: 21
<212> TYPE: DNA
<213> ORGANISM: artificial sequence
<220> FEATURE:
<223> OTHER INFORMATION: antisense oligonucleotide -continued

```
<400> SEQUENCE: 4
cctctgctcc ccatgggcaa c                                          21

<210> SEQ ID NO 5
<211> LENGTH: 17
<212> TYPE: DNA
<213> ORGANISM: artificial sequence
<220> FEATURE:
<223> OTHER INFORMATION: antisense oligonucleotide

<400> SEQUENCE: 5
tgctccccat gggcaac                                               17

<210> SEQ ID NO 6
<211> LENGTH: 18
<212> TYPE: DNA
<213> ORGANISM: artificial sequence
<220> FEATURE:
<223> OTHER INFORMATION: antisense oligonucleotide

<400> SEQUENCE: 6
cccatgggca actgccag                                              18

<210> SEQ ID NO 7
<211> LENGTH: 20
<212> TYPE: DNA
<213> ORGANISM: artificial sequence
<220> FEATURE:
<223> OTHER INFORMATION: antisense oligonucleotide

<400> SEQUENCE: 7
ccccatgggc aactgccagg                                            20

<210> SEQ ID NO 8
<211> LENGTH: 19
<212> TYPE: DNA
<213> ORGANISM: artificial sequence
<220> FEATURE:
<223> OTHER INFORMATION: antisense oligonucleotide

<400> SEQUENCE: 8
ccctctgctc ccatgggc                                              19

<210> SEQ ID NO 9
<211> LENGTH: 20
<212> TYPE: DNA
<213> ORGANISM: artificial sequence
<220> FEATURE:
<223> OTHER INFORMATION: antisense oligonucleotide

<400> SEQUENCE: 9
ccctctgctc cccatgggca                                            20

<210> SEQ ID NO 10
<211> LENGTH: 16
<212> TYPE: DNA
<213> ORGANISM: artificial sequence
<220> FEATURE:
<223> OTHER INFORMATION: antisense oligonucleotide

<400> SEQUENCE: 10
gctccccatg ggcaac                                                16

<210> SEQ ID NO 11
```

```
<211> LENGTH: 17
<212> TYPE: DNA
<213> ORGANISM: artificial sequence
<220> FEATURE:
<223> OTHER INFORMATION: antisense oligonucleotide

<400> SEQUENCE: 11
ccctctgctc cccatgg                                                    17

<210> SEQ ID NO 12
<211> LENGTH: 18
<212> TYPE: DNA
<213> ORGANISM: artificial sequence
<220> FEATURE:
<223> OTHER INFORMATION: antisense oligonucleotide

<400> SEQUENCE: 12
atgggcaact gccaggca                                                   18

<210> SEQ ID NO 13
<211> LENGTH: 20
<212> TYPE: DNA
<213> ORGANISM: artificial sequence
<220> FEATURE:
<223> OTHER INFORMATION: antisense oligonucleotide

<400> SEQUENCE: 13
catgggcaac tgccaggcag                                                 20

<210> SEQ ID NO 14
<211> LENGTH: 16
<212> TYPE: DNA
<213> ORGANISM: artificial sequence
<220> FEATURE:
<223> OTHER INFORMATION: antisense oligonucleotide

<400> SEQUENCE: 14
atgggcaact gccagg                                                     16

<210> SEQ ID NO 15
<211> LENGTH: 20
<212> TYPE: DNA
<213> ORGANISM: artificial sequence
<220> FEATURE:
<223> OTHER INFORMATION: antisense oligonucleotide

<400> SEQUENCE: 15
actgccaggc agggcacaac                                                 20

<210> SEQ ID NO 16
<211> LENGTH: 18
<212> TYPE: DNA
<213> ORGANISM: artificial sequence
<220> FEATURE:
<223> OTHER INFORMATION: antisense oligonucleotide

<400> SEQUENCE: 16
ggcaactgcc aggcaggg                                                   18

<210> SEQ ID NO 17
<211> LENGTH: 19
<212> TYPE: DNA
<213> ORGANISM: artificial sequence
```

```
<220> FEATURE:
<223> OTHER INFORMATION: antisense oligonucleotide

<400> SEQUENCE: 17
gggcaactgc caggcaggg                                              19
```

INDUCTION OF APOPTOSIS AND CELL GROWTH INHIBITION BY PROTEIN 4.33

CROSS-REFERENCE TO RELATED APPLICATIONS

This application is a U.S. nationalization, under 35 U.S.C. § 371, of PCT/US01/16437, filed 17 May 2001 and entitled INDUCTION OF APOPTOSIS AND CELL GROWTH INHIBITION BY PROTEIN 4.33, and additionally claims the benefit of priority to U.S. Provisional Patent Application Ser. No. 60/204,949, filed 17 May 2000 and of same title, and which is incorporated herein by reference in its entirety.

STATEMENT REGARDING FEDERALLY-SPONSORED RESEARCH

This work was supported by Department of Defense grant 17-96-1-6304 and 17-97-1-7204. The United States has certain rights in this invention, pursuant to 35 U.S.C. § 202(c)(6).

TECHNICAL FIELD OF THE INVENTION

The present invention provides drug candidate screening assays, and diagnostic and therapeutic methods for the treatment of cancer, tumor suppression, utilizing a novel IGFBP-3 interacting protein called P4.33 as the intervention target. The present invention further provides a P4.33 cDNA sequence, a P4.33 polypeptide and fragments thereof, and an anti-P4.33 antibody.

BACKGROUND OF THE INVENTION

The insulin-like growth factor ("IGF") signaling system ("IGF axis") is comprised of the ligands IGF-I, IGF-II and insulin, and a family of transmembrane receptors including the insulin, and the type-1 and type-2 IGF receptors.

Additionally, the IGF axis includes the insulin-like growth factor binding proteins ("IGFBPs"). Six IGFBPs have been identified, cloned and sequenced. These IGFBPs share a high degree of similarity in their primary protein structure, particularly in the corresponding N- and C-terminal regions, which are separated by a variable mid-protein segment of 55 to 95 amino acid residues. The IGFBPs bind IGF-I and IGF-II, but not insulin, with high affinity. The IGFBPs appear to serve essential functions of transporting the IGFs, prolonging IGF half-lives, and regulating the availability of free IGFs for interaction with IGF receptors. Accordingly, the IGFBPs modulate the effects of IGFs on growth and differentiation. Some IGFBPs (e.g., IGFBP-3) may also be important growth-suppressing factors in various cell systems through an IGF-independent mechanism.

Other potential IGF binding proteins, referred to as IGFBP-related proteins ("IGFBP-rPs"), have been identified that have a significant similarity to the IGFBPs in their N-terminal domains. Collectively, current data supports the broad concept of an "IGFBP superfamily" with both high- and low-affinity members, wherein at least some members influence cell growth and differentiation by both IGF-dependent and IGF-independent means.

The human IGFBP superfamily is currently comprised of six high-affinity species (IGFBPs 1-6), and nine low-affinity IGFBP-related proteins (IGFBP-rPs). Structural characteristics of various members of the human IGFBP superfamily are summarized in Table 1.

TABLE 1

Structural Characteristics of the Human IGFBP Superfamily

| IGFBP | Molecular Weight | Number of amino acids | Number of cysteines | N-linked glycosylation | Chromosomal localization | mRNA size (kb) |
|---|---|---|---|---|---|---|
| High affinity IGFBP related proteins | | | | | | |
| IGFBP-1 | 25,271 | 234 | 18 | No | 7p | 1.6 |
| IGFBP-2 | 31,355 | 289 | 18 | No | 2q | 1.5 |
| IGFBP-3 | 28,717 | 264 | 18 | Yes | 7p | 2.4 |
| IGFBP-4 | 25,957 | 237 | 20 | Yes | 17q | 1.7 |
| IGFBP-5 | 28,553 | 252 | 18 | No | 2q | 1.7, 6.0 |
| IGFBP-6 | 22,847 | 216 | 16 | No | 12 | 1.1 |
| Low affinity IGFBP related proteins | | | | | | |
| IGFBP-rP1 | ? | 251 | 18 | Yes | 4q | 1.1 |
| IGFBP-rP2 | ? | 349 (pre) | 39 | Yes | 6q | 2.4 |
| IGFBP-rP3 | ? | 357 (pre) | 41 | ? (No) | 8q | 2.4 |
| IGFBP-rP4 | ? | 379 (pre) | 35 | ? (No) | ? | 2.4 |

IGFBP-3 is the principal IGFBP in adult serum, where it circulates as a 150 kDa-complex comprising IGFBP-3, an acid-labile subunit, and IGF peptide. Its principal role has been postulated to be transporting IGFs and protecting them from rapid clearance and/or degradation.

Cancer cell growth regulation. The IGFs are major regulators of mammary epithelial and breast cancer cell growth. For example, IGF-I and IGF-II are potent mitogens for a number of breast cancer cell lines in vitro. Moreover, IGF-I and IGF-II mRNAs are detectable in the majority of human breast tumor specimens. Virtually all breast tumor specimens, and cell lines derived therefrom, express and produce type-1 and type-2 IGF receptors, and insulin receptors. The mitogenic effects of both IGF-I and IGF-II are mediated by the type-1 IGF receptor, as determined through the use of estrogen-dependent breast cancer cells.

In contrast, relatively little is known about the molecular mechanisms and biological functions of the IGFBPs in the context of breast cancer. Specifically, breast cancer cells are known to secrete various types of IGFBPs, and these appear to regulate the availability of free IGFs for interaction with IGF receptors. The predominant secreted IGFBP appears to correlate with the estrogen receptor status of the cell. Estrogen-non-responsive (i.e., estrogen receptor ("ER")-negative) cells secrete predominantly IGFBP-3 and IGFBP-4 as major species, and IGFBP-6 as a minor one. Estrogen-responsive (ER-positive) cells secrete IGFBP-2 and IGFBP-4 as major species, and IGFBP-3 and IGFBP-5 as minor ones.

Therefore, the IGF axis in breast cancer is complex, involving autocrine, paracrine, or endocrine-derived IGFs that bind to specific cellular receptors and thereby elicit, among other things, IGFBP secretion by the target cells. The IGFBPs, in turn, appear to regulate the availability of free IGFs for interaction with IGF receptors. However, the broader biological significance of IGFBPs generally, or in the particular context of breast cancer is unclear. Moreover, the basis and significance of variations in IGFBP secretory specificity are unknown, and the predominant species may vary significantly depending on the estrogen responsivess of the secreting cells.

In human breast cancer cells, expression of IGFBP-3 is hormonally regulated, and IGFBP-3 is known to inhibit cancer cell growth through (a) IGF-dependent, and (b) IGF-independent mechanisms:

(a) IGF-dependent anti-proliferative action by IGFBPs. IGFBP-3 is known to indirectly inhibit cancer cell growth through IGF-dependent interactions. IGFBP-3, as mentioned above, is the predominant IGF-binding protein in human serum where it circulates as part of a 150 kDa ternary complex. The binding affinity of IGFBP-3 for IGF peptides is generally higher than that of the type-I and type-II IGF cell-surface receptors implying that IGFBP-3 can modulate IGF binding to its receptor, thereby blocking local IGF-dependent biological action. For example, coincubation of cells with IGFBP-3 and IGF peptides results in an inhibition of the IGF-dependent mitogenic effect in human breast cancer cells, in vitro. Studies of the expression of IGF-I and IGF-II in human breast cancer tissues by in situ hybridization indicate that IGF-I mRNA is detected only in stromal cells, but not in normal or malignant epithelial cells, implying that IGF-I may function as a paracrine stimulator of epithelial cells. In contrast, IGF-II mRNA is expressed in both malignant epithelial cells and their adjacent stromal cells. Both paracrine or autocrine effects of IGF peptides can be modulated in vivo by IGFBP-3 produced by epithelial cells.

This IGF-dependent mechanism for IGFBP-3 inhibition of cancer cell growth is consistent with IGFBP-3 proteolysis studies. Post-translationally, IGFBP-3 can be proteolyzed by proteases such as cathepsin D, prostate-specific antigen (PSA) and plasmin, that are detectable in human breast cancer cells. In general, IGFBP-3 proteases are postulated to lower the affinity of IGFBP-3 for IGF, thereby increasing the availability of IGFs to cell-membrane receptors. PSA, for example, has been shown to reverse the inhibitory effect of IGFBP-3 on IGF-stimulated prostate cell growth by cleaving IGFBP-3 and generating IGFBP-3 fragments with lower affinity for IGFs. Nonetheless, the broader biological significance, molecular actions and mechanisms of IGFBP-3 proteolysis are unclear in the context of human breast cancer.

(b) IGF-independent anti-proliferative action by IGFBPs. The IGFBPs may have specific IGF-independent biological effects in various cell systems, including human breast cancer cells. For example, exogenously added IGFBP-3 inhibits estrogen-stimulated breast cancer cell proliferation. Moreover, several studies have reported that estrogen inhibits expression and secretion of IGFBP-3, whereas anti-estrogens, such as tamoxifen and ICI 182,780, stimulate production of IGFBP-3 in ER-positive human breast cancer cells.

Likewise, the expression and production of IGFBP-3 is specifically stimulated by TGF-β and retinoic acid ("RA") in human breast cancer cells, consistent with a possible role for IGFBP-3 in TGF-β- and RA-induced growth inhibition. Additionally, the anti-proliferative effects of TGF-β, RA, TNF-α and vitamin-D analogs in human breast cancer cells appear to be partially mediated through the IGFBP-3 axis. These studies indicate that IGFBP-3 is an important IGF-independent anti-proliferative factor in human breast cancer cells.

Various experimental data support the ability of IGFBP-3 to induce apoptosis. For example, in MCF-7 cells, the treatment with recombinant human IGFBP-3 for 72 hours has been shown to increase apoptosis and to inhibit [$^3$H]-thymidine incorporation. In Hs578T human breast cancer cells, IGFBP-3 does not result in direct induction of apoptosis, but preincubation of the cells with IGFBP-3 causes a dose-dependent potentiation of apoptosis by ceramide, an apoptosis-inducing agent, consistent with an IGF-independent activity of IGFBP-3.

Finally, IGFBP-3 can bind to the cell surface and act as a growth inhibitor for ER-negative human breast cancer cells. The interaction of IGFBP-3 with the breast cancer cell surface, and its subsequent biological effects may involve IGFBP-3-specific cell surface association proteins that mediate the direct inhibitory effect of IGFBP-3 on the growth of cells in monolayer. However, nothing is known about the nature, size, number, absolute specificity or complexity of such postulated cell surface association proteins, and no such protein has ever been cloned, purified, or otherwise characterized to provide any information whatsoever as to the actual functional involvement or sufficiency of such proteins for specific cell surface IGFBP-3 binding, or for IGFBP-3 mediated, IGF-independent biological action.

Therefore, there is a need in the art to determine the nature and mechanism of how IGFBP-3 modulates cancer cell growth and apoptosis in an IGF-independent manner. There is a further need in the art to understand how such a mechanism, once determined, could be used therapeutically, or to find therapeutic agents, or to provide useful diagnostic and prognostic assays for various cancers.

SUMMARY OF THE INVENTION

This present specification discloses the identification and characterization of a novel protein, P4.33, that interacts specifically with IGFBP-3 in an IGF-independent manner. P4.33 functions as a receptor for IGFBP-3, and is subsequently involved in the inhibition of DNA synthesis and cellular proliferation, and in the induction of apoptosis in cancer cells. The present invention provides for, but is not limited to: P4.33 DNA, proteins and cells expressing P4.33-specific sequences; P4.33-based screening assays for identifying test compounds having cancer therapeutic activity; Methods for treating or preventing cancer in a patient needing treatment; Assays for cancer treatment, prognosis or diagnosis in a patient for cancer cells that express P4.33; Anti-P4.33 antibodies, P4.33-specific antisense and ribozyme agents, and anticancer pharmaceutical compositions.

BRIEF DESCRIPTION OF THE FIGURES

FIG. 2C shows the sequence of the novel 4.33 cDNA clone ([SEQ ID NO:1]). The 4.33 cDNA clone was sequenced to reveal a 915 bp cDNA with a translational start site (ATG, bold face) 37 bases from the 5' end, and a translational stop codon (TGA, bold face) delimiting an open-reading frame coding for 240 amino acids.

FIGS. 7B-1 and 7B-2 show a schematic diagram of the ecdysone-inducible expression system used to generate stably transfected MCF-7 cells that either constitutively or inducibly (in response to about 2-15 µM ponasterone) express IGFBP-3 (FIGS. 7B-1). FIGS. 7B-2 shows the relative expression characteristics of sixteen isolated colonies tested for inducible IGFBP-3 expression with Ponasterone A. Colonies 1 and 16 express IGFBP-3 constitutively, whereas colonies 2, 3 and 6 demonstrate inducible expression.

FIG. 11 summarizes the results of MTS proliferation assays of Hs578t, MDA231, PC-3 and H157 cell cultures that were infected with Ad:IGFBP-3R either in the absence, or the presence of tetracyclin. Growth inhibition is expressed as a percent of the control value, which is the growth rate in the presence of tetracyclin, which suppresses P4.33 (IGFBP-3R) expression. Ad:IGFBP-3R-mediated over-expression of the IGFBP-3R resulted in substantial growth inhibition compared to uninfected cells. For example, in PC-3 prostate cancer cells, IGFBP-3R over-expression resulted in about 90% growth inhibition compared to infected cells in the presence of tetracyclin.

DETAILED DESCRIPTION OF THE INVENTION

Definitions

Figure 1:
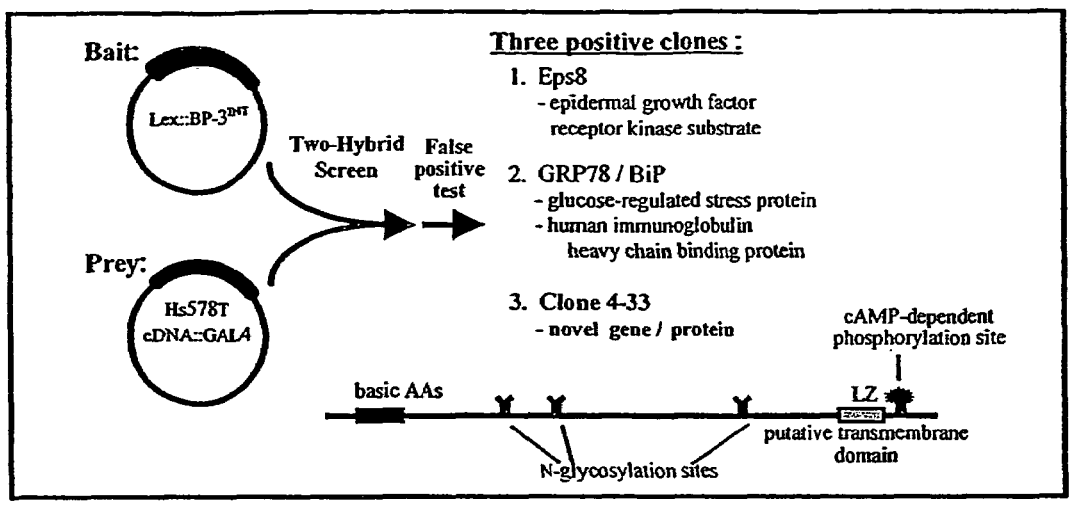
FIG. 1 shows a schematic diagram of the isolation process for isolating the P4.33 cDNA using the yeast two-hybrid system. An internal portion of the IGFBP-3 cDNA, coding for amino acids 88-148, was fused to the Lex DNA binding domain. A cDNA library, generated from Hs578 human breast cancer cell mRNA, was fused to the GAL4 transcriptional activation domain. These were used in the yeast two-hybrid system to identify clones that interact with IGFBP-3. A novel cDNA clone, 4.33, was isolated.

The following terms as used herein shall have the meaning indicated:

P4.33 means, as disclosed herein, the IGFBP-3 receptor (IGFBP-3R) (SEQ ID NO:2), and also encompasses P4.33 gene products, such as transcripts and the P4.33 protein (IGFBP-3R), polypeptides or fusion proteins. Polypeptides or peptide fragments of the P4.33 are referred to as P4.33 polypeptides or P4.33 peptides. Fusions of P4.33, or P4.33 polypeptides, or peptide fragments to an unrelated protein are referred to herein as P4.33 fusion proteins. A functional P4.33 refers to a protein that binds IGFBP-3, or IGFBP-3 peptides in vivo or in vitro, or that mediates signal transduction, such as caspase activation.

P4.33 nucleotides or coding sequences: means DNA sequences encoding P4.33 mRNA transcripts, P4.33 protein, polypeptide or peptide fragments of P4.33, or P4.33 fusion proteins. P4.33-nucleotide sequences encompass DNA, including genomic DNA (e.g., the P4.33 gene) or cDNA (SEQ ID NO:1).

Anti-P4.33 antibody means an antibody, or binding fragment thereof, that binds to (i.e., that recognizes one or more P4.33 epitopes of) a P4.33 receptor, protein, or polypeptide, or to a P4.33 fusion protein through interaction with, at least in part, P4.33 epitopes of said fusion protein. Anti-P4.33 antibodies include, but are not limited to, double-chain, single-chain, Fab fragments, F(ab')$_2$ fragments, anti-idiotypic antibodies, polyclonal, monoclonal, chimeric, humanized antibodies, and P4.33 eptiope-binding fragments of any of the foregoing.

IGFBP-3 means "Insulin-like Growth Factor Binding Protein-3," IGFBP-3 gene products, e.g., transcripts and the IGFBP-3 protein. Polypeptides or peptide fragments of the IGFBP-3 are referred to as IGFBP-3 polypeptides or IGFBP-3 peptides. Fusions of IGFBP-3, or IGFBP-3 polypeptides, or peptide fragments to an unrelated protein are referred to herein as IGFBP-3 fusion proteins. A functional IGFBP-3 refers to a protein that binds P4.33, or P4.33 peptides in vivo or in vitro.

"Hs578T" and "MCF-7" are art-recognized human breast cancer cell lines;

"PC-3" and "LNCaP" are art-recognized human prostate cancer cell lines;

"FLAG" means the art-recognized FLAG epitope tag;

"LZ" means leucine zipper motif;

"HA" means "the epitope tag YPYDVPDYA";

"GST" means "glutathione S-transferase."

Overview

The present invention relates to the biological role of IGFBP-3 in regulating cell growth. A yeast two-hybrid system was used with a cDNA library from Hs578T breast cancer cells to clone and identify a novel cDNA, clone 4.33. The 4.33 cDNA (SEQ ID NO:1) encodes a novel protein, P4.33, that interacts specifically with IGFBP-3. P4.33 was used to generate α-P4.33 antibodies that enabled characterization of the cellular location of P4.33, and determination that P4.33 is a functional receptor for IGFBP-3 in the human breast cancer system. According to the present invention, the interaction of IGFBP-3 with P4.33 is an important mechanism in the IGF-independent, growth inhibitory and apoptotic actions of IGFBP-3 in human cancer cells.

Accordingly, the present invention provides a P4.33 cDNA sequence, a P4.33 polypeptide and fragments thereof, and α-P4.33 antibodies. The present invention further provides drug candidate screening assays, and diagnostic and therapeutic methods useful for the treatment of cancer and tumor suppression, utilizing a novel IGFBP-3 interacting protein called P4.33 as the intervention target. The present invention also encompasses pharmaceutical formulations.

In particular embodiments, the present invention encompasses screening methods (e.g., assays) for identification of cancer therapeutic compounds. Additional embodiments encompasses agonists and antagonists of P4.33, including small molecules, large molecules, and antibodies, as well as nucleotide sequences that can be used to inhibit P4.33 gene expression, such as antisense and ribozyme molecules. The invention also encompasses the use of such compounds to treat cancer.

In particular, cellular and noncellular assays are described that can be used to identify compounds that interact with P4.33, and/or IGFBP-3, to mimic, modulate or antagonize association between these two molecules, and/or to modulate the activity of P4.33, IGFBP-3, or the P4.33:IGFBP-3 complex. The cell based assays can be used to identify compounds or compositions that affect the activity, nuclear translocation, or cellular compartmentalization of P4.33, IGFBP-3, or the P4.33:IGFBP-3 complex, whether they bind to of P4.33, IGFBP-3, or the P4.33:IGFBP-3 complex or act on intracellular factors involved in the downstream signal transduction pathway. Such cell-based assays of the invention utilize cells, cell lines, or engineered cells or cell lines that express P4.33 and/or IGFBP-3, or fusions thereof with unrelated proteins.

The cells can be further engineered to incorporate a reporter molecule linked to the signal transduced by P4.33, IGFBP-3, or the P4.33:IGFBP-3 complex to aid in the identification of compounds that modulate P4.33-mediated signaling activity.

Additional embodiments encompasses the use of cell-based assays, or cell-lysate assays (e.g., in vitro transcription or translation assays) to screen for compounds or compositions that enhance P4.33 gene expression. Such assays could be used, for example, to screen for transcriptional or translational activators. Alternatively, engineered cells or translation extracts can be used to screen for compounds (including antisense, ribozyme and or triple-helix agents) that inhibit the translation of P4.33 mRNA transcripts, and therefore, affect expression of P4.33.

Further embodiments encompasses P4.33 proteins, polypeptides (including soluble P4.33 polypeptides or peptides) and P4.33 fusion proteins for use in cell, and non-cell based assays for screening compounds that interact with, and/or modulate the activity of P4.33, IGFBP-3, or the P4.33:IGFBP-3 complex, for use in generating antibodies, and for diagnostics and therapeutics.

P4.33 protein products can be used as P4.33 antagonists or agonists to treat cancer. Such P4.33 protein products include but are not limited to peptides or polypeptides corresponding to one or more P4.33 domains (e.g., the IGFBP-3 interaction domain), truncated P4.33 polypeptides lacking one or more P4.33 domains (e.g., lacking the transmembrane domain, glycosylation sites, or the cAMP-dependent phosphorylation site), and P4.33 fusion protein products (e.g., GST fusions, or epitope-tagged fusions, including EGFP and FLAG fusions). Alternatively, antibodies to the P4.33 that are P4.33 agonists or antagonists (including compounds that modulate signal transduction that may act on downstream targets in the P4.33 signal transduction pathway) can be used to treat cancer.

For example, in particular embodiments, an effective amount of an appropriate soluble P4.33 polypeptide, or a P4.33 fusion protein (e.g., P4.33 $^{HA}$) is administered to interact with and thereby alternatively "activate," "neutralize," or "mop up" endogenous IGFBP-3, to modulate the activity of P4.33, IGFBP-3, or the P4.33:IGFBP-3 complex. Alternatively, nucleotide constructs encoding such P4.33 products can be used to genetically engineer host cells to express such P4.33 products in vivo, where such cells function as "bioreactors" in the body, delivering a continuous supply of the appropriate P4.33, P4.33 peptide, soluble P4.33 polypeptide, or P4.33 fusion protein to alternatively "activate," "neutralize," or "mop up" endogenous IGFBP-3.

Gene therapy approaches for the modulation of P4.33 expression and/or activity in the treatment of cancer are also within the scope of the invention. For example, nucleotide constructs encoding functional P4.33, mutant P4.33, as well as antisense and ribozyme molecules can be used to regulate P4.33 expression.

Specific embodiments of the present invention include, but are not limited to the following: (i) P4.33 DNA, Proteins and Cells Expressing P4.33-Specific Sequences; (ii) P4.33-based Screening Assays for Identifying Test Compounds Having Cancer Therapeutic Activity; (iii) Methods for Treating or Preventing Cancer in a Patient Needing Treatment; (iv) Assays for Cancer Treatment, Prognosis or Diagnosis in a Patient for Cancer Cells that Express P4.33; (v) Anti-P4.33 Antibodies, P4.33-Specific Antisense and Ribozyme Agents, and Anticancer Pharmaceutical Compositions.

(i) P4.33 DNA, Proteins and Cells Expressing P4.33-Specific Sequences

Specifically, the present invention provides for an isolated DNA sequence encoding a P4.33 polypeptide and comprising a coding region of the sequence described in SEQ ID NO:1, or a sequence having at least 90% homology with the coding region of SEQ ID NO:1.

Additionally, the present invention provides for an isolated P4.33 protein or polypeptide, expressed by the cDNA sequence described in SEQ ID NO:1, or expressed by a sequence having at least 90% homology with the coding region of SEQ ID NO:1.

The present invention further provides for a fusion protein comprising a P4.33 protein or polypeptide operatively associated with a heterologous polypeptide.

The present invention further provides for a transfected cell comprising an expression vector having a DNA sequence that codes on expression for a P4.33 protein or polypeptide taken from the sequence of SEQ ID NO:1, or for a fusion protein comprising the P4.33 protein or polypeptide operatively associated with a heterologous polypeptide.

(ii) P4.33-Based Screening Assays for Identifying Test Compounds Having Cancer Therapeutic Activity Additionally, the present invention provides methods for identifying test compounds having cancer therapeutic activity, comprising: (a) contacting a test compound with a cell expressing a functional P4.33 receptor or a recombinant P4.33 protein, polypeptide or fusion protein; and (b) determining whether the test compound functionally interacts with the P4.33 receptor or recombinant P4.33 protein, polypeptide or fusion protein, whereby test compounds that functionally interact with the P4.33 receptor or recombinant P4.33 protein, polypeptide or fusion protein are identified as cancer therapeutic compounds.

Preferably, the determination of the functional interaction between the test compound and the P4.33 receptor or recombinant P4.33 protein, polypeptide or fusion protein is based on an assay selected from the group consisting of direct receptor binding assays, IGFBP-3 antagonist assays, receptor activation or sensitization assays, receptor deactivation or desensitization assays, receptor up-regulation or down-regulation assays, receptor-mediated signal transduction assays, cell growth rate assays, detection of nuclear translocation of the P4.33 receptor or recombinant protein polypeptide or fusion protein, and detection of a specific marker of cell differentiation.

Preferably, the the receptor mediated signal transduction assays are based on determining the phosphorylation or activation status of an intracellular protein, wherein the intracellular protein is selected from the group consisting of Ras, PKA, RAP1, B-Raf, Mek, and MAPK, whereby test compounds that alter the phosphorylation or the activation status of said proteins are identified as cancer therapeutic compounds.

Preferably, the specific marker of cellular differentiation is selected from the group consisting of cell cycle regulatory proteins cyclin D1, cyclin E and p21/Waf1, whereby test compounds that alter said specific markers of cellular differentiation, relative to control cells, are identified as cancer therapeutic compounds.

The present invention further provides methods for identifying test compounds having cancer therapeutic activity, comprising: (a) contacting a test compound, in the presence of a functional IGFBP-3 protein, polypeptide or fusion protein, with a cell expressing a functional P4.33 receptor or recombinant P4.33 protein, polypeptide or fusion protein;

and (b) determining whether the test compound inhibits the interaction between the IGFBP-3 protein, polypeptide or fusion protein, and the P4.33 receptor or recombinant P4.33 protein, polypeptide or fusion protein, whereby test compounds that inhibit the interaction between IGFBP-3 protein, polypeptide or fusion protein and the P4.33 receptor or recombinant P4.33 protein, polypeptide or fusion protein are identified as cancer therapeutic compounds.

Preferably, the determination of the inhibition of interaction between the IGFBP-3 protein, polypeptide or fusion protein, and the P4.33 receptor or recombinant P4.33 protein, polypeptide or fusion protein is based on an assay selected from the group consisting of receptor binding assays, receptor-activation or sensitization assays, receptor deactivation or desensitization assays, receptor up-regulation or down-regulation assays, receptor-mediated signal transduction assays, cell growth rate assays, detection of IGFBP-3-mediated nuclear co-translocation of the P4.33 receptor or recombinant P4.33 protein, polypeptide or fusion protein, and detection of a specific marker of cell differentiation.

Preferably, the receptor mediated signal transduction assays are based on determining the phosphorylation or activation status of an intracellular protein, wherein the intracellular protein is selected from the group consisting of Ras, PKA, RAP1, B-Raf, Mek, and MAPK, whereby test compounds that alter the phosphorylation or the activation status of said proteins are identified as cancer therapeutic compounds.

Preferably, the specific marker of cellular differentiation is selected from the group consisting of cell cycle regulatory proteins cyclin D1, cyclin E and p21/Waf1, whereby test compounds that alter said specific markers of cellular differentiation, relative to control cells, are identified as cancer therapeutic compounds.

The present invention further provides methods for identifying test compounds having cancer therapeutic activity, comprising: (a) contacting a test compound with an immobilized recombinant P4.33 receptor, protein, polypeptide or fusion protein; and (b) determining whether the test compound interacts with the immobilized recombinant P4.33 receptor, protein, polypeptide or fusion protein, whereby test compounds that interact with the immobilized recombinant P4.33 protein, polypeptide or fusion protein are identified as cancer therapeutic compounds.

Preferably, the determination of the interaction between the test compound and the recombinant P4.33 receptor, protein, polypeptide or fusion protein is based on an assay selected from the group consisting of direct receptor binding assays and IGFBP-3 antagonist assays.

Preferably, this method further comprises: (a) contacting the test compounds that interact with the immobilized recombinant P4.33 receptor, protein, polypeptide or fusion protein, with a cell expressing a functional P4.33 receptor or recombinant P4.33 protein, polypeptide or fusion protein; and (b) determining whether the test compound functionally interacts with the P4.33 receptor or recombinant P4.33 protein, polypeptide or fusion protein, whereby test compounds that functionally interact with the P4.33 receptor or recombinant P4.33 protein, polypeptide or fusion protein are identified as cancer therapeutic compounds.

The present invention further provides methods for identifying test compounds having cancer therapeutic activity, comprising: (a) contacting a functional IGFBP-3 protein, polypeptide or fusion protein, in the presence of a test compound, with a functional P4.33 receptor or recombinant P4.33 protein, polypeptide or fusion protein; and (b) determining whether the test compound inhibits the interaction between the IGFBP-3 protein, polypeptide or fusion protein and the P4.33 receptor or recombinant P4.33 protein, polypeptide or fusion protein, whereby test compounds that inhibit said interaction are identified as cancer therapeutic compounds.

The present invention further provides methods for identifying test compounds having cancer therapeutic activity, comprising: (a) contacting a test compound with a cell expressing, or a cell lysate containing P4.33 mRNA sequences; and (b) determining whether the test compound modulates transcription or translation of the P4.33 mRNA sequences, whereby test compounds that modulate transcription or translation of the P4.33 mRNA sequences are identified as cancer therapeutic compounds.

(iii) Methods for Treating or Preventing Cancer in a Patient Needing Treatment

The present invention further provides methods for treating or preventing cancer in a patient needing treatment comprising administering to the patient in which such treatment or prevention is desired a therapeutically effective amount of an anti-P4.33 antibody that binds to the extracellular domain of P4.33. Preferably, the cancer to be treated or prevented is lung, cervical, breast, colon or prostate carcinoma.

The present invention further provides methods for treating or preventing cancer in a patient needing treatment comprising administering to the patient in which such treatment or prevention is desired a therapeutically effective amount of an anti-P4.33 antisense molecule, or of a ribozyme molecule. Preferably, the cancer to be treated or prevented is lung, cervical, breast, colon or prostate carcinoma.

The present invention further provides methods for targeting a therapeutic agent to solid tumor tissue, wherein the solid tumor tissue is characterized by expression of P4.33, comprising attaching the therapeutic agent to an isolated polypeptide, wherein the polypeptide binds to the extracellular domain ("ECD") of P4.33 at an affinity of at least $10^8$.

Preferably, the isolated polypeptide is an anti-P4.33 monoclonal antibody or binding fragment thereof, or is IGFBP-3 or a functional fragment thereof.

(iv) Assays for Cancer Treatment, Prognosis or Diagnosis in a Patient for Cancer Cells that Express P4.33

The present invention further provides assays for cancer treatment, prognosis or diagnosis in a patient for cancer cells that express P4.33, comprising: (a) obtaining a bodily fluid sample from a patient; and (b) measuring the amount of P4.33 expressed using an anti-p68HER-2 antibody-based assay, wherein the assay is selected from the group consisting of ELISA, immunoprecipitation, immunohistocytochemistry, and Western analysis.

Preferably, the bodily fluid is selected from the group consisting of blood, serum, urine, lymph, saliva, tumor tissue, placental tissue, umbilical cord tissue, amniotic fluid, chorionic villi tissue and combinations thereof.

Preferably, the assay for cancer treatment, prognosis or diagnosis in a patient for cancer cells that express P4.33 further comprises measuring the amount of IGFBP-3, IGF-I or IGF-II in the bodily fluid.

The present invention further provides assays for cancer treatment, prognosis or diagnosis in a patient for cancer cells that express P4.33, comprising: (a) obtaining a bodily fluid sample from a patient; and (b) performing a sequence identity assay to detect P4.33-specific sequences.

Preferably, the bodily fluid is selected from the group consisting of blood, serum, urine, lymph, saliva, tumor tissue, placental tissue, umbilical cord tissue, amniotic fluid, chorionic villi tissue and combinations thereof.

Preferably, the sequence identity assay is selected from the group consisting of PCR assays, ELISA immunologic assays, hybridization assays, and combinations thereof.

Preferably, the assay for cancer treatment, prognosis or diagnosis in a patient for cancer cells that express P4.33 further comprises measuring the amount of IGFBP-3, IGF-I or IGF-II in the bodily fluid.

(v) Anti-P4.33 Antibodies, P4.33-Specific Antisense and Ribozyme Agents, and Anticancer Pharmaceutical Compositions The present invention further provides an antibody specific for a P4.33 protein or polypeptide of SEQ ID NO:1, or for a fusion protein thereof.

The present invention further provides an anticancer pharmaceutical composition comprising an antibody, or a binding fragment thereof, that binds to a P4.33 protein or polypeptide of SEQ ID NO:1, and a pharmaceutically acceptable carrier.

Preferably, the anti-P4.33 antibody is a monoclonal antibody. Even more preferably, the anti-P4.33 antibody is a humanized monoclonal antibody.

The present invention further provides an antagonist of P4.33 biological activity, wherein the antagonist is a P4.33-specific antisense molecule, or a P4.33-specific ribozyme molecule.

The present invention further provides for an anticancer pharmaceutical composition comprising a therapeutically effective amount of a P4.33 antagonist, and a pharmaceutically acceptable carrier, wherein the P4.33 antagonist is a P4.33-specific antisense molecule, or a P4.33-specific ribozyme molecule.

Preferably, the P4.33 antisense molecule is a P4.33-specific antisense oligonucleotide of at least 10 bases complementary to the P4.33 cDNA sequence (SEQ ID NO:1). Even more preferably, the P4.33-specific antisense oligonucleotide is a 15-25 base oligonucleotide incorporating an oligonucleotide sequence selected from the group consisting of: 5'-CTCAGCCCCCTCTGCTCCCC-3' (SEQ ID NO:3); 5'-CCTCTGCTCCCCATGGGCAAC-3' (SEQ ID NO:4); 5'-TGCTCCCCATGGGCAAC-3' (SEQ ID NO:5); 5'-CCCATGGGCAACTGCCAG-3' (SEQ ID NO:6); 5'-CCCCATGGGCAACTGCCAGG-3' (SEQ ID NO:7); 5'-CCCTCTGCTCCCCATGGGC-3' (SEQ ID NO:8); 5'-CCCTCTGCTCCCCATGGGCA-3' (SEQ ID NO:9); 5'-GCTCCCCATGGGCAAC-3' (SEQ ID NO:10); 5'-CCCTCTGCTCCCCATGG-3' (SEQ ID NO:11); 5'-ATGGGCAACTGCCAGGCA-3' (SEQ ID NO:12); 5'-CATGGGCAACTGCCAGGCAG-3' (SEQ ID NO:13); 5'-ATGGGCAACTGCCAGG-3' (SEQ ID NO:14); 5'-ACTGCCAGGCAGGGCACAAC-3' (SEQ ID NO:15); 5'-GGCAACTGCCAGGCAGGG-3' (SEQ ID NO:16); 5'-GGGCAACTGCCAGGCAGGG-3' (SEQ ID NO:17); and combinations thereof.

Cloning of a Novel IGFBP-3 Interacting Protein, P4.33

According to the present invention, a novel cDNA (SEQ ID NO:1, and FIG. 2C), clone 4.33, encoding a novel IGFBP-3 interacting protein (SEQ ID NO:2) was identified using the art-recognized "MATCH MAKER™" yeast-two hybrid system (Clontech) (FIG. 1, and EXAMPLE 1, below) with a cDNA library from Hs578T human breast cancer cells. The full-length clone 4.33 cDNA product was verified using the 5' RACE technique. The novel P4.33 cDNA was determined to be 915 bp in length, encoding a novel 240 amino acid leucine-rich (19%) protein (P4.33) (SEQ ID NO:2) with several potential glycosylation sites, a cAMP-dependent phosphorylation site, a single leucine zipper motif ("LZ") and a transmembrane ("TM") domain.

Expression Pattern of P4.33 mRNA in Multiple Human Tissues and Cell Lines

Figure 2A:
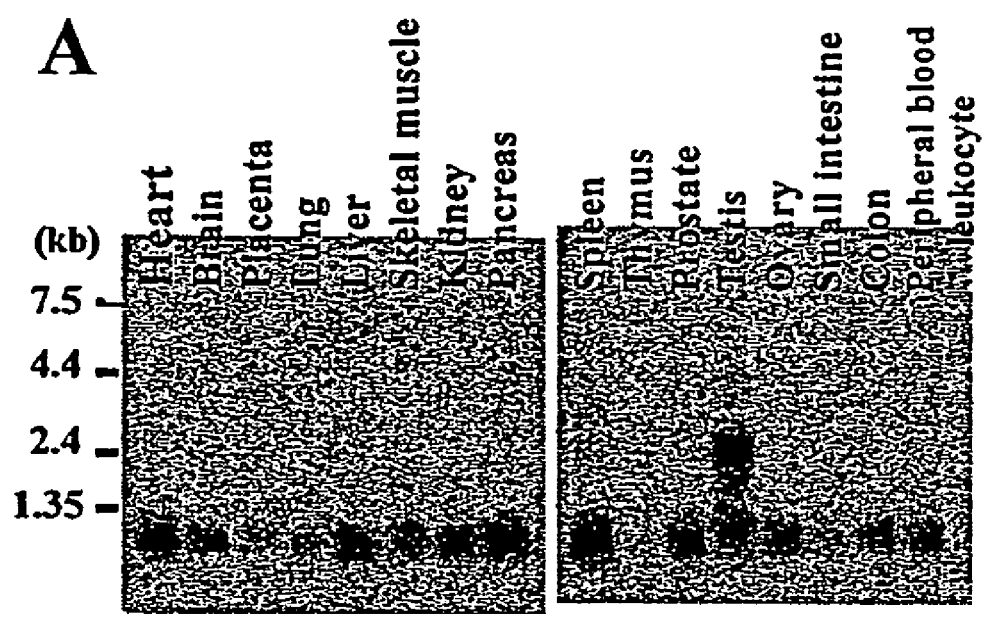
FIG. 2A shows the distribution of 4.33 mRNA in human tissues, based on a Northern blot analysis of 4.33 mRNA expression. Human multiple tissue Northern blots I & II (Clontech) were probed with labeled clone 4.33 cDNA.

Multi-tissue Northern blots, exposed to a P4.33-specific probe, were used to elucidate the expression pattern of the P4.33 gene in normal human tissues, in human cancer cell lines and in human mammary epithelial cells. These data showed that the P4.33 gene was expressed to varying degrees in all tissues tested (e.g., heart, brain, placenta, lung, liver, skeletal muscle, kidney, pancreas, spleen, thymus, prostate, testis, small intestine, colon, and peripheral blood leukocytes,) (FIG. 2A, and EXAMPLE 1). Specifically, a single transcript of about 915 nucleotides was detected to varying degrees in all tissues and cell lines tested. Differences in the relative expression level of this species were detected among the various human tissues and cell lines. Additionally, a second roughly 2 kb P4.33 transcript was detected in testis along with the 915 nucleotide transcript (Lane 12 of FIG. 2A).

Figure 2B:
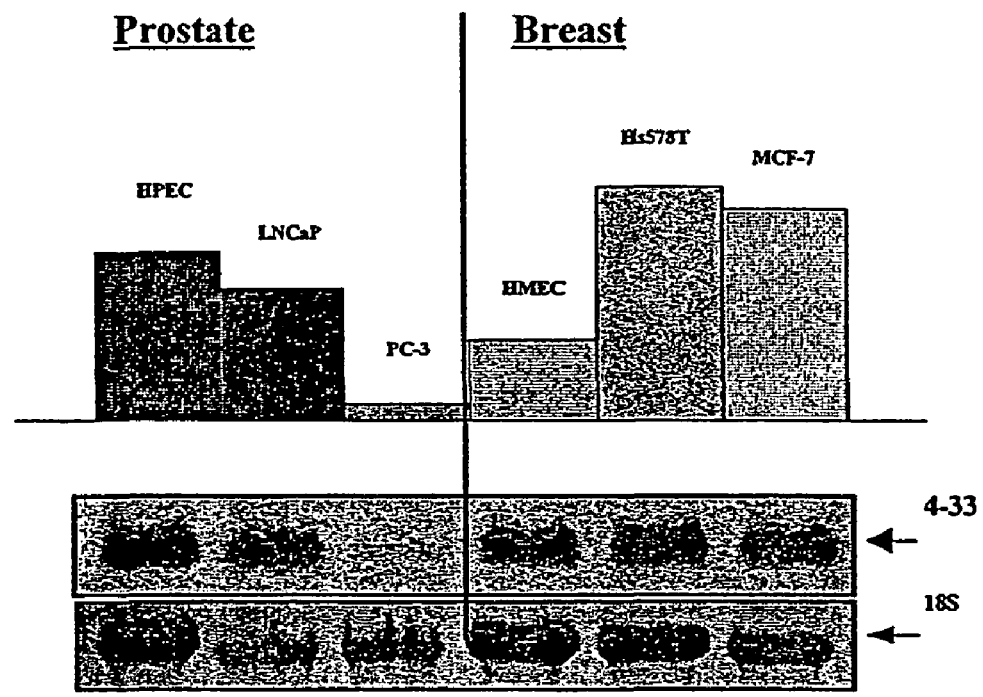
FIG. 2B shows that P4.33 appears to be differentially expressed in normal vs. cancerous human cell lines. Northern blots containing total RNAs from LNCaP and PC-3 human prostate cancer cells lines and human prostate epithelial cells (HPEC), Hs578T and MCF-7 human breast cancer cell lines an human mammary epithelial cells (HMEC) were probed with labeled clone 4.33 cDNA. The graph represents relative expression based on densitometric scans, normalized against 18S rRNA levels. A dramatic decrease in endogenous P4.33 expression is seen in PC-3 prostate cancer cells.

Significantly, the P4.33 gene was found to be differentially expressed in normal vs. cancerous human cell lines. A dramatic decrease in endogenous P4.33 expression was seen in PC-3 prostate cancer cells (FIG. 2B).

Cellular Localization of EGFP::P4.33 Fusion Protein, and Cellular Colocalization and Coimmunoprecipitation of IGFBP-3 and P4.33

Figure 3A:
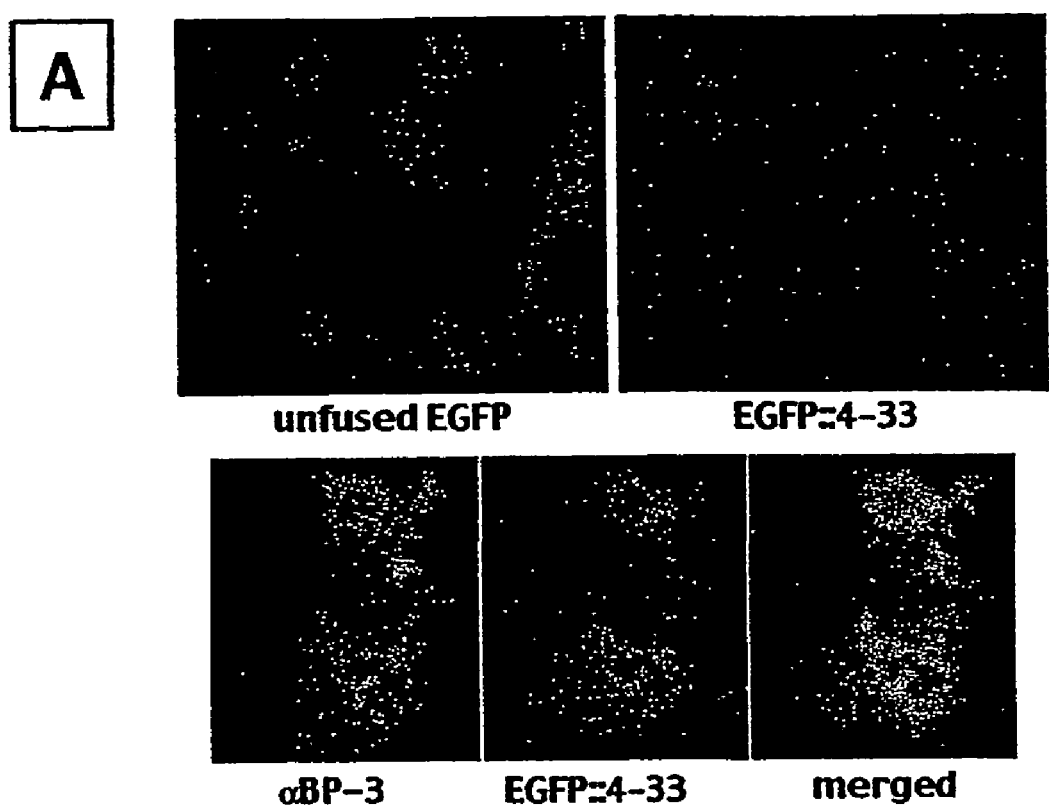
FIG. 3A shows the results of immunocytochemical staining in transiently transfected COS-7 cells. The interaction between IGFBP-3 and clone 4.33 was confirmed by immunocytochemistry (upper portion of FIG. 3A) and in coimmunoprecipitation studies (lower portion of FIG. 3B). The COS-7 cells were transiently transfected with or without constructs encoding an EGFP::4.33 fusion protein and FLAG-tagged IGFBP-3 (IGFBP-3$^F$). The EGFP::4.33 fusion protein exhibited a perinuclear, diffusely cytoplasmic, and possibly extracellular localization pattern relative to unfused EGFP (upper portion of FIG. 3A). The lower portion of FIG. 3A shows colocalization of co-transfected EGFP::4.33 and IGFBP-3$^F$ (i.e., flag IGFBP-3) proteins.
Figure 3B:
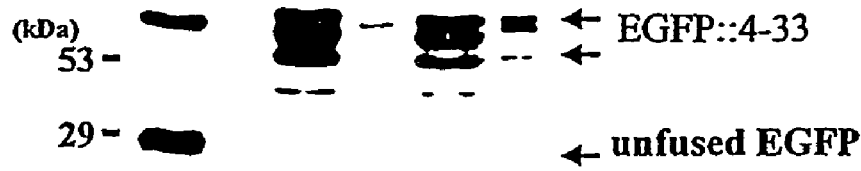
FIG. 3B shows co-immunoprecipitation of IGFBP-3 and clone 4.33. The EGFP::4.33 and IGFBP-3$^F$ proteins immunoprecipitated together from lysates of COS-7 cells transiently co-transfected with EGFP::4.33 and IGFBP-3$^F$, with no interaction seen in control samples, demonstrating specific stable interaction between these proteins in a mammalian cell system.
Figure 3B:
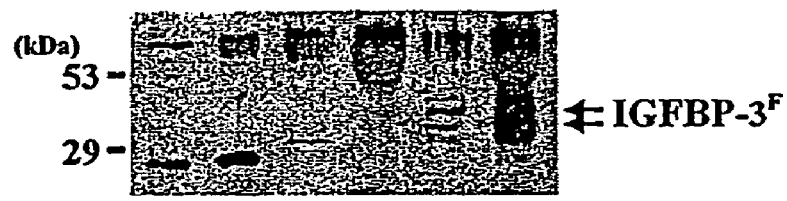

The interaction between IGFBP-3 and P4.33 in COS-7 cells was confirmed by immunocytochemistry (FIG. 3A, and EXAMPLE 2, below) and in co-immunoprecipitation studies (FIG. 3B, and EXAMPLE 2). COS-7 cells were transiently transfected with or without constructs encoding an EGFP::P4.33 fusion protein and FLAG-tagged IGFBP-3 (IGFBP-$3^F$). The expressed EGFP::P4.33 fusion protein exhibited a perinuclear, diffusely cytoplasmic, and possibly extracellular localization pattern. The expressed EGFP::P4.33 and IGFBP-$3^F$ proteins colocalized in the cytoplasm, cell membrane and possibly extracellular matrix. This same localization pattern was observed in transiently transfected Hs57ST and MCF-7 human breast cancer cells.

Additionally, EGFP::P4.33 and IGFBP-$3^F$ fusion proteins were immunoprecipitated together from lysates of COS-7 cells transiently co-transfected with EGFP::4.33 and IGFBP-$3^F$ (FIG. 3B, and EXAMPLE 2). No interaction was seen in control samples, demonstrating specific stable interaction between these proteins in mammalian cell systems.

Figure 4A:
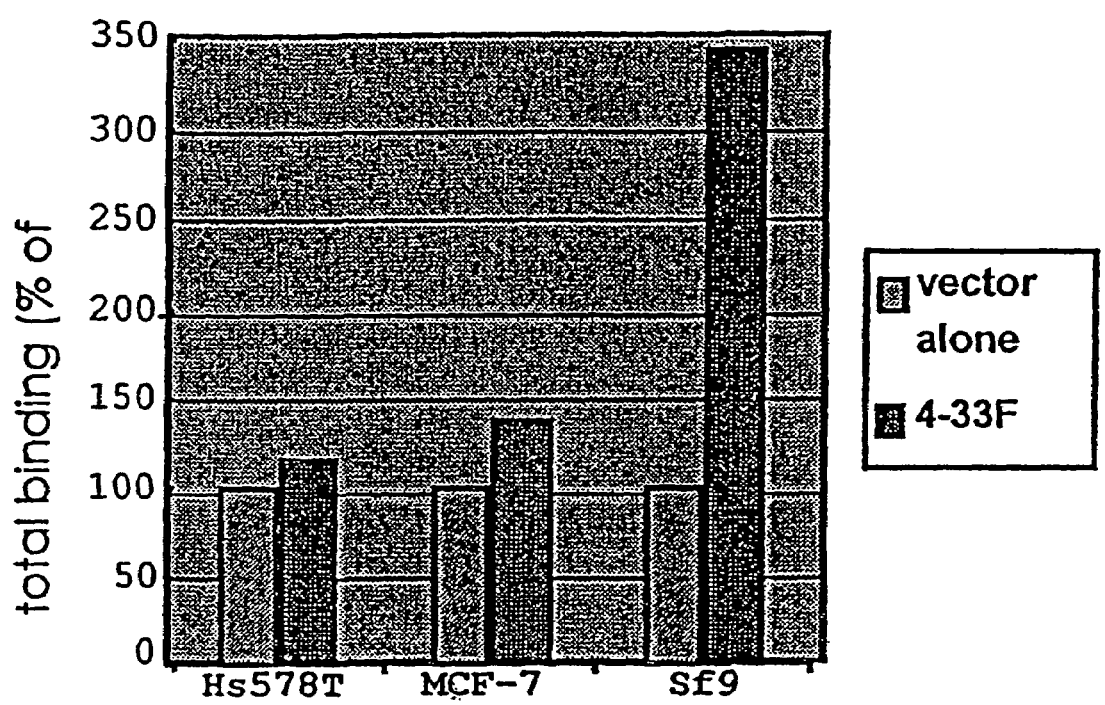
FIG. 4A shows that overexpression of clone 4.33 in mammalian cells resulted in a 30-60% increase in [$^{125}$I]-labelled IGFBP-3 cell-surface binding. This result was greatly magnified when the same assay was performed using Sf9 insect cells, either uninfected or infected with virus harboring the 4.33$^F$ cDNA, because the differential expression of P4.33$^F$ over control levels in these cells was considerably greater compared to differential overexpression in the tested mammalian cells.
Figure 4B:
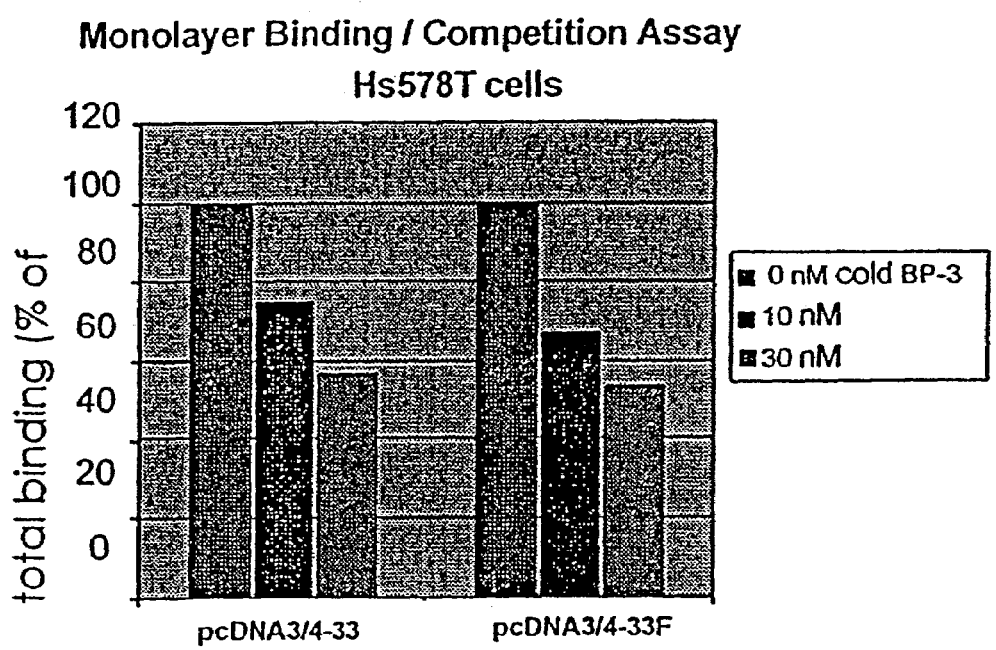
FIG. 4B shows that the enhanced IGFBP-3 binding following transfection of mammalian cells with 4.33 cDNA vector was specific, and was unaffected by the presence of the FLAG-tag at the C-terminus of P4.33$^F$. Hs578T cells were transiently transfected with vector alone, un-tagged or FLAG-tagged clone 4.33 for 36 hours. Cells were then washed and exposed to [$^{125}$I]-labelled IGFBP-3 plus and minus increasing amounts of unlabelled IGFBP-3 as indicated for 3 hours at 12° C. The measured [$^{125}$I]-labelled IGFBP-3 binding was competed in a dose-dependent manner by the addition of cold IGFBP-3, demonstrating specificity.

Cellular Overexpression of Clone 4.33 Resulted in Increased Specific IGFBP-3 Cell-Surface Binding, and Co-Translocation to the Nucleus The binding of [$^{125}$I]-labelled IGFBP-3 to Hs578T and MCF-7 human breast cancer cells, and Sf9 insect cells, previously transfected or infected (in the case of Sf9 cells) with a FLAG-tagged clone 4.33 vector or virus (in the case of Sf9 cells) was measured to determine whether the resulting expressed p4.33$^F$ could facilitate specific binding of [$^{125}$I]-labeled IGFBP-3 to the cells. Cell-surface binding of [$^{125}$I]-labeled IGFBP-3 was significantly enhanced in both mammalian and insect cells transfected with a clone 4.33 vector (FIG. 4A, and EXAMPLE 3, below). Furthermore, the enhanced [$^{125}$I]-labeled IGFBP-3 binding was specific, and was unaffected by the presence of the FLAG-tag at the C-terminus of P4.33$^F$ (FIG. 4B, and EXAMPLE 3).

Co-Translocation of P4.33$^F$ and IGFBP-3 to the Nucleus

Figure 5:
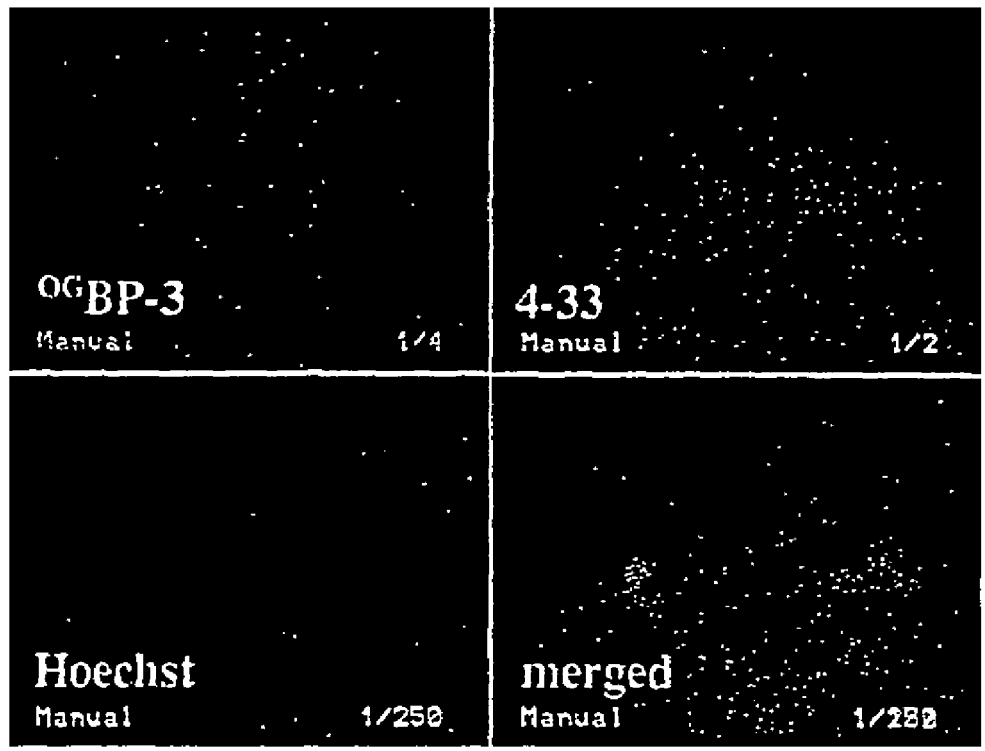
FIG. 5 shows co-translocation of p4.33$^F$ and Oregon-Green-labelled IGFBP-3 ($^{OG}$IGFBP-3) to the nucleus. Hs578T cells were transiently transfected with FLAG-tagged clone 4.33, and then incubated with $^{OG}$IGFBP-3. The uptake of $^{OG}$IGFBP-3 into the cells was apparent, as well as its further translocation to the nucleus. P4.33$^F$ colocalized with $^{OG}$IGFBP-3, whether cytoplasmic or nuclear, as shown in the representative images.

Purified IGFBP-3 that was labeled with OregonGreen ($^{OG}$IGFBP-3) to allow for tracking using fluorescent microscopy was used to examine whether the specific cell-surface binding of $^{OG}$IGFBP-3 resulted in uptake of $^{OG}$IGFBP-3 into Hs578T cells. The uptake of fluorescent $^{OG}$IGFBP-3 into Hs578T cells was readily apparent, as well as further translocation to the nucleus. The $^{OG}$IGFBP-3 colocalized with P4.33$^F$ in the cytoplasm, as detected by α-FLAG M2 antibody, and both were translocated to the nucleus (FIG. 5, and EXAMPLE 3). Additional experiments showed that nuclear localization of P4.33$^F$ was not seen in the absence of IGFBP-3, indicating that the nuclear transport of P4.33$^F$ is facilitated by IGFBP-3.

Figure 7A:
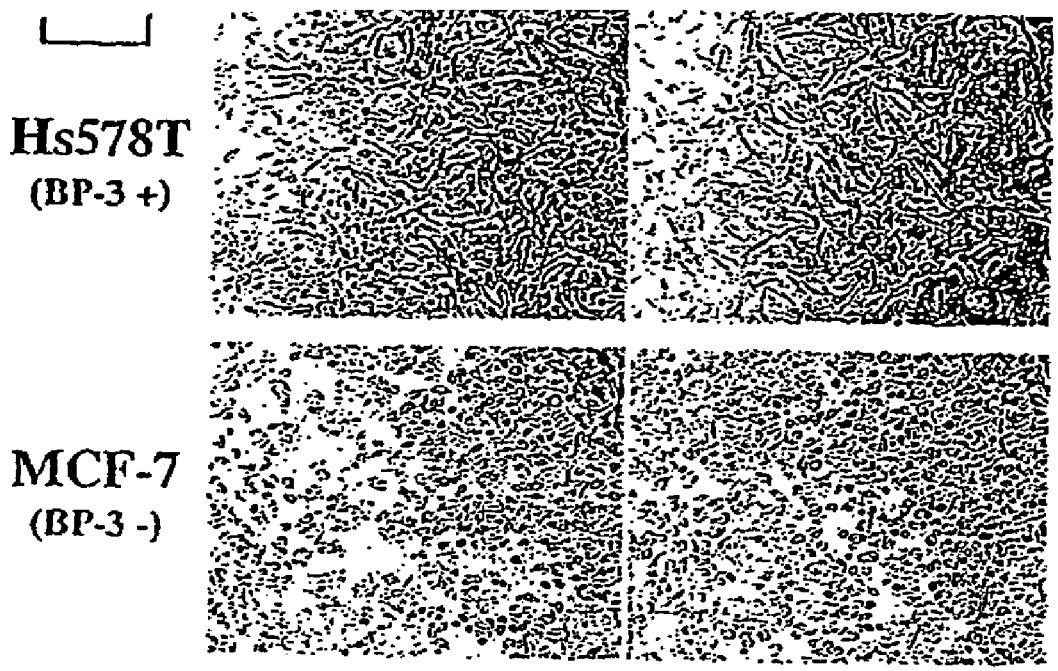
FIG. 7A shows that transient overexpression of P4.33 in IGFBP-3 expressing Hs578T breast cancer cells resulted in a significant increase in cell detachment and death over time, compared to little or no effect in MCF-7 cells that do not produce IGFBP-3. Hs578T (IGFBP-3-expressing) and MCF-7 (IGFBP-3-nonexpressing) cells were transiently transfected with control vector (CS2+) or FLAG-tagged clone 4.33 vector (CS/4.33$^F$). Representative phase contrast images of cell populations at 48 hours post-transfection were then examined for cell numbers.
Figure 7C:
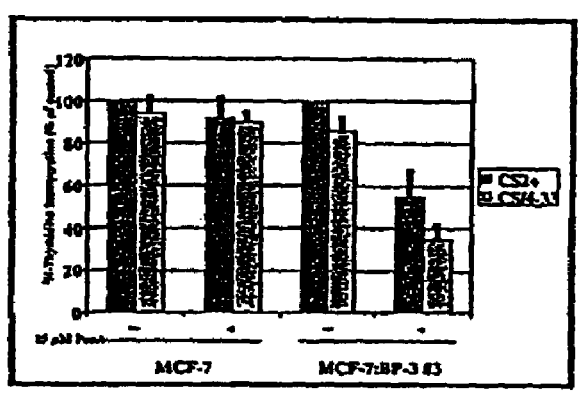
FIG. 7C shows that P4.33 enhances the IGFBP-3 growth-inhibitory effect on breast cancer cells as measured by thymidine incorporation. Induction of IGFB-3 in the absence of transiently expressed P4.33 suppressed DNA synthesis in MCF-7:BP-3, #3 cells by an average of 55% of control levels, whereas induction of IGFBP-3 in the presence of transiently expressed P4.33 further suppressed DNA synthesis in these cells to 35% of control levels. P4.33 expression had no significant effect in the absence of IGFBP-3 expression, and neither P4.33 nor ponasterone A had any effect in wild type MCF-7 cells. The data reflects the average of three independent experiments.

Transient Expression of P4.33 in the Presence of IGFBP-3 Resulted in Growth Inhibition and Cell Death P4.33$^F$ was transiently expressed in the presence of IGFBP-3 to investigate the effect of P4.33 on cancer cell growth. Transient overexpression of P4.33$^F$ in IGFBP-3-expressing Hs578T breast cancer cells resulted in a significant increase in cell detachment and death over time, compared to little or no effect in MCF-7 cells that do not produce IGFBP-3 (FIG. 7A, and EXAMPLE 5, below). Likewise, transient expression of P4.33$^F$ resulted in significantly enhanced inhibition of DNA synthesis (i.e., growth inhibition, or cell death) in a stably-transfected inducible IGFBP-3-expressing MCF-7 breast cancer cell line (FIG. 7B, FIG. 7C, and EXAMPLE 5).

Figure 7D:
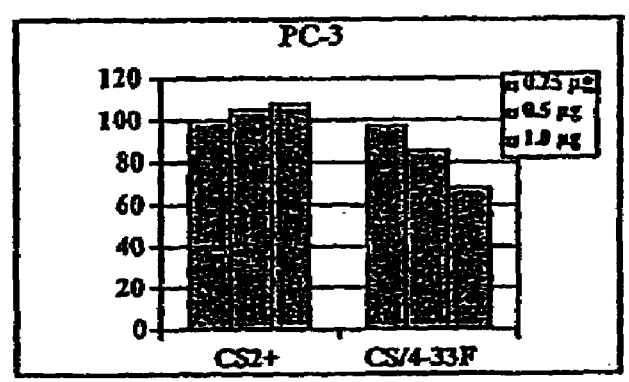
FIG. 7D shows that overexpression of P4.33 inhibited DNA synthesis in PC-3 prostate cancer cells, as determined by measurement of [$^3$H]-hymidine incorporation. In PC-3 prostate cancer cells, that produce IGFBP-3, DNA synthesis was inhibited by transient transfection of P4.33 relative to control transfected cells.

FIG. 7D shows that overexpression of P4.33 had a similar effect in PC-3 prostate cancer cells. In these cells, that produce IGFBP-3, DNA synthesis was inhibited by transient transfection of P4.33 relative to control transfected cells (FIG. 7D, and EXAMPLE 5)

Figure 8A:
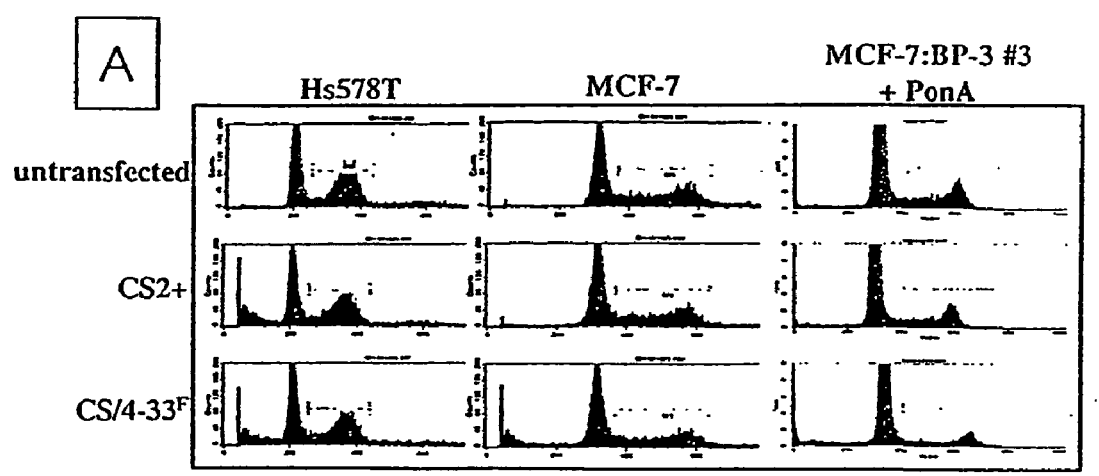
FIG. 8A shows a flow cytometic analysis of cells transfected with FLAG-tagged clone 4.33 vector (CS/4.33$^F$). Hs578T (IGFBP-3 expressing), MCF-7 (IGFBP-3 non-expressing) and induced MCF-7:BP-3, #3 cells were either untreated, or transiently transfected with control vector (CS2+) or with FLAG-tagged clone 4.33 vector (CS/4.33$^F$) for 24 hours. The cells were then harvested, and the DNA content/cell cycle profile was analyzed by propidium iodide staining followed by flow cytometric detection. In each case, the P4.33-transfected cells displayed an increase in the sub-G1 population and a concurrent decrease in the S/G2/M population compared to control cells.

Induction of Apoptosis by P4.33 and IGFBP-3 in Breast Cancer Cells; Flow Cytometry Breast cancer cells were transfected with control vector (CS2+) or with FLAG-tagged clone 4.33 vector (CS/4.33$^F$) to determine if P4.33 and IGFBP were involved in the induction of apoptosis. Specifically, Hs578T (IGFBP-3 expressing), MCF-7 (IGFBP-3 non-expressing) and induced MCF-7:BP-3, #3 cells were either untreated or transiently transfected with control vector (CS2+) or with FLAG-tagged clone 4.33 vector (CS/4.33$^F$) for 24 hours. The cells were then harvested, and the DNA content/cell cycle profile was analyzed by propidium iodide staining followed by flow cytometric detection. In each case, the P4.33-transfected cells displayed an increase in the sub-G1 population and a concurrent decrease in the S/G2/M population compared to control cells (FIG. 8A, and EXAMPLE 6, below). A peak in the sub-G1 range is indicative of cells undergoing apoptosis.

Figure 8B:
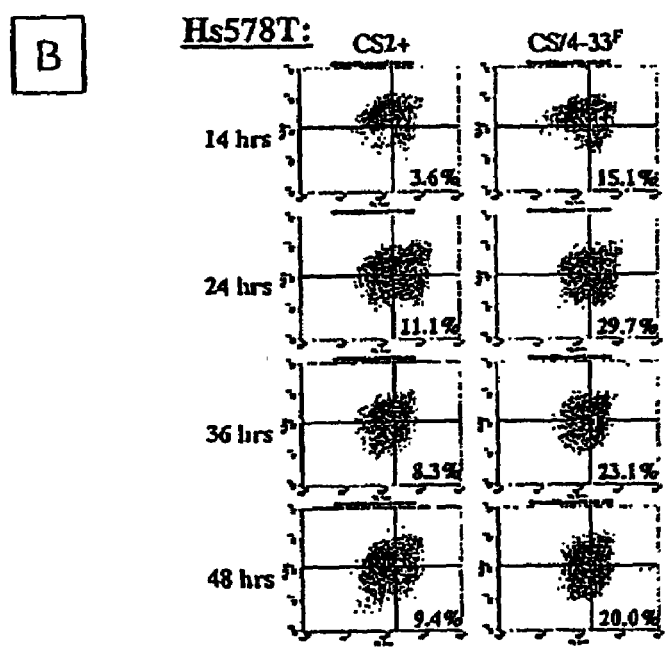
FIG. 8B shows that at various times after transient transfection of Hs578T cells with FLAG-tagged clone 4.33 vector (CS/4.33$^F$), the population of early apoptotic cells was significantly increased relative to control-transfected cells. Hs578T cells were transfected for various times with control vector (CS2+) or with FLAG-tagged clone 4.33 vector (CS/4.33$^F$). Harvested cells were incubated with FITC-labeled Annexin V, washed and then resuspended in propidium iodide staining solution. A two-color flow cytometry analysis was performed to discriminate between early apoptotic and late apoptotic/necrotic cells. At each time point, the population of early apoptotic cells was significantly increased in the cells transfected with P4.33, compared to control-transfected cells.

This apoptotic induction was further investigated using an Annexin V assay, which is an art-recognized assay used to identify cells early in the apoptotic process (FIG. 8B, and EXAMPLE 6). Briefly, by incubating suspended cells with FITC-labeled Annexin V, coupled with concurrent propidium iodide staining without permeabilization of the plasma membrane, it is possible to discriminate between cells in early apoptosis and those in late apoptosis or necrosis using a two-color flow cytometic analysis. The population of early apoptotic Hs578T cells was significantly increased in cells transfected for various lengths of time with P4.33, compared to control-transfected cells (FIG. 8B, and EXAMPLE 6).

Figure 9:
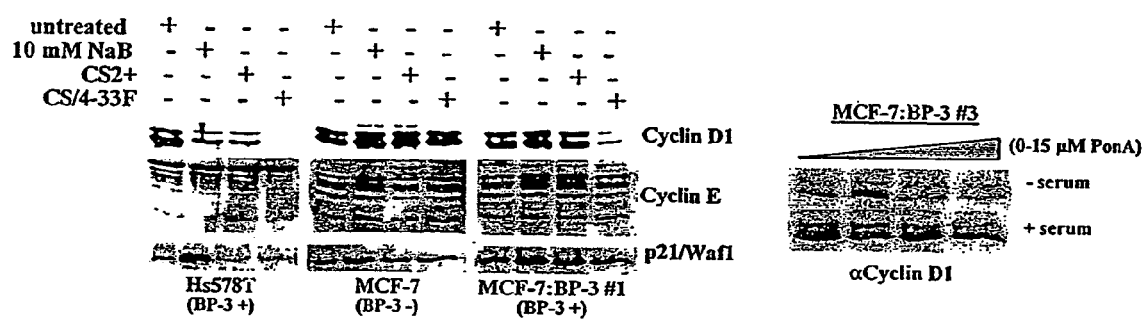
FIG. 9 shows that over-expression of P4.33 (IGFBP-3R) in cells that express IGFBP-3, or induction of IGFBP-3 in the inducible MCF-7:BP-3 #3 cell line, resulted in induction of apoptosis. Hs578T, MCF-7 and MCF-7:BP-3, #1 cells were left untreated, treated with sodium butyrate (NaB, an apoptotic inducer) or transiently transfected with control vector (CS2+) or with FLAG-tagged clone 4.33 vector (CS/4.33$^F$) for 24 hours. Cell lysates were then harvested, and assayed for protein content. Equal amounts of protein were electrophoresed and immunoblotted with antibodies against cell cycle regulatory proteins cyclin D1, cyclin E and p21/Waf1. Over-expression of P4.33 in the presence of IGFBP-3 resulted in a significant reduction in the levels of cyclin D1, which is required for cells to progress from G1 into S phase. No affect was seen on cyclin E or p21/Waf1. Proper upregulation of p21/Waf1 was seen with the control NaB treatment. Likewise, induction of IGFBP-3 in the inducible MCF-7:BP-3 #3 cell line, resulted in induction of apoptosis (right panel).

Induction of Apoptosis by P4.33 and IGFBP-3 in Breast Cancer Cells; Cell Cycle Markers An immunoblotting analysis using antibodies against cell cycle regulatory proteins cyclin D1, cyclin E and p21/Waf1 was used to determine if P4.33 induced apoptosis in cells expressing IGFBP-3. Transient overexpression of P4.33 in the presence of IGFBP-3 resulted in a significant reduction in the levels of cyclin D1, which is required for cells to progress from G1 into S phase (FIG. 9, and EXAMPLE 6, below). No affect was seen on cyclin E or p21/Waf1. Proper upregulation of p21/Waf1 was seen with the control NaB treatment.

This data, along with the flow cytometry data (FIGS. 8A and 8B), indicated that transient overexpression of P4.33 in cells that express IGFBP-3 resulted in induction of apoptosis in breast cancer cells.

Likewise, induction of IGFBP-3 in the inducible MCF-7:BP-3 #3 cell line, resulted in induction of apoptosis (FIG. 9, right panel), presumably mediated through endogenous P4.33.

Induction of Growth Inhibition and Apoptosis by Infection of Cancer Cells with a Recombinant Adenovirus P4.33 (IGFBP-3R) Expression Vector Additional embodiments of the present invention comprise adenovirus expression vectors and adenovirus gene transfer technology (EXAMPLE 7, below). Ad:IGFBP-3R, a recombinant adenovirus P4.33 expression vector, was constructed and used to over-express IGFBP-3 receptor (P4.33) in a variety of cancer cells, including human breast cancer cells (Hs578t, MDA231 and IGFBP-3 expressing MCF-7), prostate cancer cells (PC-3) and non-small cell lung carcinoma cells. Such over-expression of P4.33 resulted in substantial growth inhibition in human breast cancer cells (Hs578t and MDA231), prostate cancer cells (PC-3) and non-small cell lung carcinoma cells (H157) (FIGS. 10 and 11; EXAMPLE 7). Furthermore, the IGFBP-3R-induced growth inhibition was attributed to induction of apoptosis (a specific cell death process), as demonstrated by time-dependent increases of DNA fragmentation, and by significant increases of caspase-3 and -8 activities in these cells (FIGS. 12-18; EXAMPLE 7).

Generation of a Polyclonal Antibody and Subcellular Localization of P4.33 (IGFBP-3R)

A polyclonal antibody against P4.33 was generated to facilitate studies of endogenous P4.33 (FIG. 6, and EXAMPLE 4, below). The α-P4.33 polyclonal antiserum readily recognized a GST::P4.33 fusion protein, and cross-reactivity with unfused GST was low. Additionally, the α-P4.33 polyclonal antibody recognized a protein species of 32 kDa from Hs578T cell lysates, and this same protein species was seen in all other cell lines tested (FIG. 6, and EXAMPLE 4).

Figure 6A:
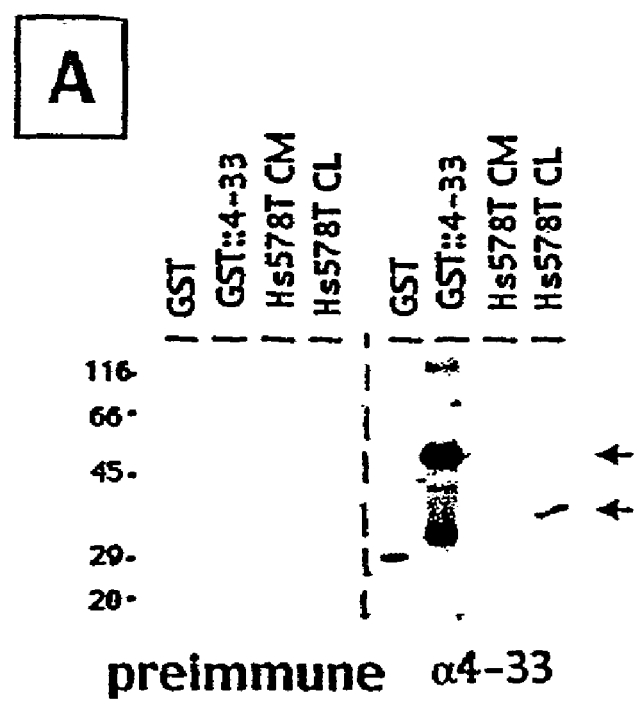
FIG. 6A shows a WIB analysis indicating that the α-P4.33 polyclonal antibody of the present invention readily recognized a GST::P4.33 fusion protein, a protein species of 32 kDa from Hs5778T and other cell lysates tested. The SDS-PAGE and WIB analysis was performed on samples corresponding to: purified unfused GST; GST::P4.33 fusion protein; Hs578T conditioned medium (CM) and Hs578T cell lysate (CL).
Figure 6B:
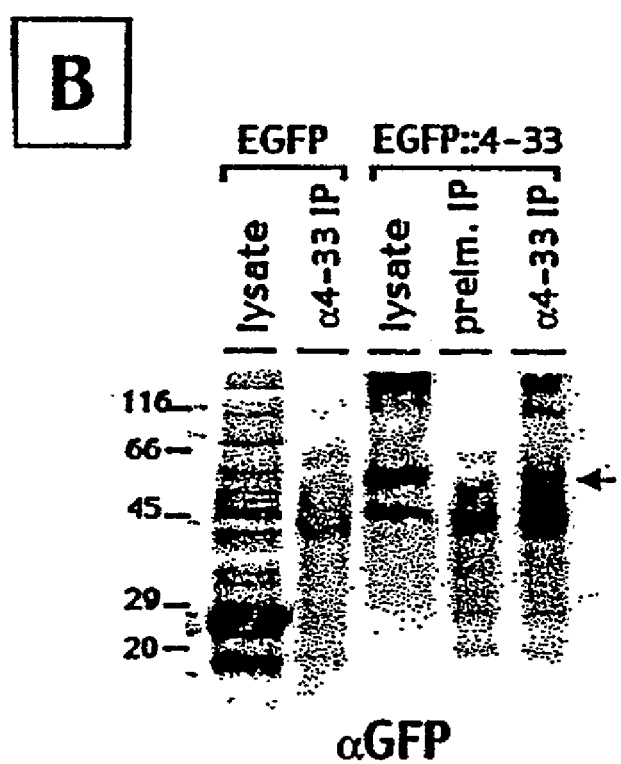
FIG. 6B shows an immunoprecipitation and WIB analysis indicating that the EGFP::P4.33 fusion protein, but not the unfused EGFP, was immunoprecipitated by the α-P4.33 polyclonal antibody of the present invention. No immunoprecipitation was seen with preimmune sera. COS-7 cells were transiently transfected with either an EGFP::P4.33 fusion protein vector or with a control vector. Lysates from these transfected cells were subjected to immunoprecipitation with either preimmune serum or α-P4.33 antibody plus Protein A sepharose, and then analyzed by reducing SDS-PAGE. Following transfer, WIB analysis was performed using α-GFP monoclonal antibody.

The α-P4.33 polyclonal antibody was tested in an immunoprecipitation assay using EGFP-fused P4.33. EGFP::P4.33 fusion protein, but not the unfused EGFP, was immunoprecipitated by the α-P4.33 polyclonal antibody (FIG. 6B, and EXAMPLE 4).

Figure 6C:
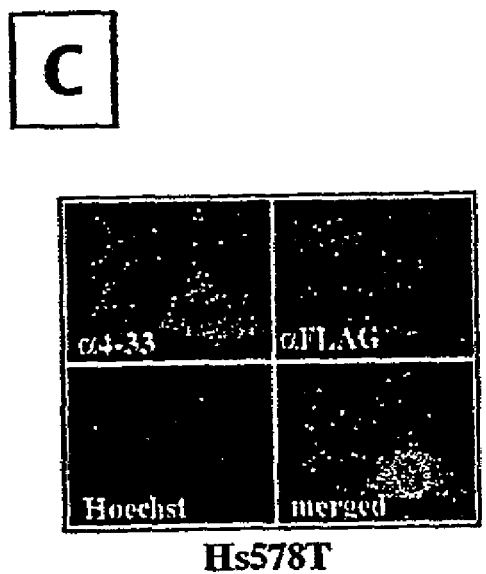
FIG. 6C shows that immunostaining with the α-P4.33 polyclonal antibody and α-FLAG M2 monoclonal antibody resulted in an identical fluorescent staining pattern, demonstrating that the α-P4.33 polyclonal antibody is functional for use in immunocytochemisty. Additionally, in adherent Hs578T adherent cells, P4.33 forms a distinct perinuclear ring with additional immunostaining apparent in the cytoplasm, and on the cell surface. Hs578T cells were transiently transfected with FLAG-tagged clone 4.33 for 36 hours. Cells were then fixed and dual immunostained with the α-P4.33 polyclonal antibody and α-FLAG M2 monoclonal antibody (green fluroscence), followed by α-mouse-FITC and α-rabbit-Texas Red secondary antibodies. Hoechst dye was used as a nuclear indicator. Confocal images from α-FLAG were overlaid onto images of α-P4.33 staining to generate a yellow color where overlapping green and red fluorescence was detected.

Additionally, the α-P4.33 polyclonal antibody was shown to be functional for use in immunocytochemisty. The localization of P4.33 protein in adherent and suspended breast cancer cells was readily apparent. In Hs578T adherent cells, P4.33 formed a distinct perinuclear ring with additional immunostaining apparent in the cytoplasm, and possibly on the cell surface (FIG. 6C, upper left quandrant, and EXAMPLE 4).

Figure 6D:
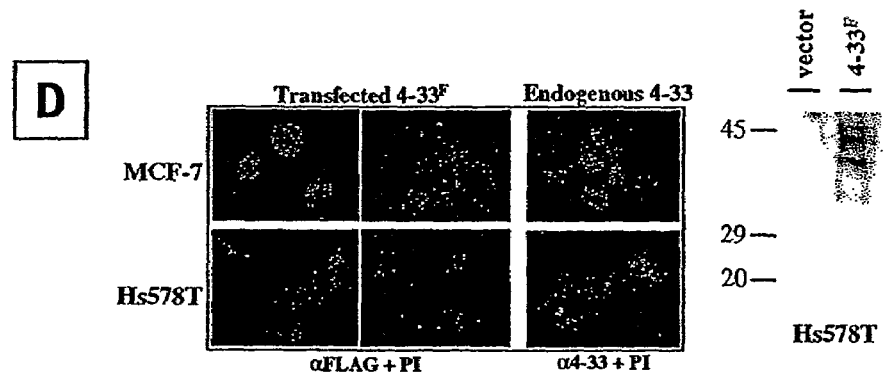
FIG. 6D shows that the cell surface localization of P4.33 protein in suspended MCF-7 and Hs578T breast cancer cells is readily apparent. Hs578T and MCF-7 cells were transiently transfected with FLAG-tagged clone 4.33. The cells were then trypsinized, washed, and the nuclei stained with propidium iodide. Cells were subsequently washed extensively, and incubated with either α-P4.33 polyclonal antibody or α-FLAG M2 monoclonal antibody, followed by incubation with α-mouse-FITC and α-rabbit-Texas Red secondary antibodies. Hoechst dye was used as a nuclear indicator. Cell surface staining is readily apparent. Both transfected P4.33$^F$ (detected with the α-FLAG M2 antibody), and endogenous P4.33 (detected with the α-P4.33 antibody) displayed a characteristic ring pattern around the surface of suspended cells. This same ring pattern was also seen in immunostained Sf9 insect cells infected with virus encoding P4.33$^F$. Furthermore, P4.33 was determined to be present in crude membrane preparations of Hs578T cells.

Immunostaining was also performed on cells in suspension to determine whether P4.33 was located on the cell surface. Both transfected P4.33$^F$ (detected with the α-FLAG M2 antibody), and endogenous P4.33 (detected with the α-P4.33 antibody) displayed a characteristic ring pattern around the surface of suspended MCF-7 and Hs578T breast cancer cells, indicative of cell-surface staining (FIG. 6D, and Example 4). This same ring pattern was also seen in immunostained Sf9 insect cells infected with virus encoding P4.33$^F$. Furthermore, P4.33 was determined to be present in crude membrane preparations from Hs578T cells (FIG. 6D, and Example 4).

Therefore, α-P4.33 antibodies, generated as part of the present invention, were shown to specifically immunoprecipitate a 32 kDa protein species from Hs578T, and from other cell lysates. Additionally, α-P4.33 polyclonal antibodies were functional for use in immunocytochemisty, and were used to determine that endogenous and transiently expressed P4.33 was localized on the cell surface, in the cytoplasm, and in a perinuclear pattern in both adherent and suspended cells. The α-P4.33 polyclonal antibodies were also used to detect P4.33 in crude membrane preparations. The α-P4.33 antibodies are therefore useful for specific recognition of, and binding to the IGFBP-3R receptor (P4.33).

P4.33 (IGFBP-3R) Proteins, Polypeptides, and Antibodies

P4.33 (IGFBP-3R) protein, polypeptides and peptide fragments, mutated, truncated or deleted forms of the P4.33 and/or P4.33 fusion proteins (designated P4.33::, or IGFBP-3::) can be prepared for a variety of uses, including but not limited to the generation of antibodies, as reagents in diagnostic assays, the identification of other cellular gene products involved in the regulation cancer, as reagents in assays for screening for compounds that can be used in the treatment cancer, and as pharmaceutical reagents useful in the treatment of cancer.

Production of P4.33 Polypeptides. The cDNA sequence encoding P4.33 is shown (SEQ ID NO:1), along with the corresponding deduced amino acid sequence (SEQ ID NO:2) (see also FIG. 2B, where a putative transmembrane domain, N-glycosylation sites, a leucine zipper motif and a cAMP-dependent phosphorylation site are denoted). Peptides corresponding to one or more domains of the P4.33 (e.g., transmembrane domain), truncated or deleted P4.33 (e.g., P4.33 in which one or more regions or domains have been deleted) as well as fusion proteins in which the full length P4.33, a P4.33 peptide or truncated P4.33 is fused to an unrelated protein are also within the scope of the invention (e.g., GST, FLAG and EGFP fusions described the Examples below). Such soluble peptides, proteins, fusion proteins, or antibodies (including anti-idiotypic antibodies) that bind to and "activate," "neutralize" or "mop-up" circulating natural ligand for the P4.33, can be used as described herein to treat cancer. To this end, peptides corresponding to individual domains of P4.33, soluble deletion mutants of P4.33, or the entire P4.33 can be fused to another polypeptide (e.g., an IgFc polypeptide, or eptitope tag) to produce fusion proteins (e.g., P4.33::IgFc polypeptide).

Such peptides, polypeptides, and fusion proteins can be prepared by recombinant DNA techniques well known in the art. For example, nucleotide sequences encoding one or more P4.33 regions or domains can be synthesized or cloned and ligated together to encode a soluble P4.33 polypeptide. The DNA sequence encoding one or more P4.33 regions or domains can be ligated together directly or via a linker oligonucleotide that encodes a peptide spacer. Such linkers may encode flexible, glycine-rich amino acid sequences thereby allowing the domains that are strung together to assume a conformation that can bind P4.33 ligands. Alternatively, nucleotide sequences encoding individual regions or domains can be used to express P4.33 peptides.

A variety of host-expression vector systems may be utilized to express nucleotide sequences encoding the appropriate regions of the P4.33 to produce such polypeptides. Where the resulting peptide or polypeptide is a soluble derivative the peptide, the polypeptide can be recovered from the culture media Where the polypeptide or protein is not secreted, the P4.33 product can be recovered from the host cell itself.

The host-expression vector systems also encompass engineered host cells that express the P4.33 or functional equivalents. Purification or enrichment of the P4.33 from such expression systems can be accomplished using appropriate methods well known to those skilled in the art. However, such engineered host cells themselves may be used in situations where it is important not only to retain the structural and functional characteristics of the P4.33, but also to assess biological activity, e.g., in drug screening assays.

The host-expression vector systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing P4.33 nucleotide sequences; yeast (e.g., *Saccharomyces, Pichia*) transformed with recombinant yeast expression vectors containing the P4.33 nucleotide sequences; insect cell systems infected with recombinant virus expression vectors (e.g., baculovirus) containing the P4.33 sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing P4.33 nucleotide sequences; or mammalian cell systems (e.g., COS, CHO, BHK, 293, 3T3, MCF-7, Hs578T) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the P4.33 gene product being expressed. For example, when a large quantity of such a protein is to be produced, for the generation of pharmaceutical compositions of P4.33 protein or for raising antibodies to the P4.33 protein, vectors that direct the expression of high levels of fusion protein products that are readily purified may be desirable. Such vectors include, but are not limited, to the *E. coli* expression vector pUR278 (Ruther et al., *EMBO J.* 2:1791, 1983), in which the P4.33 coding sequence may be ligated individually into the vector in frame with the lacZ coding region so that a fusion protein is produced; pIN vectors (Inouye & Inouye, *Nucleic Acids Res.* 13:3101-3109, 1985; Van Heeke & Schuster, *J. Biol. Chem.* 264: 5503-5509, 1989); and the like. PGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

Alternatively, utilizing an antibody specific for the fusion protein being expressed may readily allow for purification any fusion protein. For example, a system described by Janknecht et al. allows for the facile purification of non-denatured fusion proteins expressed in human cell lines (Janknecht, et al., *Proc. Natl. Acad. Sci. USA* 88:8972-8976, 1991). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$:nitriloacetic acid-agarose columns and histidine-tagged proteins are selectively eluted with imidazole-containing buffers.

*Autographa californica* nuclear polyhedrosis virus (AcNPV) can be used as a vector to express foreign genes in an insect system. The virus grows in *Spodoptera frugiperda* cells. The P4.33 coding sequence may be cloned individually into non-essential regions (e.g., the polyhedrin gene) of the virus and placed under control of an AcNPV promoter (e.g., the polyhedrin promoter). Successful insertion of P4.33 gene coding sequence will result in inactivation of the polyhedrin gene and production of non-occluded recombinant virus (i.e., virus lacking the proteinaceous coat coded for by the polyhedrin gene). The recombinant viruses are then used to infect cells in which the inserted gene is expressed (Smith et al., *J. Virol.* 46:584, 1983; Smith, U.S. Pat. No. 4,215,051).

In mammalian host cells, a number of viral-based expression systems may be utilized. In cases where an adenovirus or recombinanant adenovirus is used as an expression vector, the P4.33 nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the P4.33 gene product in infected hosts. (Logan & Shenk, *Proc. Natl. Acad. Sci. USA* 81:3655-3659, 1984). Specific initiation signals may also be required for efficient translation of inserted P4.33 nucleotide sequences. These signals include the ATG initiation codon and adjacent sequences. In cases where an entire P4.33 gene or cDNA, including its own initiation codon and adjacent sequences, is inserted into the appropriate expression vector, no additional translational control signals may be needed. However, in cases where only a portion of the P4.33 coding sequence is inserted, exogenous translational control signals, including, perhaps, the ATG initiation codon, must be provided. Furthermore, the initiation codon must be in frame with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (Bittner et al., *Methods Enzymol.* 153:516-544, 1987). Recombinant adenovirus-mediated expression of P4.33 (IGFBP-3R) is shown herein under EXAMPLE 7.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. Accordingly, eukaryotic host cells that possess cellular machinery for proper processing of the primary transcript, glycosylation, and phosphorylation of the P4.33 gene product may be used. Such mammalian host cells include, but are not limited to, CHO, VERO, BHK, HeLa, COS, MDCK, 293, 3T3, MCF-7, Hs578T and WI38 cell lines.

For long-term, high-yield production of recombinant proteins, stable expression is preferred. For example, cell lines that stably express the P4.33 sequences may be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for a period (e.g., 1-2 days) in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer stable cell lines that express the P4.33 gene product (e.g., the MCF-7:BP-3,#3 and #1 cell lines discussed in the EXAMPLES below). Such engineered cell lines may be particularly useful in screening and evaluation of compounds that affect the endogenous activity (e.g., signal transduction) of the P4.33 gene product.

A number of selection systems may be used, including but not limited to the herpes simplex virus thymidine kinase (Wigler et al., *Cell* 11:223, 1977), hypoxanthine-guanine phosphoribosyltransferase (Szybalska & Szybalski, *Proc. Natl. Acad. Sci. USA* 48:2026, 1962), and adenine phosphoribosyltransferase (Low, et al., *Cell* 22:817, 1980) genes can be employed in tk$^-$, hgprt$^-$ or aprt$^-$ cells, respectively. Also, anti-metabolite resistance can be used as the basis of selection for the following genes: dhfr, that confers resistance to methotrexate (Wigler et al., *Proc. Natl. Acad. Sci. USA* 77:3567, 1980; O'Hare et al., *Proc. Natl. Acad. Sci. USA* 78:1527, 1981); gpt, that confers resistance to mycophenolic acid (Mulligan & Berg, *Proc. Natl. Acad. Sci. USA* 78:2072, 1981); neo, that confers resistance to the aminoglycoside G-418 (Colberre-Garapin et al., *J. Mol. Biol.* 150:1, 1981); and hygro, that confers resistance to hygromycin (Santerre et al., *Gene* 30:147, 1984).

Antibodies to P4.33 Polypeptides. Antibodies that specifically recognize one or more epitopes of P4.33, or epitopes of conserved variants of P4.33, or peptide fragments of the P4.33 are also encompassed by the invention. Such antibodies include but are not limited to polyclonal antibodies (e.g., as described in EXAMPLE 4 below), monoclonal antibodies (mAbs), humanized or chimeric antibodies, single-chain antibodies, Fab fragments, F(ab')$_2$ fragments, fragments produced by a Fab expression library, anti-idiotypic (anti-Id) antibodies, and epitope-binding fragments of any of the above. The antibodies of the invention may be used, for example, in the detection of the P4.33 in a biological sample and may, therefore, be utilized as part of a diagnostic or prognostic technique whereby patients or tissue samples may be tested for abnormal amounts of P4.33. Such antibodies may also be utilized in conjunction with, for example, compound screening schemes, as described, above, for the evaluation of the effect of test compounds on expression and/or activity of the P4.33 gene product. Additionally, such antibodies can be used in conjunction with the gene therapy techniques described, below (e.g., to evaluate the normal and/or engineered P4.33-expressing cells prior to their introduction into the patient). Such antibodies may additionally be used as a method for the modulation of normal or abnormal P4.33 activity. Thus, such antibodies may, therefore, be utilized as part of cancer treatment methods.

For the production of antibodies, various host animals may be immunized by injection with the P4.33, an P4.33 peptide (e.g., one corresponding the a functional domain of the P4.33, such as the transmembrane, or extracellular domains, or IGFBP-3 interaction domain), truncated P4.33 polypeptides (P4.33 in which one or more domains, e.g., the transmembrane or IGFBP-3 interaction domain, has been deleted), functional equivalents of the P4.33 or mutants of the P4.33.

Such host animals may include but are not limited to rabbits, mice, hamsters and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals. Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (*Nature* 256: 495-497, 1975; and U.S. Pat. No. 4,376,110), the human B-cell hybridoma technique (Kosbor et al., *Immunology Today* 4:72, 1983; Cole et al., *Proc. Natl. Acad. Sci. USA* 80:2026-2030, 1983), and the EBV-hybridoma technique (Cole et al., *Monoclonal Antibodies And Cancer Therapy*, Alan R. Liss, Inc., pp. 77-96, 1985). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., *Proc. Natl. Acad. Sci. USA*, 81:6851-6855, 1984; Neuberger et al., *Nature*, 312: 604-608, 1984; Takeda et al., *Nature*, 314: 452-454, 1985) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region (humanized).

Alternatively, techniques described for the production of single-chain antibodies (U.S. Pat. No. 4,946,778; Bird, *Science* 242:423-426, 1988; Huston et al., *Proc. Natl. Acad. Sci. USA* 85:5879-5883, 1988; and Ward et al., Nature 334:544-546, 1989) can be adapted to produce single-chain antibodies against P4.33 gene products. Single-chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments, that can be produced by pepsin digestion of the antibody molecule; and the Fab fragments, that can be generated by reducing the disulfide bridges of the F(ab')$_2$ fragments. Alternatively, Fab expression libraries may be constructed (Huse et al., *Science*, 246:1275-1281, 1989) to allow rapid and easy identification of monoclonal Fab fragments with the desired specificity.

Antibodies to the P4.33 can, in turn, be utilized to generate anti-idiotype antibodies that "mimic" the P4.33, using techniques well known to those skilled in the art. (Greenspan & Bona, *FASEB J7* (5):437-444, 1993; and Nissinoff, *J. Immunol.* 147:2429-2438, 1991). For example antibodies that bind to the P4.33 and competitively inhibit the binding of IGFBP-3 to the P4.33 can be used to generate anti-idiotypes that "mimic" the P4.33 and, therefore, bind and neutralize IGFBP-3. Such neutralizing anti-idiotypes or Fab fragments of such anti-idiotypes can be used in cancer therapeutic regimens to neutralize the native ligand.

Alternatively, antibodies can be generated against P4.33 that can act as agonists of P4.33. Such antibodies will bind to the P4.33 and activate the signal transducing activity of P4.33 and/or IGFBP-3 or IGFBP-3:P4.33 complex.

In addition, antibodies that act as antagonist of P4.33 activity (i.e., inhibit the activation or signaling by P4.33) may be used to treat cancer.

Gene Therapy Approaches to Controlling P4.33 Activity and Treating Cancer

The expression of P4.33 can be controlled in vivo (e.g., at the transcriptional or translational level) using gene therapy approaches to regulate P4.33 activity and treat cancer. Certain approaches are described below.

Gene Replacement Therapy. With respect to an increase in the level of normal P4.33 gene expression and/or P4.33 gene product activity, P4.33 nucleic acid sequences can be utilized for the treatment of cancer, including lung, cervical, breast, colon or prostate carcinoma Where the cause of cancer is related to a defective P4.33 gene, treatment can be administered, for example, in the form of gene replacement therapy. Specifically, one or more copies of a normal P4.33 gene or a portion of the P4.33 gene that directs the production of an P4.33 gene product exhibiting normal function, may be inserted into the appropriate cells within a patient or animal subject, using vectors that include, but are not limited to adenovirus, adeno-associated virus, retrovirus and herpes virus vectors, in addition to other particles that introduce DNA into cells, such as liposomes.

Because the P4.33 gene is expressed in the brain, possibly including the cortex, thalamus, brain stem and spinal cord and hypothalamus, such gene replacement therapy techniques should be capable of delivering P4.33 gene sequences to these cell types within patients. Thus, the techniques for delivery of the P4.33 gene sequences should be designed to readily cross the blood-brain barrier, that are well known to those of skill in the art (PCT WO89/10134, which is incorporated herein by reference in its entirety), or, alternatively, should involve direct administration of such P4.33 gene sequences to the site of the cells in which the P4.33 gene sequences are to be expressed. In particular animals, targeted homologous recombination can be utilized to correct the defective endogenous P4.33 gene in the appropriate tissue; e.g., brain tissue. Targeted homologous recombination can be used to correct the defect in stem cells (ES) cells in order to generate offspring with a corrected trait.

Additional methods which may be utilized to increase the overall level of P4.33 gene expression and/or P4.33 activity include the introduction of appropriate P4.33-expressing cells, preferably autologous cells, into a patient at positions and in numbers which are sufficient to ameliorate the progression of cancer. Such cells may be either recombinant or non-recombinant. Among the cells which can be administered to increase the overall level of P4.33 gene expression in a patient are normal cells, or e.g., hypothalamus cells, that express the P4.33 gene. The cells can be administered at the anatomical site in the brain, or as part of a tissue graft located at a different site in the body. Such cell-based gene therapy techniques are well known to those skilled in the art (Anderson et al., U.S. Pat. No. 5,399,349; Mulligan & Wilson, U.S. Pat. No. 5,460,959). Finally, compounds, identified in the assays described herein, that stimulate or enhance the signal transduced by activated P4.33 (e.g., by activating downstream signaling proteins in the P4.33 signal transduction pathway) can be used to treat cancer. The formulation and mode of administration will depend upon the physico-chemical properties of the compound. The administration should include known techniques that allow for a crossing of the blood-brain barrier.

Inhibition of P4.33 Expression. In an alternate embodiment, cancer therapy can be designed to reduce the level of endogenous P4.33 gene expression, for example, by using antisense or ribozyme approaches to inhibit or prevent translation of P4.33 mRNA transcripts; triple helix approaches to inhibit transcription of the P4.33 gene; or targeted homologous recombination to inactivate or "knock out" the P4.33 gene or its endogenous promoter. Such gene therapy may be utilized for treatment of cancer, e.g. lung, cervical, breast, colon or prostate carcinoma. Because the P4.33 gene is expressed in the brain, in addition to many other tissues, delivery techniques should be preferably designed to cross the blood-brain barrier (PCT WO89/10134, which is incorporated by reference herein in its entirety). Alternatively, the antisense, ribozyme or DNA constructs described herein could be administered directly to the site containing the target cells.

Antisense approaches involve the design of oligonucleotides (either DNA or RNA) that are complementary to mRNA. The antisense oligonucleotides will bind to the complementary mRNA transcripts and prevent translation. Absolute complementarily, although preferred, is not required. A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

While antisense nucleotides complementary to the coding region sequence could be used, those complementary to the transcribed, untranslated region are most preferred. Oligonucleotides that are complementary to the 5' end of the message, e.g., the 5' untranslated sequence up to and including the AUG initiation codon, should work most efficiently at inhibiting translation (see SEQ ID NO:3-17). However, sequences complementary to the 3' untranslated sequences of mRNAs have been shown to be effective at inhibiting translation of mRNAs as well (Wagner, Nature 372:333-335, 1994). Thus, oligonucleotides complementary to either the 5'- or 3'-nontranslated, non-coding regions of P4.33 could most preferably be used in an antisense approach to inhibit translation of endogenous P4.33 mRNA. Oligonucleotides complementary to the 5' untranslated region of the mRNA should preferably include the complement of the AUG start codon. Antisense oligonucleotides complementary to mRNA coding regions are less efficient inhibitors of translation but could be used in accordance with the invention. Whether designed to hybridize to the 5'-, 3'- or protein coding region of P4.33 mRNA, antisense nucleic acids should be at least ten nucleotides in length, and are preferably oligonucleotides ranging from 10 to about 25 nucleotides in length. In specific aspects the oligonucleotide is at least 16 nucleotides, at least 17 nucleotides, or at least 21 nucleotides (see see SEQ ID NO:3-17).

Regardless of the choice of target sequence, it is preferred that in vitro studies are first performed to quantitate the ability of the antisense oligonucleotide to inhibit gene expression, it is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating or modulating transport across the cell membrane (Letsinger et al., Proc. Natl. Acad. Sci. USA 86:6553-6556, 1989; Lemaitre et al., Proc. Natl. Acad. Sci. USA 84:648-652, 1987; PCT WO88/09810, published Dec. 15, 1988) or the blood-brain barrier (PCT WO89/10134, published Apr. 25, 1988), or the nuclear membrane, and may include hybridization-triggered cleavage agents (Krol et al., BioTechniques 6:958-976, 1988) or intercalating agents. (Zon, Pharm. Res. 5:539-549, 1988). To this end, the oligonucleotide may be conjugated to another molecule, e.g., a peptide, hybridization-triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2 fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof. In yet another embodiment, the antisense oligonucleotide is an alpha-anomeric oligonucleotide. An alpha-anomeric oligonucleotide forms specific double-stranded hybrids with complementary RNA in which, contrary to the usual beta-units, the strands run parallel to each other (Gautier et al., *Nucl. Acids Res.* 15:6625-6641, 1987). The oligonucleotide is a 2'-O-methylribonucleotide (Inoue et al., *Nucl. Acids Res.* 15:6131-6148, 1987), or a chimeric RNA DNA analogue (Inoue et al., *FEBS Lett.* 215: 327-330, 1987).

Oligonucleotides of the invention may be synthesized by standard methods known in the art, e.g., by use of an automated DNA synthesizer (such as are commercially available from Biosearch, Applied Biosystems, etc.). As examples: phosphorothioate oligonucleotides may be synthesized by the method of Stein et al., *Nucl. Acids Res.* 16:3209, 1988; methylphosphonate oligonucleotides can be prepared by use of controlled pore glass polymer supports (Sarin et al., *Proc. Natl. Acad. Sci. USA* 85:7448-7451, 1988), etc. The antisense molecules should be delivered to cells that express the P4.33 in vivo, e.g., cancer or other cells and tissues. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically. However, it is often difficult to achieve intracellular concentrations of the antisense sufficient to suppress translation of endogenous mRNAs. Therefore, a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous P4.33 transcripts and thereby prevent translation of the P4.33 mRNA. For example, a vector can be introduced in vivo such that a cell takes it up, whereupon the vector directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Benoist and Chambon, *Nature* 290:304-310, 1981), the promoter contained in the 3' long terminal repeat of Rous sarcoma virus (Yamamoto et al., *Cell* 22:787-797, 1980), the herpes thymidine kinase promoter (Wagner et al., *Proc. Natl. Acad. Sci. USA* 78:1441-1445, 1981), the regulatory sequences of the metallothionein gene (Brinster et al., *Nature* 296:39-42, 1982). Any type of plasmid, cosmid, YAC or viral vector can be used to prepare the recombinant DNA construct that can be introduced directly into the tissue site; e.g., the tumor or other tissues. Alternatively, viral vectors can be used which selectively infect the desired tissue; (e.g., for brain, herpesvirus vectors may be used), in which case administration may be accomplished by another route (e.g., systemically).

Ribozyme molecules designed to catalytically cleave P4.33 mRNA transcripts can also be used to prevent translation of P4.33 mRNA and expression of P4.33. (PCT WO90/11364, published Oct. 4, 1990; Sarver et al., *Science* 247: 1222-1225, 1990). While ribozymes that cleave mRNA at site-specific recognition sequences can be used to destroy P4.33 mRNAs, the use of hammerhead ribozymes is preferred. Hammerhead ribozymes cleave mRNAs at locations dictated by flanking regions that form complementary base pairs with the target mRNA. The sole requirement is that the target "mRNA have the following sequence of two bases: 5'-UG-3". The construction and production of hammerhead ribozymes is well known in the art and is described more fully in Haseloff and Gerlach, *Nature,* 334:585-591, 1988. There are numerous potential hammerhead ribozyme cleavage sites within the nucleotide sequence of human P4.33 cDNA (see FIG. 2B, and SEQ ID NO:1). Preferably the ribozyme is engineered so that the cleavage recognition site is located near the 5' end of the P4.33 mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which have been described by Thomas Cech and collaborators (Zaug et al., *Science* 224:574-578, 1984; Zaug and Cech, *Science* 231: 470-475, 1986; Zaug et al., *Nature* 324:429433, 1986; WO 88/04300; Been and Cech, *Cell* 47:207-216, 1986). The Cech-type ribozymes have an eight base pair active site that hybridizes to a target RNA sequence whereafter cleavage of the target RNA takes place. The invention encompasses those Cech-type ribozymes that target eight base-pair active site sequences that are present in P4.33.

As in the antisense approach, the ribozymes can be composed of modified oligonucleotides (e.g., for improved stability, targeting, etc.) and should be delivered to cells that express the P4.33 in vivo, e.g., prostate, brain, liver, etc. A preferred method of delivery involves using a DNA construct "encoding" the ribozyme under the control of a strong constitutive pol III or pol II promoter, so that transfected cells will produce sufficient quantities of the ribozyme to destroy endogenous P4.33 messages and inhibit translation. Because ribozymes, unlike antisense oligonucleotides, are catalytic, a lower intracellular concentration is required for efficiency.

Endogenous P4.33 gene expression can also be reduced by inactivating or "knocking out" the P4.33 gene or its promoter using targeted homologous recombination (Smithies et al., *Nature* 317:230-234, 1985; Thomas & Capecchi, *Cell* 51:503-512, 1987; Thompson et al., *Cell* 5:313-321, 1989). For example, a mutant, non-functional P4.33 (or a completely unrelated DNA sequence) flanked by DNA homologous to the endogenous P4.33 gene can be used, with or without a selectable marker and/or a negative selectable marker, to transfect cells that express P4.33 in vivo. Insertion of the DNA construct, via targeted homologous recombination, results in inactivation of the P4.33 gene. Such approaches are particularly suited in the agricultural field where modifications to ES (embryonic stem) cells can be used to generate animal offspring with an inactive P4.33. However this approach can be adapted for use in humans provided the recombinant DNA constructs are directly administered or targeted to the required site in vivo using appropriate viral vectors, e.g., herpes virus vectors for delivery to brain tissue; e.g., the hypothalamus and/or choroid plexus.

Alternatively, endogenous P4.33 gene expression can be reduced by targeting deoxyribonucleotide sequences complementary to the regulatory region of the P4.33 gene (i.e., the P4.33 promoter and/or enhancers) to form triple helical structures that prevent transcription of the P4.33 gene in target cells in the body. (Helen, *Anticancer Drug Des.,* 6:569-84, 1991; Helene et al., *Ann, N.Y. Acad. Sci.,* 660:27-36, 1992; and Maher, *Bioassays* 14:807-15, 1992).

Screening Assays for Drugs Useful in Cancer Treatment

At least three different assay systems can be designed and used to identify compounds or compositions that modulate P4.33 activity or P4.33 gene expression, and therefore, modulate cancer. The systems described below may be formulated into kits. To this end, the P4.33 or cells expressing the P4.33 can be packaged in a variety of containers, e.g., vials, tubes, microtitre well plates, bottles, and the like. Other reagents can be included in separate containers and provided with the kit; e.g., positive controls samples, negative control samples, P4.33 peptides, buffers, cell culture media, antibodies, etc.

Cell-Based Assays. In accordance with the invention, a cell-based assay system can be used to screen for compounds that modulate the activity of the P4.33 to identify compounds for the treatment of cancer. To this end, cells that endogenously express P4.33 and/or IGFBP-3 can be used to screen for compounds. Alternatively, cell lines, such as 293 cells, COS cells, CHO cells, MCF-7 cells, Hs578T cells, fibroblasts, and the like, genetically engineered to express P4.33 and/or IGFBP-3 can be used for screening purposes. Preferably, host cells genetically engineered to express a functional P4.33 that either responds to activation by IGFBP-3 or IGFBP-3 peptides, or that activates IGFBP-3 or IGFBP-3 peptides, can be used as an endpoint in the assay; e.g., as measured by a chemical, physiological, biological, or phenotypic change, induction of a host cell gene or a reporter gene, change in cAMP levels, adenylyl cyclase activity, host cell G-protein activity, caspase activation, extracellular acidification rate, host cell kinase activity, proliferation, differentiation, etc.

To be useful in screening assays, the host cells expressing functional P4.33 and/or IGFBP-3 should give a significant P4.33-based response to, preferably greater than 5-fold induction over background. Host cells should preferably possess a number of characteristics, depending on the readout, to maximize the P4.33-based inductive response.

For example, for detecting induction of a CRE "reporter" gene as part of a reporter gene-based assay, a set of assay conditions comprising: (a) a low natural level of cAMP, (b) a high level of adenylyl cyclase, (c) a high level of protein kinase A, (d) a low level of phosphodiesterases, and (e) a high level of cAMP response element binding protein is advantageous. In addition, alternative pathways for induction of the CRE reporter are eliminated to reduce basal levels.

To increase P4.33-based responses, host cells are engineered to express a greater amount of favorable factors (e.g., enhanced or constitutive IGFBP-3 when screening for compounds that act as P4.33 antagonists) or a lesser amount of unfavorable factors (e.g., enhanced P4.33 expression when screening for P4.33 agonists).

In utilizing such cell systems, the cells expressing the P4.33 and/or IGFBP-3 are exposed to a test compound or controls. After exposure, the cells can be assayed to measure the expression and/or activity of components of the signal transduction pathway of P4.33 and/or IGFBP-3, or the activity of the signal transduction pathway itself can be assayed. For example, after exposure, cell lysates can be assayed for induction of cAMP, modulation of Ras, PKA, RAP1, B-Raf, Mek, or MAPK, caspase activation, or apoptosis. In screening for compounds that may act as agonists of P4.33, it may be advantageous to use cell lines that express little or no IGFBP-3 to test for activation of signal transduction by the test compound as compared to controls. In screening for compounds that may act as antagonists of P4.33, it may be advantageous to overexpress IGFBP-3 to test for inhibition of signal transduction by the test compound as compared to controls.

P4.33 has been shown herein, to undergo IGFBP-3 mediated intracellular nuclear transport (EXAMPLE 3 and FIG. 6). In another embodiment of the invention, test compounds are selected based on their ability to regulate nuclear translocation of P4.33 and/or IGFBP-3 or IGFBP-3:P4.33 complex.

Non-Cell-Based Assays. In addition to cell-based assays, non-cell-based assay systems may be used to identity compounds that interact with, e.g., bind to P4.33 or to IGFBP-3: P4.33 complex. Such compounds may act as agonists or antagonists of P4.33 or IGFBP-3 activity and may be used in the treatment of cancer. Soluble P4.33 may be recombinantly expressed and utilized in non-cell based assays to identify compounds that bind to P4.33 or to the IGFBP-3:P4.33 complex. Recombinantly expressed P4.33 polypeptides or fusion proteins can be used in the non-cell based screening assays, with or without IGFBP-3 polypeptides or fusion proteins. Alternatively, peptides corresponding to one or more P4.33 domains, or fusion proteins containing one or more of the P4.33 domains can be used in non-cell based assay systems to identify compounds that bind to P4.33 or to IGFBP-3:P4.33 complex. Such compounds may be useful to modulate the signal transduction pathway of P4.33 or IGFBP-3. In non-cell based assays the recombinantly expressed P4.33 polypeptide or fusion protein, or IGFBP-3:P4.33 complex, may be attached to a solid substrate such as a test tube, microtitre well or a column, by means well known to those in the art. The test compounds are then assayed for their ability to bind to the P4.33 or IGFBP-3:P4.33 complex.

In one aspect of the invention the screens may be designed to identify compounds that mimic the interaction between P4.33 and P4.33 ligands such as IGFBP-3. In such screens, the test compounds are labeled (e.g., radioactive, fluorescent, phosphorescent, etc.), and can be assayed for their ability to bind to P4.33. In another aspect of the invention the screens may be designed to identify compounds that antagonize the interaction between P4.33 and P4.33 ligands such as IGFBP-3. In such screens, the P4.33 ligands (i.e., IGFBP-3) are labeled and test compounds can be assayed for their ability to antagonize the binding of labeled ligand to P4.33.

Assays for Compounds or Compositions That Modulate Expression of the P4.33. In vitro cell based assays may be designed to screen for compounds that regulate P4.33 expression at either the transcriptional or translational level. To identify compounds that regulate P4.33 translation, cells or in vitro cell lysates containing P4.33 transcripts may be tested for modulation of P4.33 mRNA translation. To assay for inhibitors of P4.33 translation, test compounds are assayed for their ability to modulate the translation of P4.33 mRNA in in vitro translation extracts.

Compounds that increase the level of P4.33 expression, either at the transcriptional or translational level, may be useful for treatment of some forms of cancer. In contrast, those compounds that decrease the expression of P4.33 may be useful for treatment of other forms of cancer.

Compounds that can be Screened in Accordance with the Invention

The assays described above can identify compounds that affect P4.33 or IGFBP-3:P4.33 complex activity. For example, compounds that affect P4.33 or IGFBP-3:P4.33 complex activity include but are not limited to compounds that bind to the P4.33, inhibiting or not inhibiting binding of the natural ligand (IGFBP-3), and either activate signal transduction (agonists) or block activation (antagonists), and compounds that bind to the natural ligand of P4.33 and neutralize or enhance ligand activity. Compounds that affect P4.33 gene activity (by affecting P4.33 gene expression, including molecules, e.g., proteins or small organic molecules, that affect transcription or interfere with splicing events so that expression of the full-length or the truncated form of P4.33 can be modulated) can also be identified on the screens of the invention. However, it should be noted that the assays described can also identify compounds that modulate P4.33 signal transduction (e.g., compounds which affect downstream signaling events, such as inhibitors or enhancers of G protein activities, or of, e.g., Ras, PKA, RAP1, B-Raf, Mek, or MAPK, which may participate in transducing the signal activated by IGFBP-3 binding to the P4.33). The identification and use of such compounds that affect signaling events downstream of P4.33 and thus modulate effects of P4.33 on the cancer progression are within the scope of the invention.

The compounds which may be screened in accordance with the invention include, but are not limited to peptides, antibodies and fragments thereof, and other organic compounds (e.g., peptidomimetics) that bind to P4.33 or IGFBP-3:P4.33 complex and either mimic the activity triggered by IGFBP-3 (i.e., agonists) or inhibit the activity triggered by IGFBP-3 (i.e., antagonists); as well as peptides, antibodies or fragments thereof, and other organic compounds that include mutant or truncated P4.33 molecules (or a portion thereof) and that bind to and "activate" or "neutralize" IGFBP-3. Compounds may include, but are not limited to, peptides such as, for example, soluble peptides, including but not limited to members of random peptide libraries; (Lam et al., *Nature* 354:82-84, 1991; Houghten et al., *Nature* 354:84-86, 1991), and combinatorial chemistry-derived molecular library made of D- and/or L-configuration amino acids, phosphopeptides (including, but not limited to, members of random or partially degenerate, directed phosphopeptide libraries; e.g., Songyang et al., *Cell* 72: 67-778, 1993), antibodies (including, but not limited to, polyclonal, monoclonal, humanized, anti-idiotypic, chimeric or single chain antibodies, and FAb, $F(ab')_2$ and FAb expression library fragments, and epitope-binding fragments thereof), and small organic or inorganic molecules. Other compounds which can be screened in accordance with the invention include, but are not limited to, small organic molecules that are able to cross the blood-brain barrier, gain entry into an appropriate cell and affect the expression of the P4.33 gene or some other gene involved in the P4.33 signal transduction pathway (e.g., by interacting with the regulatory region or transcription factors involved in gene expression); or such compounds that affect the activity of P4.33 or the activity of some other intracellular factor involved in the P4.33 signal transduction pathway, such as, e.g., IGFBP-3, Ras, PKA, RAP1, B-Raf; Mek, or MAPK.

Computer modeling and searching technologies permit identification of compounds, or the improvement of already identified compounds, that can modulate P4.33 expression or activity. Having identified such a compound or composition, the active sites or regions are identified. Such active sites might typically be ligand-binding sites. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three-dimensional geometric structure of the active site is determined. This can be done by known methods, including X-ray crystallography, which can determine a complete molecular structure. On the other hand, solid or liquid phase NMR can be used to determine certain intramolecular distances. Any other experimental method of structure determination can be used to obtain partial or complete geometric structures. The geometric structures may be measured with a complexed ligand, natural or artificial, which may increase the accuracy of the active site structure determined.

Finally, having determined the structure of the active site, either experimentally, by modeling, or by a combination of approaches, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential P4.33 modulating compounds.

Alternatively, these methods can be used to identify improved modulating compounds from an already known modulating compound or ligand. In this manner, systematic variations in composition, such as by varying side groups, can be quickly evaluated to obtain modified modulating compounds or ligands of improved specificity or activity.

Compounds identified via assays such as those described herein may be useful, for example, in further elaborating the biological function of the P4.33 gene product, and for treating cancer. Assays for testing the efficacy of compounds identified in the cellular screen can be tested in cell-based or animal model systems. Such animal models may be used as test substrates for the identification of drugs, pharmaceuticals, therapies and interventions which may be effective in treating such disorders. For example, animal models may be exposed to a compound, suspected of exhibiting an ability to treat cancer, at a sufficient concentration and for a time sufficient to elicit such cancer treatment in the exposed animals. The response of the animals to the exposure may be monitored by assessing the reversal of cancer.

Delivery of Soluble P4.33 or Igfbp-3 Polypeptides

Genetically engineered cells that express soluble P4.33 domains, or IGFBP-3 domains, or fusion proteins thereof, e.g., fusion Ig molecules or $P4.33^{HA}$ or IGFBP-3 $^{HA}$ can be administered in vivo where they may function as "bioreactors" that deliver a supply of the soluble molecules. Such soluble P4.33 or IGFBP-3 polypeptides and fusion proteins, when expressed at appropriate concentrations, could activate endogenous P4.33 activity, or could neutralize, "mop up," or "activate," as the case may be, the native ligand for P4.33 (i.e., IGFBP-3) and thus act as modulators of P4.33 activity for cancer treatment purposes.

Pharmaceutical Formulations and Methods OF Treating Cancer

The invention encompasses methods and compositions for treating cancer. Because enhancement of P4.33 gene product function in the presence of IGFBP-3 results, in growth inhibition and cell death (apoptosis) (see EXAMPLES 5, 6 and 7 below) enhancement of P4.33 activity in such cells would facilitate progress in treating cancers such as, e.g., lung, cervical, breast, colon or prostate carcinomas. Alternatively, progression of certain cancers may be facilitated by higher than normal levels of P4.33 gene expression, and/or P4.33 gene activity. In these cases, down regulating activity of the P4.33 pathway (e.g., by targeting downstream signaling events) may be useful in treating cancer. Different approaches are discussed. Agonists of P4.33 can be used to induce apoptosis in certain cancers such as, e.g., lung, cervical, breast, colon or prostate carcinomas. Antagonists of P4.33 activity may also be useful in these or other cancer types. It is not necessary that the compound demonstrate absolute specificity for the P4.33.

For example, compounds that agonize both P4.33, and other unknown IGFBP-3 interaction molecules, could be used. Such compounds could be administered so that delivery to breast tissue, the prostate, or elsewhere, is optimized to achieve cancer treatment, and potential side effects may well be tolerated. Compounds that do not demonstrate a specificity for P4.33 can be administered in conjunction with another therapy or drug to control the side-effects that may result from modulating other molecules (e.g., other IGFBP-BPs); however, compounds which demonstrate a preference or selectivity for P4.33 or IGFBP-3:P4.33 complex are preferred.

Dose Determinations. Toxicity and therapeutic efficacy of such compounds can be determined by standard pharmaceutical and toxicologic procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Formulations and Use. Pharmaceutical compositions for use in accordance with the present invention may be formulated in a conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral or rectal administration. For oral administration, the pharmaceutical compositions' may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulary agents such as suspending, stabilizing and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long-acting formulations may be administered by implantation (for example subcutaneously or intramuscularly) or by intramuscular injection. Thus, for example, the compounds may be formulated with suitable polymeric or hydrophobic materials (e.g., as an emulsion in an acceptable oil) or ion-exchange resins, or as sparingly soluble derivatives, for example, as a sparingly soluble salt.

The compositions may, if desired, be presented in a pack or dispenser device that may contain one or more unit dosage forms containing the active ingredient. The pack may, for example, comprise metal or plastic foil, such as a blister pack. The pack or dispenser device may be accompanied by instructions for administration.

EXAMPLE 1

Cloning of a cDNA for a Novel IGFBP-3 Interacting Protein, P4.33

The following example of the present invention describes the cloning and isolation of clone 4.33, a cDNA encoding a novel IGFBP-3 interacting protein. The results show the discovery of a novel cDNA, 915 bp in length (SEQ ID NO:1), encoding a novel 240 amino acid protein (SEQ ID NO:2) that contains several N-glycosylation sites, a cAMP-dependent phosphorylation site, a single leucine-zipper motif (LZ), and a putative transmembrane domain near the C-terminus. See FIG. 2C.

Material and Methods

Yeast two-hybrid screen. An Hs578T cDNA library in pGAD10 was generated using the Two-Hybrid cDNA Library Construction Kit (Clontech). The "bait" plasmid was constructed by amplifying an internal sequence of the IGFBP-3 cDNA (encoding amino acids 88-148) by PCR, then cloning this fragment into the pBTM116 vector, in frame with the LexA DNA binding domain coding sequence. The bait plasmid was then transformed into yeast strain L40. A single transformant colony was selected for successive transformation with the pGAD10:Hs578T cDNA library. A total of 663 transformant colonies, that grew on selective media, were replica-plated onto duplicate fresh plates, one of which was used for a β-galactosidase assay. Positive colonies were then cultured on non-selective media until the bait plasmid was lost, and further tested in mating assays with the original bait strain and a false-positive screening strain expressing the pBTM116:lamin plasmid. Three colonies tested positive with the IGFBP-3 bait and negative with lamin. Plasmid DNA was isolated from these and transformed into E. coli TG1.

Northern blotting. The Human Multi-Tissue Northern Blots I & II were purchased from Clontech. Total RNAs from monolayer cultures of human breast and prostate cells were harvested using the RNeasy RNA isolation kit (Qiagen). Briefly, 5 µg quantities of total RNA from each cell line were run on 1% formaldehyde gels and transferred onto Gene-Screen Plus nylon membranes (NEN). Membranes were then UV crosslinked and stained in 0.02% methylene blue/0.3 M NaOAc, pH 5.5. [$^{32}$P]-labelled cDNA probes were prepared using the Prime IT II kit (Stratagene). Membranes were hybridized in Rapid-Hyb buffer (Amersham Pharmacia), washed in 0.3×SSC, and exposed to film.

Results

Isolation of Novel cDNA Clone using The Yeast-Two-Hybrid System. A novel cDNA, clone 4.33, was isolated using the yeast two-hybrid system. FIG. 1 shows a schematic diagram of the yeast-two-hybrid method used to isolate the IGFBP-3 interacting protein cDNA clone, 4.33. Briefly, five µg of total RNA from Hs578T human breast cancer cells was used to make a cDNA library fused to the GAL4 transcriptional activation domain employing the "MATCH MAKER™" Yeast-Two-Hybrid cDNA construction Kit (Clontech). This "Prey" library was used with a "Bait" construction comprised of the mid-region fragment of the IGFBP-3 cDNA, encoding amino acids 88-148 of IGFBP-3, fused to the Lex DNA binding domain (i.e., "Lex::BP-3$^{INT}$"), with the Match Maker Yeast-Two-Hybrid screening kit to isolate three independent positive colonies on selective media, as described under "Material and methods" above. Upon sequencing, it was discovered that two of the sequences matched sequences in the GenBank database: (1) Eps8, epidermal growth factor receptor kinase substrate; and (2) GRP78/BiP, glucose regulated stress protein, or human immunoglobulin heavy chain binding protein.

The third sequence, clone 4.33, was novel. The full-length 4.33 cDNA clone was confirmed using a "5' RACE rapid amplification of 5' kit" (Life Technologies) and a gene-specific primer for clone 4.33. Standard restriction enzyme digestion and subcloning technology was used to isolate the full-length 4.33 cDNA clone.

Discovery of a Novel cDNA and Protein Sequence. FIG. 2C shows the sequence of the novel 4.33 cDNA clone (SEQ ID NO:1). The 4.33 cDNA clone was sequenced to reveal a 915 bp cDNA with a translational start site (ATG, bold face) 37 bases from the 5' end, and a translational stop codon (TGA, bold face) delimiting an open-reading frame coding for 240 amino acids. The novel P4.33 protein (SEQ ID NO:2) has a predicted molecular weight of 26 kDa. It is leucine rich (19% by weight), has several potential glycosylation sites, a cAMP-dependent phosphorylation site, a single leucine zipper motif (LZ) and a putative transmembrane domain near the C-terminus (see lower portion of FIG. 2C). A "BLAST" search of known data bases through the National Center of Biotechnology Institute ("NCBI") revealed that the sequence was novel, and (until the present invention) of unknown function.

Distribution of P4.33 mRNA in Human Tissues and Cell Lines. FIGS. 2A and 2B show a Northern blot analysis of P4.33 mRNA expression. Human multiple tissue Northern blots (Clontech, I & II) with 2 µg of mRNA per lane, and Northern blots containing total RNAs from Hs578T and MCF-7 human breast cancer cell lines and human mammary epithelial cells (HMEC) were probed with [$^{32}$P]-α-dCTP labeled clone 4.33 cDNA. Samples contained in lanes 1-16 were as follows: Lane 1, heart; Lane 2, Brain; Lane 3, placenta; Lane 4, lung; Lane 5, liver; Lane 6, skeletal muscle; Lane 7, kidney; Lane 8, pancreas; Lane 9, spleen; Lane 10, thymus; Lane 11, prostate; Lane 12, testis; Lane 13, ovary; Lane 14, small intestine; Lane 15, colon; Lane 16, peripheral blood leukocyte.

Messenger RNA corresponding to clone 4.33 is found a wide distribution of human tissues, and in breast and prostate cancer cell lines. A 915 nucleotide mRNA was detected to varying degrees in all cell lines and tissues tested. A second roughly 2 kb transcript was detected in testis (Lane 12).

FIG. 2B shows that P4.33 appears to be differentially expressed in normal vs. cancerous human cell lines. Northern blots containing total RNAs from LNCaP and PC-3 human prostate cancer cells lines and human prostate epithelial cells (HPEC), Hs578T and MCF-7 human breast cancer cell lines an human mammary epithelial cells (HMEC) were probed with labeled clone 4.33 cDNA. The upper graph represents relative expression based on densitometric scans, normalized against 18S rRNA levels.

Most significantly, a dramatic decrease in endogenous P4.33 expression is seen in PC-3 prostate cancer cells (FIG. 2B).

EXAMPLE 2

Cellular Localization of EGFP::4.33 Fusion Protein, and Cellular Colocalization and Co-Immunoprecipitation of IGFBP-3 and Clone 4.33

According to the present invention, the interaction between IGFBP-3 and clone 4.33 was confirmed by immunocytochemistry (FIG. 3A) and in coimmunoprecipitation studies (FIG. 3B). COS-7 cells were transiently transfected with or without constructs encoding an EGFP::4.33 fusion protein and FLAG-tagged IGFBP-3 (IGFBP-3$^F$).

Material and Methods

Immunocytochemistry. Cells were seeded in 8-chamber culture slides (Nunc) and transfected at 70-80% confluency. After 48 hours, adherent cells were washed with PBS, fixed in 4% paraformaldehyde for 10 minutes at room temperature, and washed a further 3 times with PBS. Cells were then incubated in blocking solution (1% normal goat serum in PBS, 0.1% Triton X-100) for 1 hour at room temperature, followed by incubation with primary antibody diluted 1:1000 in blocking solution for 1-2 hours at room temperature. Cells were washed with PBS and incubated in fluorescently-conjugated secondary antibody diluted 1:1000+Hoechst stain in blocking solution for 1 hour at room temperature in the dark. Final washes in PBS were performed, and cells were subsequently covered with 50% glycerol and coverslipped. For suspended cell analysis, cells were trypsinized, washed in PBS, and stained beginning at the blocking step in a microfuge tube with constant gentle agitation. Following the final washes, cells were dispensed into chamber slides for visualization.

Immunoprecipitations. Cell lysates were diluted in 20 mM Tris, pH 7.6, 150 mM NaCl and adjusted to a final concentration of 0.5% Triton X-100. Antibodies were added (2 µl of polyclonal sera, or 1 µg of monoclonal antibody) followed by the addition of Protein A Fast Flow sepharose (Amersham Pharmacia) or Anti-mouse IgG agarose (Sigma). Immunoprecipitation reactions were incubated at 4° C. for 4 hours—overnight, then twice washed in 1 mL IP buffer and suspended in 1×reducing sample buffer for subsequent immunoblotting.

Plasmids, Recomdinant Proteins and Antibodies. pEGFP::IGFBP-3R was generated by subcloning the IGFBP-3R cDNA into pEGFP-N3 (Clontech) in frame with EGFP. CS/IGFBP-3R$^F$ was generated by first adding the FLAG peptide (DYKDDDK) coding sequence to the 3' end of the IGFBP-3R cDNA using PCR, then subcloning the product into the CS2+ mammalian expression vector.

Antibodies. Anti-FLAG M2 monoclonal antibody was from Sigma. Anti-cyclin D1 monoclonal antibody was from NeoMarkers/LabVision. Anti-Rb antibody was from BD-PharMingen. Donkey anti-rabbit and sheep anti-mouse HRP-conjugated secondary antibodies were from Amersham Pharmacia. Goat anti-mouse IgG$_1$ and goat anti-mouse IgG$_{2a}$ fluorescently-conjugated secondary antibodies were from Southern Biotechnology Associates. Goat anti-mouse IgG and goat anti-rabbit IgG fluorescently conjugated secondary antibodies were from Molecular Probes.

Results

Subcellular localization of EGFP::4.33 fusion protein. FIG. 3A shows that EGFP::4.33 fusion protein exhibits a perinuclear, diffusely cytoplasmic, and possibly extracellular localization pattern, and that it colocalized with transfected IGFBP-3. The upper panel of FIG. 3A shows COS-7 cells that were transiently transfected with unfused EGFP or EGFP fused to clone 4.33 (EGFP::4.33). Cells transfected with the EGFP::4.33 fusion protein exhibited a perinuclear, diffusely cytoplasmic, and possibly extracellular localization pattern upon staining with anti-GFP antibody, as compared to the nuclear plus cytoplasmic localization pattern in the case of cells transfected with unfused EGFP. Plasmids encoding clone 4.33 with EGFP fused at the 5' or 3' end of the cDNA gave identical results. This same subcellular localization pattern was observed in transiently transfected Hs578T and MCF-7 human breast cancer cells.

The lower panel of FIG. 3A shows COS-7 cells transiently transfected with both EGFP::4.33 and FLAG-tagged IGFBP-3 (IGFBP-3$^F$). The Co-transfected cells were then immunostained with either the M2 anti-FLAG antibody (α-BP-3) (red staining; left field), α-GFP antibody (green staining; middle field) or both antibodies. The EGFP::4.33 and IGFBP-3$^F$ expressed proteins appeared to colocalize in the cytoplasm and possibly cell membrane and extracellular matrix, indicated by the merging of green and red staining to yield yellow (right field). Hoechst dye was used a nuclear indicator.

Co-immunoprecipitation of IGFBP-3 and clone 4.33. FIG. 3B shows that EGFP::4.33 and IGFBP-3$^F$ immunoprecipitated together from lysates of COS-7 cells transiently co-transfected with EGFP::4.33 and IGFBP-3$^F$. Specifically, COS-7 cells were transiently transfected for 36 hours with expression constructs for EGFP, EGFP::4.33 and/or IGFBP-3$^F$ as indicated in the upper portion of FIG. 3B. The cell lysates were then harvested and precleared with anti-mouse IgG sepharose. Precleared lysates were then separately immunoprecipitated with either α-FLAG M2 affinity beads (i.e., IP: α-FLAG M2; see middle portion of FIG. 3B), or α-GFP monoclonal antibody plus anti-mouse IgG sepharose (i.e., IP: α-GFP; see lower portion of FIG. 3B) and equal protein concentrations subjected to reducing SDS-PAGE and western immunoblotting (WIB) analysis. WIB was performed using the opposing antibody; i.e., α-GFP (middle portion of FIG. 3B) or α-IGFBP-3 polyclonal antibody (lower portion of FIG. 3B).

The EGFP::4.33 and IGFBP-3$^F$ proteins immunoprecipitated together in both cases, with no interaction seen in control samples, demonstrating specific stable interaction between these proteins in a mammalian cell system.

The interaction of IGFBP-3$^F$ and EGFP::P4.33 (IGFBP-3R) was evident, and could be demonstrated whether anti-EGFP or anti-FLAG M2 antibody was used for the immunoprecipitation reaction. IGFBP-3$^F$ did not interact with unfused EGFP. For the western ligand blot assay, radiolabelled IGFBP-3 was used to detect binding with FLAG-tagged IGFBP-3R (IGFBP-3R$^F$) that had been immunoprecipitated from cell lysates with anti-FLAG M2 agarose beads, eluted with excess FLAG peptide, and western blotted. An anti-FLAG M2 immunoblot revealed the IGFBP-3R$^F$ as a doublet of roughly 32 and 34 kilodaltons. The membrane was then stripped and incubated with the $^{125}$I-labelled IGFBP-3, which bound to both the 32 and 34 kDa species. These results demonstrate the specific interaction of IGFBP-3 and IGFBP-3R in a mammalian system.

EXAMPLE 3

Cellular Overexpression of Clone 4.33 Resulted in Increased Specific IGFBP-3 Cell-Surface Binding, and Co-Translocation to the Nucleus According to the present invention, the binding of $^{125}$I-labelled IGFBP-3 to cells previously transfected with clone 4.33 was measured to determine whether the resulting expressed P4.33 could facilitate specific binding of IGFBP-3 to the cells (FIG. 4A).

Material and Methods

Cell culture, transfection, cell lysates, membrane preps. All cell lines, except the MCF-7:BP-3 stable lines, were purchased from ATCC. All were cultured in DMEM/high glucose with 10% fetal bovine serum. MCF-7:BP-3 stable lines were generated from wild type MCF-7 cells using the Ecdysone-inducible expression system (Invitrogen) according to the manufacturers instructions, and were maintained in DMEM/high glucose, 10% fetal bovine serum with 100 µg/mL Zeocin+800 µg/mL G418. IGFBP-3 protein production was induced with the addition of ponasterone A (Invitrogen) to the culture medium. Transfection experiments were done using either FuGene 6 (Roche) or TransIT-LT1 (Mirus) transfection reagent at a DNA/transfection reagent ratio of 1:2. Cell lysates were harvested by washing monolayer cultures in ice-cold PBS, and then lysing the cells in Triton lysis buffer (20 mM Tris, pH 7.6, 150 mM NaCl, 1% Triton X-100). Plates were rocked at 4° C. for 15 minutes, and lysates collected and centrifuged to remove debris. Cleared lysates were stored at −20° C. if not used immediately. Membrane preparations were generated by scraping cells into homogenization buffer (10 mM NaPO$_4$, pH 7.4, 1 mM EDTA, 150 mM NaCl, 250 mM sucrose) and centrifuging successively at 3K, 12K, and 40K×g. Pellets from the 40K×g spin were solubilized in 50 mM HEPES, pH 7.4, 150 mM NaCl, 2 mM MgSO$_4$, 1% Triton X-100.

Cell surface binding assay. Cells were seeded into 24-well plates and grown to 60-70% confluency, then transfected according to manufacturer instructions in serum-containing medium for 36 hours. Sf9 cells were seeded into 24-well plates and infected with virus harboring the 4-33$^F$ cDNA for 48 hours. Cells were washed in cold PBS, then incubated for 3 hours at 12° C. in binding buffer (1× Hank's buffered salt solution, 1 mM CaCl$_2$, 1 mM MgCl$_2$, 0.5% BSA) containing [$^{125}$I]-IGFBP-3 (Diagnostic Systems Laboratories) at 50,000 cpm per well in triplicate, with or without unlabelled IGFBP-3 as indicated in the text below. The binding solution was then aspirated and the cells washed in cold binding buffer (without BSA), lysed in 0.25 N NaOH, and the radiolabelled IGFBP-3 present in each lysate was detected in a gamma counter.

Results

Increased Specific IGFBP-3 Cell-Surface Binding. Hs578T and MCF-7 human breast cancer cells were transiently transfected for 36 hours with a construct encoding P4.33 tagged with FLAG at the C-terminus (P4.33$^F$), or with vector alone. Additionally, Sf-9 insect cells were infected for 48 hours with virus encoding P4.33$^F$, or were uninfected. The transfected or infected cells were then subjected to a monolayer binding assay using [$^{125}$I]-labeled IGFBP-3. Cell-surface binding of [$^{125}$I]-labeled IGFBP-3 was significantly enhanced in cells transfected with a clone 4.33 vector (FIG. 4A).

FIG. 4A shows that overexpression of P4.33$^F$ resulted in a 30-60% increase in [$^{125}$I]-labeled IGFBP-3 binding to the mammalian cell surface relative to cells expressing endogenous levels of P4.33. This result was greatly magnified (3.5 fold over control) when the same assay was done using Sf9 insect cells uninfected or infected with virus harboring the 4.33$^F$ cDNA, because the differential expression of P4.33$^F$ over control levels in these cells was considerably greater compared to differential overexpression in the tested mammalian cells.

FIG. 4B shows that the enhanced [$^{125}$I]-labeled IGFBP-3 binding was specific, and was unaffected by the presence of the FLAG-tag at the C-terminus of P4.33$^F$. Hs578T cells were transiently transfected with vector alone, un-tagged or FLAG-tagged clone 4.33 for 36 hours. Cells were then washed and exposed to [$^{125}$I]-labelled IGFBP-3 plus and minus increasing amounts of unlabelled IGFBP-3 as indicated for 3 hours at 12° C. The measured [$^{125}$I]-labelled IGFBP-3 binding was competed in a dose-dependent manner with the addition of unlabelled IGFBP-3 or IGF peptides but not by IGF binding proteins -2, -4, -5 or -6, demonstrating IGFBP-3R specificity for binding IGFBP-3.

Furthermore, addition of IGFBP-3 fragments comprising amino acids 88-148, and 98-264 competed for cell-surface binding of full-length IGFBP-3 to overexpressed IGFBP-3R, whereas a fragment comprising the N-terminal amino acids 1-97 had no effect. This result is consistent with the fact that the IGFBP-3R cDNA was isolated based on interaction with this region of IGFBP-3.

Co-translocation of P4.33$^F$ and IGFBP-3 to the Nucleus. FIG. 5 shows that P4.33 is translocated to the nucleus in association with $^{OG}$IGFBP-3. Purified IGFBP-3 that was labeled with OregonGreen ($^{OG}$IGFBP-3), and thus could be tracked using fluorescent microscopy, was used to examine whether the specific cell-surface binding of $^{OG}$IGFBP-3 resulted in uptake of $^{OG}$IGFBP-3 into the cell. Hs578T cells were transiently transfected with FLAG-tagged clone 4.33 for 24 hours. Cells were then incubated with 30 or 100 nm $^{OG}$IGFBP-3 in serum-free medium for 24 hours. Cells were washed, fixed in 4% paraformaldehyde, and immunostained with the α-4.33 polyclonal antibody, followed by α-rabbit-Texas Red secondary antibody. Hoechst dye was used as a nuclear indicator.

FIG. 5 shows that the uptake of fluorescent $^{OG}$IGFBP-3 into the cells was readily apparent, as well as its further translocation to the nucleus. The $^{OG}$IGFBP-3 colocalized with P4.33$^F$ in the cytoplasm, as detected by α-FLAG M2 antibody, and both were translocated to the nucleus, as shown in the representative images of FIG. 5. Additional experiments showed that nuclear localization of P4.33 was not seen in the absence of IGFBP-3, indicating that the nuclear transport of P4.33 is facilitated by IGFBP-3.

EXAMPLE 4

Generation of a Polyclonal Antibody and Sub Cellular Localization of P4.33

According to the present invention, a polyclonal antibody against P4.33 was generated to facilitate studies of endogenous P4.33. Briefly, the P4.33 cDNA was cloned in-frame with GST and the resulting fusion protein was overexpressed and purified from *E. coli*. Purified GST::P4.33 was then injected into rabbits to elicit α-P4.33 polyclonal antibody.

Material and Methods

Polyclonal antibody generation. A portion of the P4-33 cDNA sequence encoding amino acids 31-240 was cloned into the pGEX4T-1 vector (Amersham Pharmacia), in frame with GST, to generate pGEX:P4-33. This plasmid was transformed into *E. coli* BL21:DE3 pLysS and expression was induced with 0.1 mM IPTG for 3 hours. The resultant GST:: 4-33 fusion protein was insoluble, therefore a 51 kDa band was purified from SDS-PAGE for injection into three rabbits. Preimmune serum was obtained from each rabbit two days prior to initial injection. 50 μg of GST::P4-33 in Freund's Complete Adjuvant was injected subcutaneously, with subsequent boosts of 25 μg in Freund's Incomplete Adjuvant at 6 week intervals. Bleeds of 15 mL of immune serum were taken at 10 days post-injection and tested for immunoreactivity (specificity for P4.33 and cross-reactivity with purified GST) in western immunoblotting assays. Final bleeds were taken following the second boost injection. The rabbits were exsanguinated, and sera were collected from whole blood.

Western Immunoblotting. Samples were run on 12.5% reducing SDS-PAGE and electrotransferred onto Hybond-ECL nitrocellulose (Amersham). Membranes were blocked in 5% nonfat milk/TBS-0.1% Tween-20 (TBS-T). Primary antibodies were diluted in blocking solution and incubated on the membranes for 2 hours at room temperature. Membranes were washed in TBS-T, then incubated with HRP-conjugated secondary antibody, diluted 1:3000, for 1 hour at room temperature, washed, and detected using the Renaissance Western Blot Chemiluminescence reagents (NEN).

Immunoprecipitations. Immunoprecipitations were performed as described above under Example 2.

Results

α-P4.33 Polyclonal Antibody. FIG. 6A shows a western immunoblot (WIB) analysis of samples corresponding to: purified unfused GST; GST::P4.33 fusion protein; Hs578T conditioned medium (CM) and Hs578T cell lysate (CL). The purified samples were subjected to duplicate reducing SDS-PAGE. Following transfer, WIB analysis was performed using either preimmune serum or α-P4.33 polyclonal antibody. The α-P4.33 polyclonal antiserum readily recognized the GST::P4.33 fusion protein, and cross-reactivity with unfused GST was low. Additionally, the α-P4.33 polyclonal antibody recognized a protein species of 32 kDa from Hs5778T cell lysates, and this same protein species was seen in all other cell lines tested. Nothing was detected in Hs5778T-conditioned media.

The IGFBP-3R polyclonal antiserum and antibody (i.e., α-P4.33) recognized the 55 kDa GST::IGFBP-3R fusion protein, and a species of roughly 32 kDa from immunoblotted Hs578T human breast cancer cell lysates (FIG. 2B). A species of this size was detected in all other cell lines tested. Nothing was detected from the corresponding conditioned media, and cross-reactivity with purified GST was low. In immunocytochemistry experiments, the α-P4.33 (IGFBP-3R) antibody recognized overexpressed IGFBP-3R$^F$ in an identical pattern to that detected with the anti-FLAG M2 antibody. Surrounding untransfected cells displayed an identical, less intense, staining pattern with the IGFBP-3R antibody, the same perinuclear/cytoplasmic subcellular localization pattern as was seen for the EGFP::IGFBP-3R fusion protein.

The α-P4.33 polyclonal antibody was also tested in an immunoprecipitation/WIB analysis using EGFP-fused P4.33 (FIG. 6B). Briefly, cells were transiently transfected for 36 hours with either an EGFP::P4.33 fusion protein vector or with a control vector. Lysates from these transfected COS-7 cells were precleared using Protein A sepharose, and then subjected to immunoprecipitation with either preimmune serum or α-P4.33 antibody plus Protein A sepharose, and then subjected to reducing SDS-PAGE. Following transfer, WIB analysis was performed using α-GFP monoclonal antibody. FIG. 6B shows that the EGFP::P4.33 fusion protein, but not the unfused EGFP, was immunoprecipitated by the α-P4.33 polyclonal antibody. No immuoprecipitation was seen with preimmune sera.

The α-P4.33 polyclonal antibody was also functional for use in immunocytochemisty (FIG. 6C). Hs578T cells were transiently transfected with FLAG-tagged clone 4.33 for 36 hours. Cells were then fixed and dual immunostained with the α-P4.33 polyclonal antibody and α-FLAG M2 monoclonal antibody (green fluorescence), followed by α-mouse-FITC and α-rabbit-Texas Red secondary antibodies. Hoechst dye was used as a nuclear indicator. Confocal images from α-FLAG were overlaid onto images of α-P4.33 staining to generate a yellow color where overlapping green and red fluorescence was detected. FIG. 6C shows that this dual immunostaining of P4.33$^F$-transfected Hs578T human breast cancer cells produced identical staining patterns upon detection using fluorescent confocal imagery. No signal was seen with the preimmune sera.

Localization of P4.33 Protein in Adherent and Suspended Breast Cancer Cells. FIGS. 6C and 6D show that the localization of P4.33 protein in adherent and suspended breast cancer cells is readily apparent. In Hs578T adherent cells, P4.33 forms a distinct perinuclear ring with additional immunostaining apparent in the cytoplasm, and possibly on the cell surface (see upper left quadrant of FIG. 6C).

Immunostaining was also preformed on cells in suspension to determine whether P4.33 was located on the cell surface (FIG. 6D). Hs578T and MCF-7 cells were transiently transfected with FLAG-tagged clone 4.33 for 36 hours. The cells were then trypsinized, washed, and the nuclei stained with propidium iodide. Cells were subsequently washed extensively with phosphate buffered saline (PBS), and incubated with either α-P4.33 polyclonal antibody or α-FLAG M2 monoclonal antibody, followed by incubation with α-mouse-FITC and α-rabbit-Texas Red secondary antibodies. Hoechst dye was used as a nuclear indicator.

Immunostaining in this manner, without fixation or permeabilization, allowed for the visualization of lower levels of cell surface P4.33, without interference from intracellular signal. Cell surface localization of P4.33 is readily apparent. Both transfected P4.33$^F$ (detected with the α-FLAG M2 antibody), and endogenous P4.33 (detected with the α-P4.33 antibody) displayed a characteristic ring pattern around the surface of suspended MCF-7 and Hs578T breast cancer cells (FIG. 6D) indicative of cell-surface staining. This same ring pattern was also seen in immunostained Sf9 insect cells infected with virus encoding P4.33$^F$.

P4.33 in Crude Membrane Preparations. Furthermore, P4.33 was determined to be present in crude membrane preparations. Duplicate wells of Hs578T cells were used for preparation of crude membranes by differential centrifugation of cell lysates at 3,000, 12,000, and 2×40,000×g. Resuspended pellets from the second 40,000×g centrifugation were immunoblotted with the α-P4.33 antibody. The two immunoblot lanes on the right of FIG. 6D show a comparison of control vector-transfected and p4.33$^F$ vector-transfected Hs578T breast cancer cells by western immunoblotting using the α-P4.33 antibody. These lanes show that overexpression of P4.33$^F$ allowed for the detection of P4.33 in crude membrane preparations. The level of endogenous P4.33 localized to the plasma membrane was below the sensitivity of this assay.

Accordingly, the α-P4.33 polyclonal antibody, generated in response to the GST::4.33 fusion protein, was shown to specifically immunoprecipitate a 32 kDa protein species from Hs578T and other cell lysates. Moreover, the α-P4.33 polyclonal antibody was functional for use in immunocytochemisty, and revealed that endogenous and transiently expressed P4.33 was localized in the cytoplasm, in a perinuclear pattern, and on the cell surface of both adherent and suspended cells. Finally, the α-P4.33 polyclonal antibody was also used to detect P4.33 in crude membrane preparations.

EXAMPLE 5

P4.33 Involvement in IGFBP-3-Induced Growth Inhibition

According to the present invention, transient overexpression of P4.33 in IGFBP-3 expressing Hs578T breast cancer cells resulted in a significant increase in cell detachment and death over time (FIG. 7A). Specifically, induction of IGFB-3 in the absence of transiently expressed P4.33 suppressed DNA synthesis in MCF-7 cells by an average of 55% of control levels, whereas induction of IGFBP-3 in the presence of transiently expressed P4.33 further suppressed DNA synthesis to 35% of control levels (FIG. 7C). Transient expression of P4.33 resulted in significantly enhanced inhibition of DNA synthesis in the presence of IGFBP-3.

Material and Methods

Cell Culture and Transfection. Cell Culture and Transfection was performed as described above under Example 3, "Material and Methods."

Thymidine incorporation assay. Briefly, cells were seeded in triplicate into 24-well plates, grown to 60-70% confluency, and transfected and treated as indicated in the text. At 48 hours post-transfection, media was removed and replaced with serum-free medium and cells were further incubated for 24 hours. To each well 0.1 μCi [$^3$H]-thymidine was added, and the acid-precipitable radioactivity in each well was assayed 24 hours later.

Results

Transient expression of P4.33 in the presence of IGFBP-3 resulted in growth inhibition and cell death. P4.33$^F$ was transiently expressed in the presence of IGFBP-3 to investigate the effect of P4.33 on cancer cell growth (FIG. 7A). Specifically, Hs578T (IGFBP-3-expressing) and MCF-7 (IGFBP-3-nonexpressing) cells were transiently transfected with control vector (CS2+) or FLAG-tagged clone 4.33 vector (CS/4.33$^F$). Representative phase contrast images of cell populations at 48 hours post-transfection were then examined for cell numbers. FIG. 7A shows that transient overexpression of P4.33$^F$ in IGFBP-3 expressing Hs578T breast cancer cells resulted in a significant increase in cell detachment and death over time (compare upper two phase-contrast fields), compared to little or no effect in MCF-7 cells that do not produce IGFBP-3 (compare lower two phase-contrast fields).

A stably-transfected inducible IGFBP-3 MCF-7 breast cancer cell line was generated using the ecdysone-inducible system to further investigate the biological actions of P4.33 and IGFBP-3 (FIG. 7B). MCF-7 cells do not normally express IGFBP-3, and therefore allowed for the generation of a stable MCF-7 line, MCF-7:BP-3, #3 (colony #3), in which IGFBP-3 expression was inducible by incubation of ponasterone A, at concentrations of about 2-15 µM. An additional MCF-7 sub-line, MCF-7:BP-3, #1, was generated that constitutively expressed IGFBP-3 at a similar level without the addition of ponasterone A (FIG. 7B).

Wild type MCF-7 and the inducible MCF-7:BP-3, #3 cells were transiently transfected with control vector (CS2+) or with FLAG-tagged clone 4.33 vector (CS/4.33$^F$). After 24 hours, the cells were incubated in serum-free medium for 12 hours, followed by the addition of 0 or 15 µM ponasterone A. [$^3$H] thymidine (0.1 µCi) was added after 48 hours, and the cells were then assayed for [$^3$H]-thymidine incorporation after an additional 24 hours. The histogram of FIG. 7C reflects the average of three independent experiments, and shows that induction of IGFB-3 in the absence of transiently expressed P4.33 suppressed DNA synthesis in MCF-7 cells by an average of 55% of control levels (i.e., compare the two right-hand dark-colored vertical bars in FIG. 7C), whereas induction of IGFBP-3 in the presence of transiently expressed P4.33 further suppressed DNA synthesis to 35% of control levels (i.e., compare the two right-hand light-colored vertical bars in FIG. 7C). P4.33 expression had no significant effect in the absence of IGFBP-3 expression (i.e., compare the dark and light bars of the third pair (from the left) of vertical bars in FIG. 7C), and neither P4.33 nor ponasterone A had any effect in wild type MCF-7 cells (i.e., compare the left two pairs of vertical bars in FIG. 7C).

FIG. 7D shows that overexpression of P4.33 had a similar effect in PC-3 prostate cancer cells. In these cells, that produce IGFBP-3, DNA synthesis was inhibited by transient transfection of P4.33 relative to control transfected cells (FIG. 7D).

Therefore, according to the present invention, transient overexpression of P4.33 in IGFBP-3 expressing Hs578T breast cancer cells resulted in a significant increase in cell detachment and death over time. Likewise, transient expression of P4.33 resulted in significantly enhanced inhibition of DNA synthesis (i.e., growth inhibition, or cell death) in a stably-transfected inducible IGFBP-3 MCF-7 breast cancer cell line. Finally, overexpression of P4.33 in PC-3 prostate cancer cells (that produce IGFBP-3) suppressed DNA synthesis.

EXAMPLE 6

Induction of Apoptosis by P4.33 and IGFBP-3 in Breast Cancer Cells

Breast cancer cells were transfected with control vector (CS2+) or with FLAG-tagged clone 4.33 vector (CS/4.33$^F$) to determine if P4.33 and IGFBP were involved in the induction of apoptosis.

Material and Methods

Cell Culture and Transfection. Cell Culture and Transfection was performed as described above under Example 3, "Material and Methods."

Apoptosis and cell cycle/flow cytometry assay. All assays analyzed by flow cytometry were done on a Becton-Dickinson FACSCalibur™ flow cytometer. For cell-cycle analysis, cells were seeded into 6-well plates and transfected at 70-80% confluency. At the time of the assay, cells were trypsinized and resuspended in PI staining solution (1×PBS, 100 U/mL RNase, 50 µg/mL propidium iodide) and incubated at RT in the dark for 30 minutes before analysis. For detection of early apoptotic cells, trypsinized cell suspensions were subjected to a FITC-labelled Annexin V binding assay (Santa Cruz Biotechnology, Santa Cruz, Calif.) according to the manufacturer's directions Caspase assays. For assay of caspase activity, cells were seeded in 96-well plates and transfected at 70-80% confluency. After 48 hours, cells were lysed in 30 µl per well of ice-cold lysis buffer (50 mM HEPES, pH 7.4, 0.1% CHAPS, 0.1% Triton X-100, 1 mM DTT, 0.1 mM EDTA). Serial dilutions of free 7-amino-4-methylcoumarin (AMC, Sigma) diluted in assay buffer were included to generate a reference standard curve. Twenty µl of each lysate were assayed using a combination of two fluorogenic peptide substrates, DEVD-AMC and LEHD-AMC (Biomol), at 40 µM each according to the manufacturer's directions. Reaction kinetics were monitored for up to 16 hours at 37° C. in a Bio-Rad Fluoromark™ microplate fluorometer, with plate readings taken every 10 minutes at excitation/emission of 390 nm/460 nm. Data were analyzed from the linear portion of the reactions using Microplate Manager software (Bio-Rad), and final results were adjusted for protein content.

Western Immunoblotting. Western Immunoblotting was performed as described above under Example 4, "Material and Methods."

Results

Flow cytometric analysis showed that P4.33-transfected cells display an increase in the sub-G1 cell population and a concurrent decrease in the S/G2/M population. Flow cytometry was used to investigate the growth-inhibitory actions of P4.33 and IGFBP-3. See FIG. 8A. Hs578T (IGFBP-3 expressing), MCF-7 (IGFBP-3 non-expressing) and induced MCF-7:BP-3, #3 cells were either untreated or transiently transfected with control vector (CS2+) or with FLAG-tagged clone 4.33 vector (CS/4.33$^F$) for 24 hours. The cells were then harvested, and the DNA content/cell cycle profile was analyzed by propidium iodide staining followed by flow cytometric detection. In each case, the P4.33-transfected cells displayed an increase in the sub-G1 population and a concurrent decrease in the S/G2/M population compared to control cells (FIG. 8A). A peak in the sub-G1 range can be indicative of cells undergoing apoptosis.

This was investigated further using an Annexin V assay, which is used to identify cells early in the apoptotic process. By incubating suspended cells with FITC-labeled Annexin V, coupled with concurrent propidium iodide staining without permeabilization of the plasma membrane, it is possible to discriminate between cells in early apoptosis and those in late apoptosis or necrosis using a two-color flow cytometic analysis.

Hs578T cells were transfected with control vector (CS2+) or with FLAG-tagged clone 4.33 vector (CS/4.33$^F$), and subsequently harvested at 14, 24, 36 and 48 hours post-transfection. At each time point, harvested cells were incubated with FITC-labeled Annexin V, then washed and resuspended in propidium iodide staining solution. A two-color flow cytometry analysis was done to discriminate between early apoptotic (lower right quadrant of each frame) and late apoptotic/necrotic (upper right quadrant of each frame) cells. FIG. 8B shows that at each time point, the population of early apoptotic cells was significantly increased in the cells transfected with P4.33, compared to control-transfected cells.

Induction of apoptosis by P4.33 and IGFBP-3 in breast cancer cells. The effect of IGFBP-3/P4.33 signaling on specific proteins known to be involved in cell cycle progression and the apoptotic process was examined to determine the mechanism involved in IGFBP-3/P4.33 mediated growth inhibition.

FIG. 9 shows that over-expression of P4.33 in cells that express IGFBP-3, or induction of IGFBP-3 in the inducible MCF-7:BP-3 #3 cell line, resulted in induction of apoptosis. Hs578T (IGFBP-3 expressing), MCF-7 (IGFBP-3 non-expressing) and MCF-7:BP-3, #1 (constitutively expressing IGFBP-3) cells were left untreated, treated with sodium butyrate (NaB, apoptotic inducer) or transiently transfected with control vector (CS2+) or with FLAG-tagged clone 4.33 vector (CS/4.33$^F$) for 24 hours. Cell lysates were then harvested, and assayed for protein content. Equal amounts of protein were electrophoresed and immunoblotted with antibodies against cell cycle regulatory proteins cyclin D1, cyclin E and p21/Waf1. The left portion of FIG. 9 shows that over-expression of P4.33 in the presence of IGFBP-3 resulted in a significant reduction in the levels of cyclin D1, which is required for cells to progress from G1 into S phase. No affect was seen on cyclin E or p21/Waf1. Proper upregulation of p21/Waf1 was seen with the control NaB treatment.

Likewise, induction of IGFBP-3 in the inducible MCF-7:BP-3 #3 cell line, resulted in induction of apoptosis (right panel of FIG. 9), presumably mediated through endogenous P4.33.

The data of FIG. 9, along with the flow cytometry data (FIGS. 8A and 8B), indicated that transient overexpression of P4.33 in cells that express IGFBP-3 resulted in induction of apoptosis in breast cancer cells.

Figure 19:
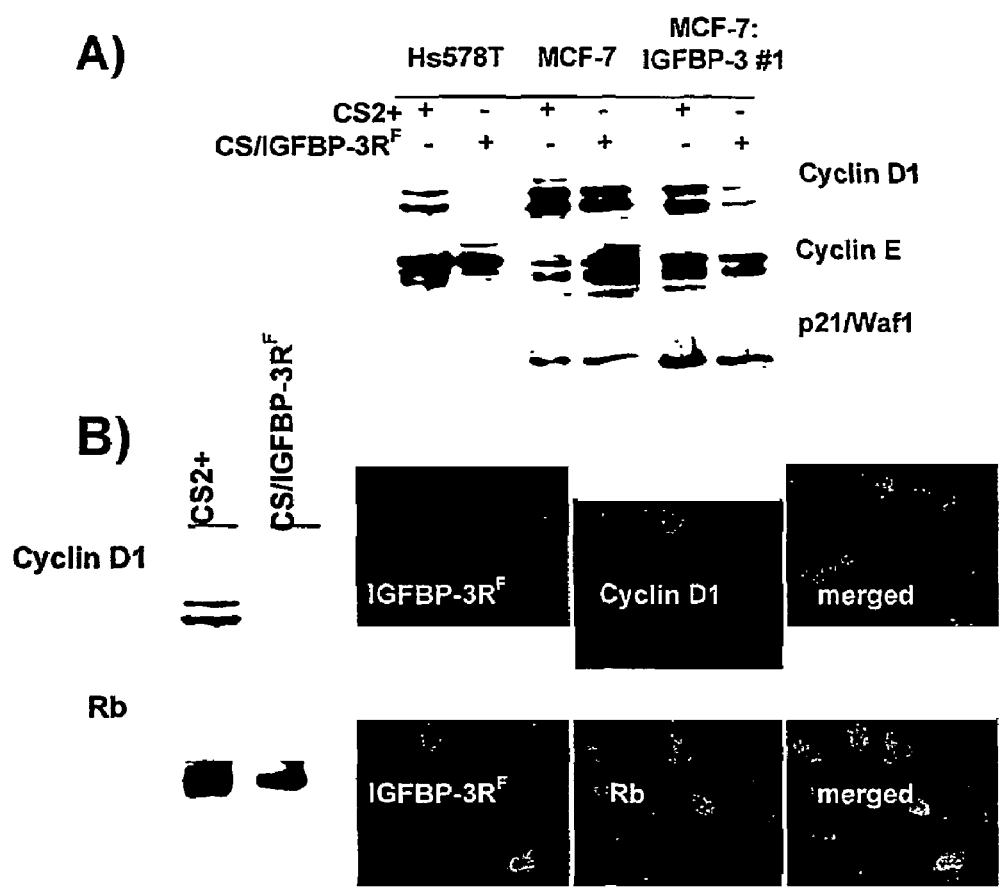
FIG. 19 shows specific reduction of cyclin D1 and Rb protein levels in Hs578T cells overexpressing IGFBP-3R in the presence of IGFBP-3. Overexpression of IGFBP-3R in the presence of IGFBP-3 resulted in a significant reduction in the levels of cyclin D1 (upper panel). There was no effect on cyclin E or p21/Waf1 (upper panel). In addition to cyclin D1, levels of Rb protein were similarly reduced (lower panel). Both of these effects were specific to IGFBP-3R-transfected cells as shown by dual immunostaining of transfected Hs578T cells with IGFBP-3R (green) and either cyclin D1 or Rb (red) antibodies (lower panel).

In addition to Cyclin D1, a reduction in the levels of retinoblastoma (Rb) protein was seen in Hs578T cells with overexpression of IGFBP-3R in the presence of IGFBP-3 (FIG. 19). FIG. 19 shows specific reduction of cyclin D1 and Rb protein levels in Hs578T cells overexpressing IGFBP-3R in the presence of IGFBP-3. Overexpression of IGFBP-3R in the presence of IGFBP-3 resulted in a significant reduction in the levels of cyclin D1 (upper panel). There was no effect on cyclin E or p21/Waf1 (upper panel). In addition to cyclin D1, levels of Rb protein were similarly reduced (lower panel). Both of these effects were specific to IGFBP-3R-transfected cells as shown by dual immunostaining of transfected Hs578T cells with IGFBP-3R (green) and either cyclin D1 or Rb (red) antibodies (lower panel).

Therefore, immunocytochemistry experiments revealed that the reduced levels of both Cyclin D1 and Rb were correlated to IGFBP-3R-overexpression. When cell populations were dually stained for IGFBP-3R transfection and either Cyclin D1 or Rb protein, the IGFBP-3R-positive cells showed specific reduction in staining intensity of Cyclin D1 and Rb compared to surrounding untransfected cells (FIG. 19). The percentage of IGFBP-3R-positive cells with reduced Cyclin D1 (94%) or Rb (83%) levels was significantly greater than in the untransfected population in both cases (38% and 23%, respectively).

These results indicate that disruption of the cell cycle is involved in IGFBP-3/IGFBP-3R-induced growth inhibition, and that this disruption is p21/Waf1 independent.

EXAMPLE 7

Figure 10:
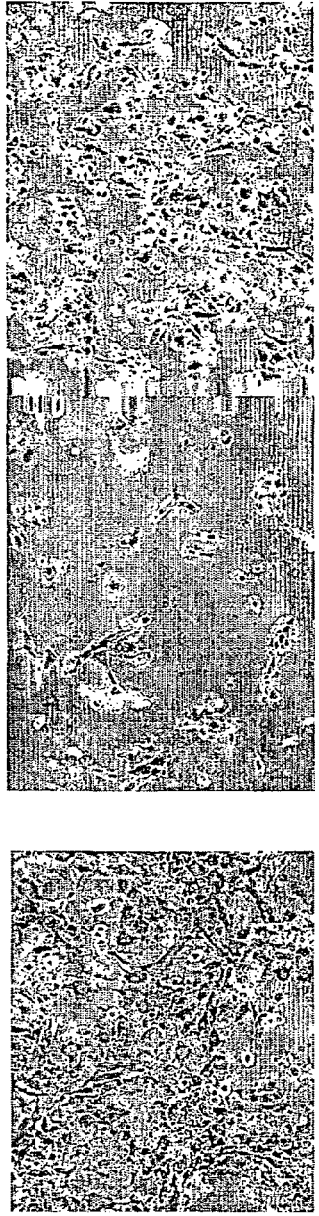
FIG. 10 shows photographs of variouss adherant cancer cell cultures that were infected with the P4.33 expression vector Ad:IGFBP-3R either in the absence, or the presence of tetracyclin, an inhibitor of the expression vector. The photographs show that Ad:IGFBP-3R-mediated P4.33 (IGFBP-3R) expression resulted in substantial growth inhibition. Specifically, a significant growth inhibitory effect was demonstrated in human breast cancer cells (Hs578t and MDA231; upper left and right two quadrants, respectively), prostate cancer cells (PC-3; lower-right quadrant) and non-small cell lung carcinoma cells (H1157) (lower-left quadrant). For each cell type, the plus "+" symbol indicates infection with Ad:IGFBP-3R in the absence of tetracyclin, whereas the minus "−" symbol indicates infection with Ad:IGFBP-3R in the presence of tetracyclin, which blocks expression of IGFBP-3 protein.
Figure 10:
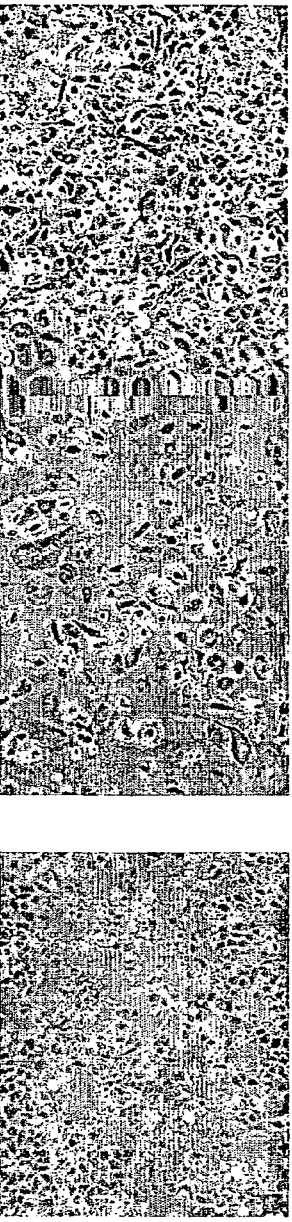

Induction of Growth Inhibition and Apoptosis in Cancer Cells by infection with Ad:IGFBP-3R, a Recombinant Adenovirus P4.33 (IGFBP-3R) Expression Vector Additional embodiments of the present invention comprise adenovirus expression vectors and adenovirus gene transfer technology. Ad:IGFBP-3R, a recombinant adenovirus P4.33 expression vector, was constructed and used to over-express IGFBP-3 receptor (P4.33) in a variety of cancer cells. Such over-expression of P4.33 resulted in substantial growth inhibition in human breast cancer cells (Hs578t and MDA231), prostate cancer cells (PC-3) and non-small cell lung carcinoma cells (H157) (FIGS. 10 and 11). Furthermore, the IGFBP-3R-induced growth inhibition was attributed to induction of apoptosis, a specific cell death process mediated, at least in part by IGFBP-3:IGFBP-3R-dependent caspase induction/activation (FIGS. 12-18).

Material and Methods

Ad:IGFBP-3R Construction and Purification. Ad:IGFBP-3R, a δE1-δE3 recombinant adenovirus, was constructed to express the human IGFBP-3 receptor cDNA (i.e., the P4. cDNA) under the control of $P_{hCMV-1}$, a tetracycline ("Tet")-responsive promoter from human cytomegalovirus. $P_{hCMV-1}$ is silent (off) in the presence of Tet, which precludes interaction between the Tet$^R$ element and the teto sequences of $P_{hCMV-1}$ (CLONTECH Laboratories Inc, Palo Alto, Calif.).

Specifically, a poly-A signal, and the $P_{hCMV-1}$ Tet$^R$promoter (containing the Tet-responsive element ("TRE"), consisting of seven copies of the 42 base pair Tet operator sequence) was inserted into the pShuttle™ plasmid, (a gene-transfer vector from an AdEasy™ Adenovirus Recombinant Kit of Quantum Biotechnology, Montreal, Canada) to create a pShuttle:Tet$^R$pro:poly-A plasmid. The human IGFBP-3 receptor gene (as a EcoR1-XhoI DNA fragment, blunt-ended using Klenow polymerse) was then cloned into the EcoRV site of the pShuttle:Tet$^R$pro:poly-A plasmid, to create pShuttle:IGFBP-3R. The direction of the IGFBP-3R cDNA (sense- or antisense-orientation) in pShuttle:IGFBP-3R was confirmed by restriction digestion with XhoI. The sense directional plasmid gave rise to characteristic 7- and 1.3-kb XhoI fragments, whereas the antisense directional plasmid gave rise to 7.8- and 0.5-kb XhoI fragments. The sense shuttle vector, pShuttle:IGFBP-3R, was homologously recombined with pAdEasy™ (adenoviral genome-based plasmid) in BJ5183 *E. coli* according to the manufacturer's protocol. After homologous recombination, the recombinant adenoviral genome was excised by Pad digestion, and the Ad:IGFBP-3R recombinant adenovirus P4.33 expression vector was recovered by transfecting 10 μg of PacI digested DNA into 293 cells by a FuGENE 6-based procedure (Roche Molecular Biochemicals, Indianapolis, Ind.). Recombinant adenoviruses expressing EGFP and transactivating adenoviruses (TA) were also generated. All viral stocks were prepared from infected 293 cells according to the manufacturer's protocol. Briefly, viral stocks were concentrated and purified using a two-step purification on CsCl gradients, and viral titers (expressed in terms of PFU/ml) were estimated by measureing optical density at 260 nm.

MTS cell proliferation assays. MTS cell proliferation assays were performed using the CellTiter96 AQueous One Solution Cells Proliferation Assay kit (Promega). For this assay, cells were seeded in triplicate in 96-well microtitre plates, grown to 60-70% confluency, and treated as indicated. At 48 hours post-transfection, media was aspirated and cells were incubated in assay solution for 1-2 hours at 37° C. before measuring absorbance at 492 mm.

Results

Induction of Growth Inhibition. FIG. 10 shows photographs of variouss adherant cancer cell cultures that were infected with the P4.33 expression vector Ad:IGFBP-3R either in the absence, or the presence of tetracyclin, an inhibitor of the expression vector. The photographs show that adenovirus-mediated expression of P4.33 in these cancer cells results in substantial growth inhibition. Specifically, a significant growth inhibitory effect was demonstrated in human breast cancer cells (Hs578t and MDA231; upper half of FIG. 10), prostate cancer cells (PC-3; lower-right quadrant of FIG. 10) and non-small cell lung carcinoma cells (H157) (lower-left quadrant of FIG. 10). For each cell type, the plus "+" symbol indicates infection with Ad:IGFBP-3R in the absence of tetracyclin, whereas the minus "−" symbol indicates infection with Ad:IGFBP-3R in the presence of tetracyclin (in the presence of tetracyclin, virus can be amplified, but IGFBP-3 protein expression is blocked).

FIG. 11 summarizes the results of MTS proliferation assays of Hs578t, MDA231, PC-3 and H157 cell cultures that were infected with Ad:IGFBP-3R either in the absence, or the presence of tetracyclin. Growth inhibition was expressed as a percent of the control value, which is the growth rate in the presence of tetracyclin, which suppresses P4.33 (IGFBP-3R) expression. Ad:IGFBP-3R-mediated over-expression of the IGFBP-3R resulted in substantial growth inhibition compared to uninfected cells. For example, in PC-3 prostate cancer cells, IGFBP-3R over-expression resulted in about 90% growth inhibition compared to infected cells in the presence of tetracyclin. Successful adenovirus-mediated expression of IGFBP-3R was verified in each case by Western immunoblotting ("WIB").

Figure 12:
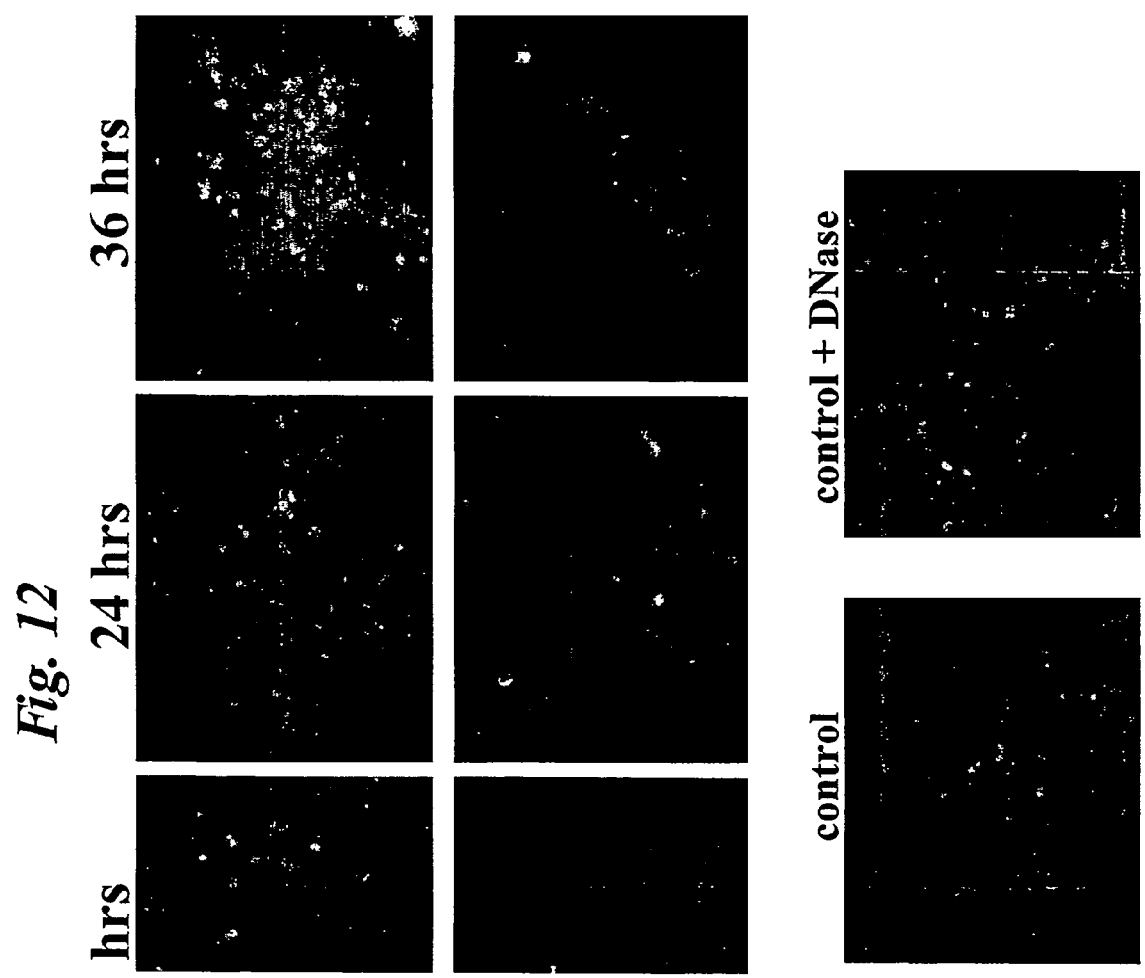
FIG. 12 shows the results of a standard TUNEL assay for apoptosis, illustrating that adenovirus-mediated expression of P4.33 (IGFBP-3R) in IGFBP-3R-transduced COS-7 cells resulted in induction of apoptosis, as demonstrated by tine-dependent increases of DNA fragmentation (upper three panels). The upper three panels, marked "−Tet" correspond to cell cultures without tetracycline (allows for over-expression of IGFBP-3). The middle panels, marked "+Tet" correspond to cell cultures containing tetracycline, which blocks P4.33 (IGFBP-3R) expression. The lower panels marked "control," and "control+Dnase," illustrate that no DNA fragmentation occurred in the absence of P4.33 (IGFBP-3R) over-expression.

Induction of Apoptosis. The above-described IGFBP-3R-mediated induction of growth inhibition was further characterized to determine whether it was attributed to induction of apoptosis, a specific cell death process. Specifically, FIG. 12 shows the results of a standard TUNEL assay (TdT-mediated dUTP nick end labeling, whereby fluorescein dUTP is incorporated to DNA strand breaks that resulting from apoptosis-induced DNA fragmentation; Gavrieli, Y et. al. *J. Cell Biol,* 119:49-501, 1992) for apoptosis (Boehringer Mannheim, Indianapolis, Ind.). The results show that adenovirus-mediated expression of P4.33 in IGFBP-3R-transduced COS-7 cells resulted in induction of apoptosis, as demonstrated by time-dependent increases of DNA fragmentation (FIG. 12, upper three panels). The upper three panels, marked "−Tet" correspond to COS-7 cell cultures without tetracycline, and which, therefore, are over-expressing IGFBP-3. The middle panels, marked "+Tet" correspond to COS-7 cell cultures containing tetracycline, which thus are not expressing P4.33 (IGFBP-3R). The lower panels marked "control," and "control+Dnase," illustrate that no DNA fragmentation occurred in the absence of P4.33 (IGFBP-3R) over-expression, whereas treatment with Dnase, used as a positive control for DNA fragmentation, resulted in significant increase of DNA fragmentation.

Caspase Activity Assays. Activation of Caspases has been implicated in the initiation of apoptosis. Three canonical pathways of caspase activation have been identified. First, caspases can be activatived by granzyme B, a major serine protease in cytotoxic lymphocyte granules.

Figure 14:
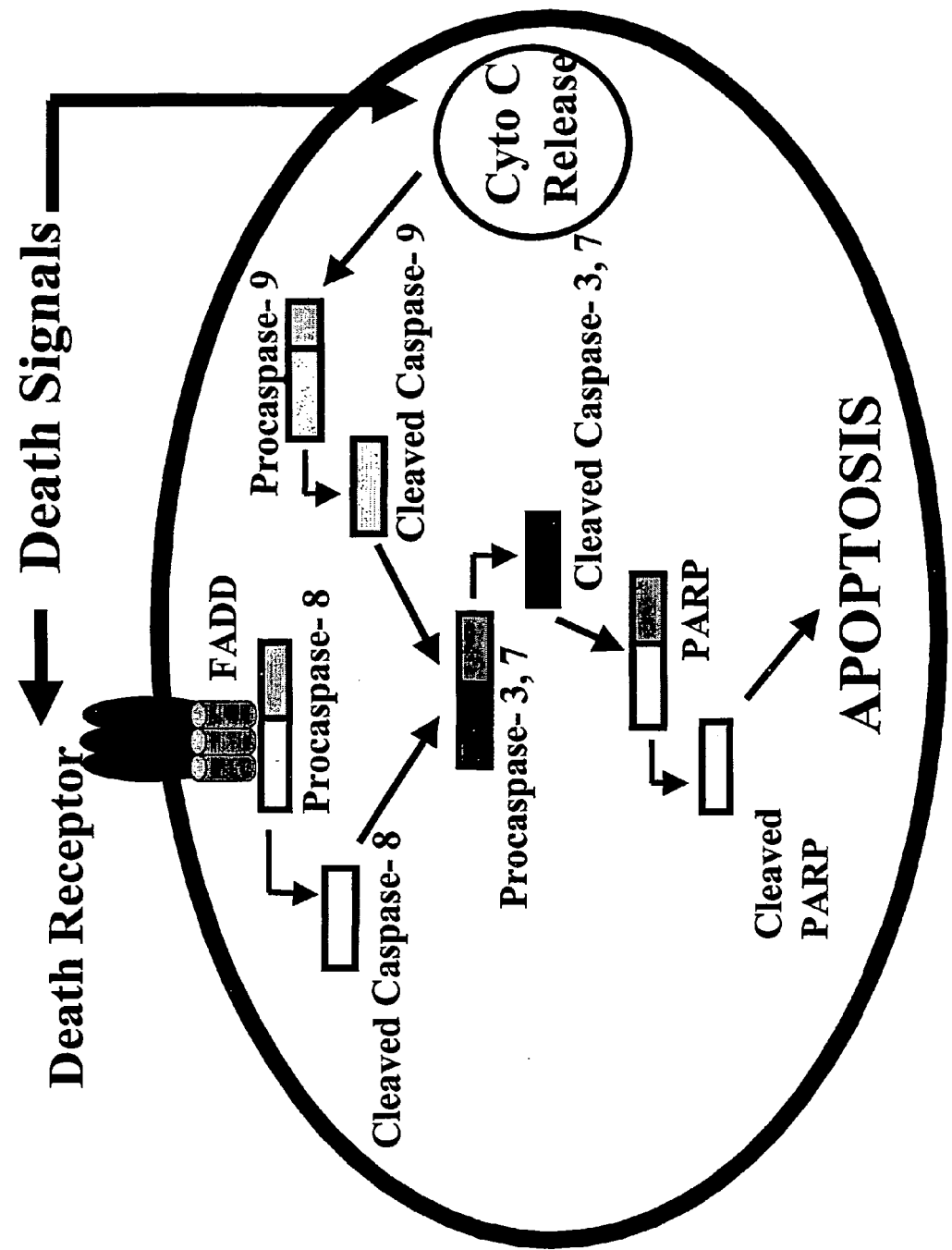
FIG. 14 shows a schematic representation of caspase activation pathways in a mammalian cell. Ligation of cell-surface "death" receptors (e.g., Fas, type-1 TNF-α receptor, or, as disclosed herein, the IGFBP-3 receptor) results in binding of adapter molecules ("FADD"), which in turn recruit pro-caspases (e.g., procaspase-8) to membrane-associated signaling complexes, leading to proximity-induced caspase-8activation. Alternatively, mitochondria are induced to release cytochrome c ("Cyto C Release"), which interacts with the cytosolic docking protein Apaf-1, thereby facilitating binding and activation of procaspase-9 to produce caspase-9, thought to proteolytically activate procaspase-3 and possibly procaspase-7. According to the present invention, P4.33 (IGFBP-3R) functions as a novel death receptor with respect to caspase activation.

Second, ligation of cell-surface "death" receptors, such as Fas or the type-1 TNF-α receptor, results in binding of adapter molecules ("FADD" in FIG. 14), which in turn recruit procaspases-2, -8 and -10 to membrane-associated signaling complexes, leading to proximity-induced activation (by cleavage of zymogens to the respective mature peptides) of these caspases (FIG. 14).

Finally, in some model systems, mitochondria are induced to release cytochrome c, which interacts with the cytosolic docking protein Apaf-1, thereby facilitating binding and activation of procaspase-9 ("Cyto C Release" in FIG. 14). After activation, caspase-9 is thought to proteolytically activate caspase-3 and possibly caspase-7 (FIG. 14).

While the present invention is not limited by any specific theory or mechanism, caspase activity and immunoblotting assays (Hengartner M. O., *Nature,* 407:770-775, 2000) were performed to determine whether IGFBP-3R promotes apoptosis via activation of caspases, and if so, which caspases.

Figure 13:
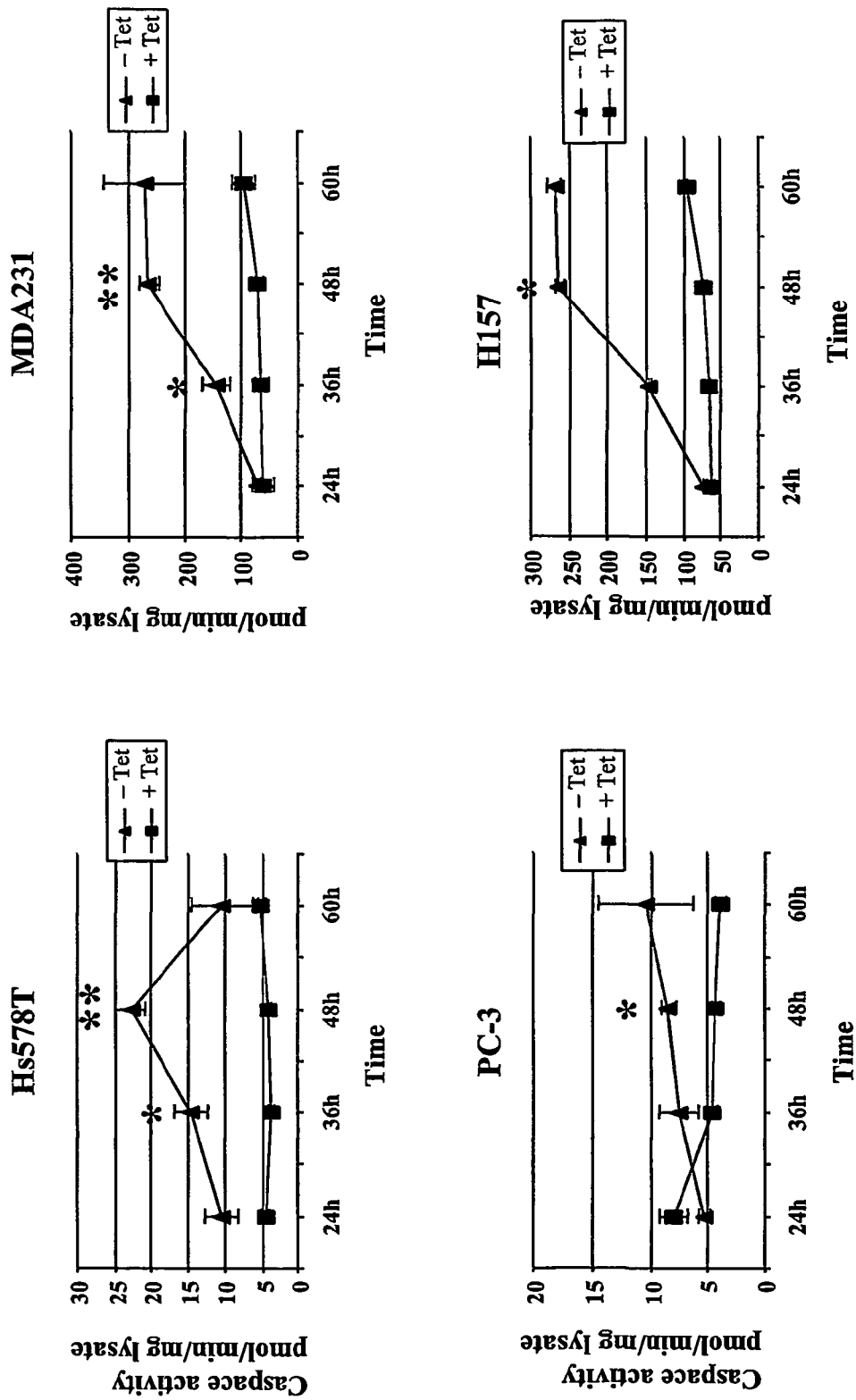
FIG. 13 shows that, in cells infected with the P4.33 expression vector Ad:IGFBP-3R, caspase activity was induced over time by Ad:IGFBP-3R-mediated IGFBP-3R (P4.33) over-expression (-Δ-; "−Tet"), but not where such expression was blocked by tetracyclin addition (-■-; "+Tet"). Specifically, such induction of caspase activity, expressed in units of pmol/min/mg/lysate, was found in human breast cancer cells (Hs578t and MDA231; upper two quadrants), prostate cancer cells (PC-3; lower-left quadrant) and non-small cell lung carcinoma cells (H157) (lower-right quadrant).

FIG. 13 shows that, in cells infected with Ad:IGFBP-3R, caspase activity (in units of pmol/min/mg/lysate; BIOMOL, Plymouth, Pa.) was induced over time by Ad:IGFBP-3R-mediated IGFBP-3R (P4.33) over-expression (-Δ-; "−Tet"), but not where such expression was blocked by Tet addition (--; "+Tet"). Specifically, such induction of caspase activity was found in human breast cancer cells (Hs578t and MDA231; upper half of FIG. 13), prostate cancer cells (PC-3; lower-left quadrant of FIG. 13) and non-small cell lung carcinoma cells (H157) (lower-right quadrant of FIG. 13).

Figure 15:
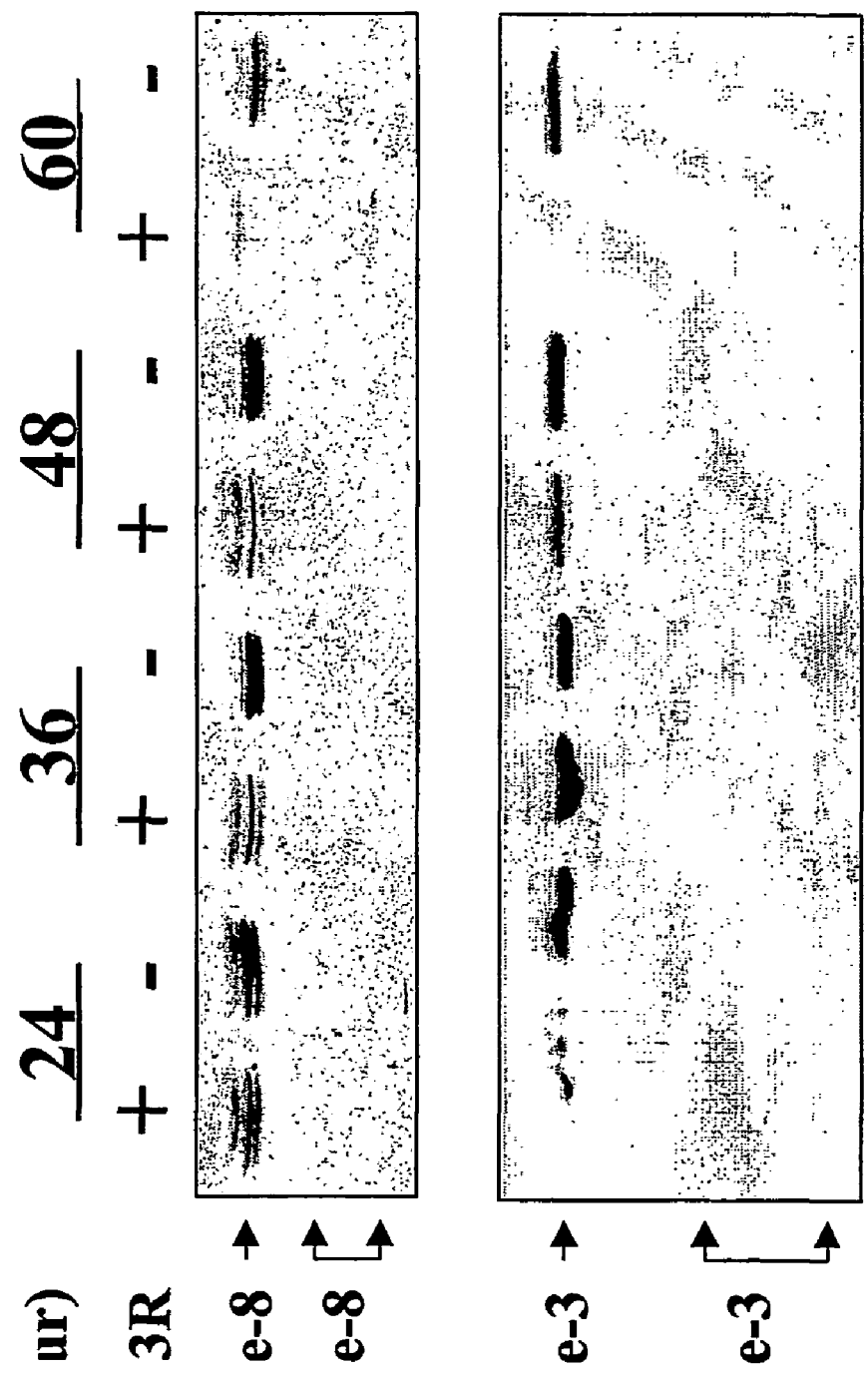
FIG. 15 shows immunoblots of lysates of Hs578T breast cancer cells that were infected with the P4.33 expression vector Ad:IGFBP-3R in the presence (lanes marked with a minus "−" symbol) or absence (lanes marked with a minus "+" symbol) of tetracyclin (which blocks P4.33 (IGFBP-3) expression), and incubated for various times. The data show that Ad:IGFBP-3R-mediated P4.33 (IGFBP-3R) over-expression resulted in significant increases of "cleaved" caspase-3 and -8 proteins (i.e., mature, activated caspases) in human breast cancer cells, which express endogenous IGFBP-3.
Figure 16:
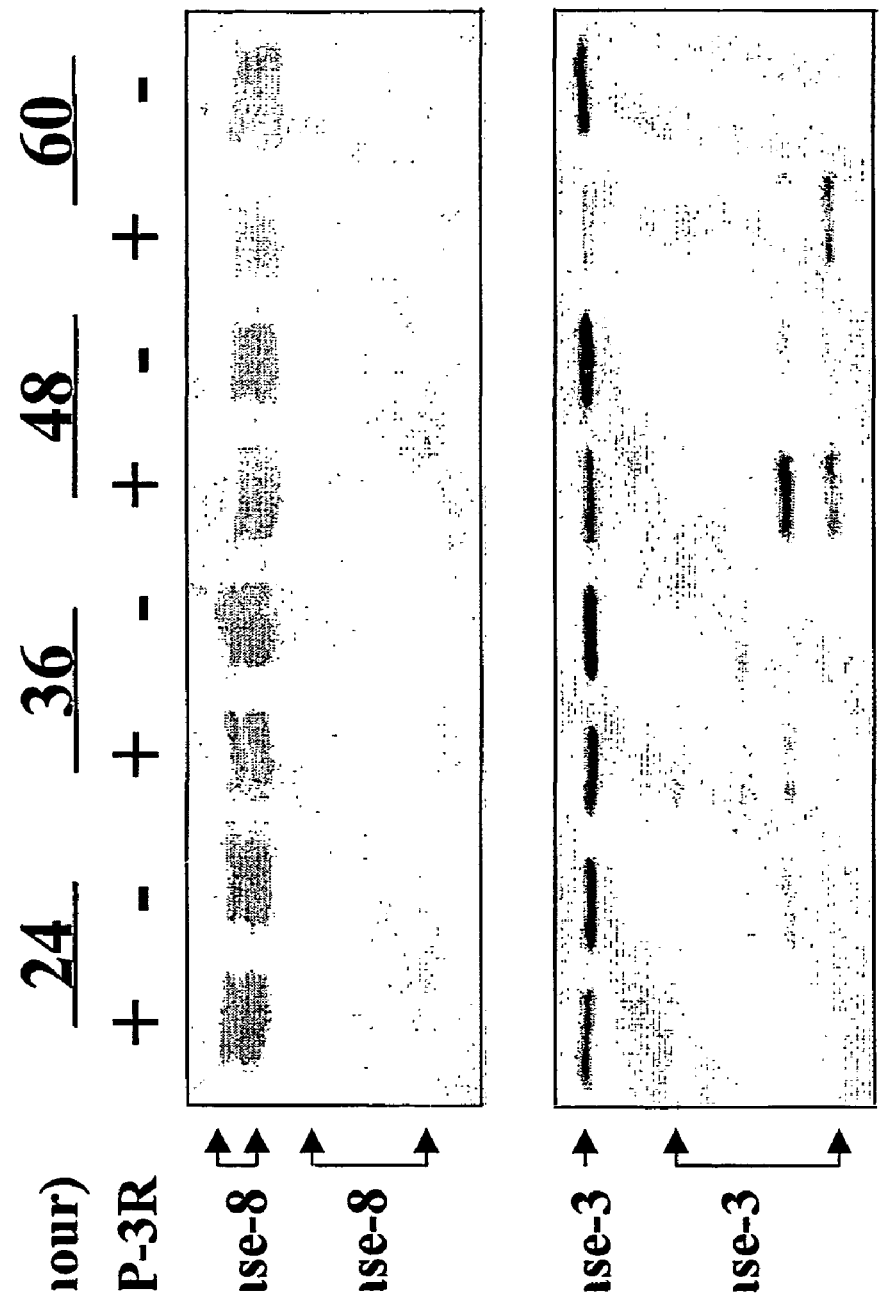
FIG. 16 shows immunoblots of lysates of MDA231 breast cancer cells that were infected with the P4.33 expression vector Ad:IGFBP-3R in the presence (lanes marked with a minus "−" symbol) or absence (lanes marked with a minus "+" symbol) of tetracyclin (which blocks P4.33 (IGFBP-3) expression), and incubated for various times. The data show that Ad:IGFBP-3R-mediated P4.33 (IGFBP-3R) over-expression resulted in significant increases of "cleaved" caspase-3 and -8 proteins (i.e., mature, activated caspases) in human breast cancer cells, which express endogenous IGFBP-3.

Furthermore, FIGS. 15 and 16 show immunoblots of of lysates of Hs578T and MDA231 breast cancer cells, respectively, that were infected with the P4.33 expression vector Ad:IGFBP-3R in the presence (lanes marked with a minus "−" symbol) or absence (lanes marked with a minus "+" symbol) of tetracyclin (which blocks P4.33 (IGFBP-3) expression), and incubated for various times. The data show that Ad:IGFBP-3R-mediated P4.33 (IGFBP-3R) over-expression resulted in significant increases of "cleaved" caspase-3 and -8 proteins (i.e., mature, activated caspases) in these human breast cancer cells, which express endogenous IGFBP-3. Similar inductions of caspase activity was obtained for both prostate and non-small cell lung cancer cells.

Such increases in caspase-3 and -8 activities are consistent with the above-described canonical caspase/apoptosis model involving ligation of cell-surface "death" receptors, binding of adapter molecules, and recruitment of procaspases leading to proximity-induced activation.

Figure 17:
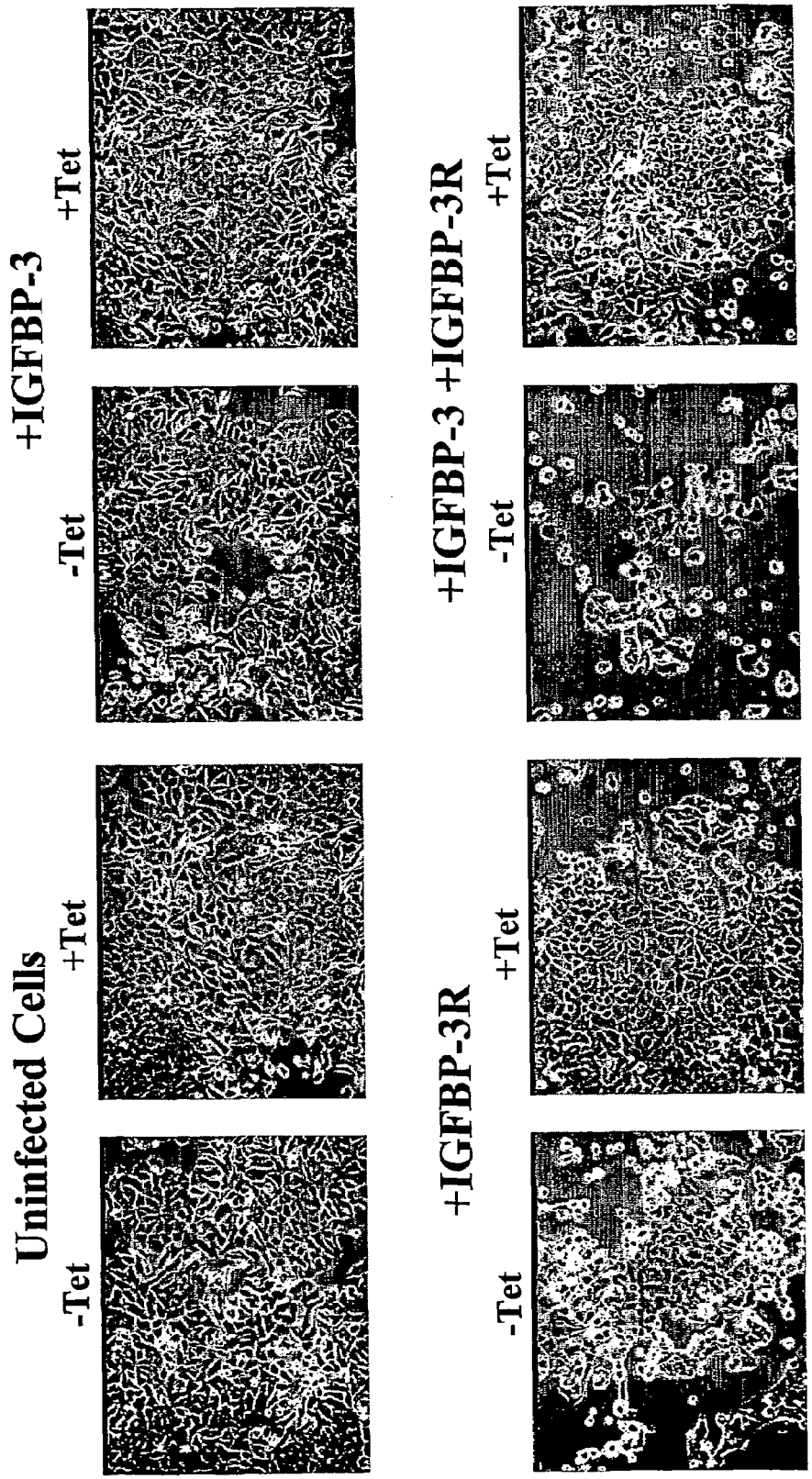
FIG. 17 shows that significant growth inhibition was observed in MCF-7 cancer cells when both IGFBP-3 and the IGFBP-3R were co-expressed, but not when only IGFBP-3R was expressed. Thus, IGFBP-3R-mediated growth inhibition requires IGFBP-3 interaction with the IGFBP-3R, futher demonstrating the IGFBP-3: IGFBP-3R specificity of the growth inhibition response.

The IGFBP-3: IGFBP-3R specificity of this caspase induction is supported by the finding that in MCF-7 human breast cancer cells, which do not express endogenous IGFBP-3, the effect of the IGFBP-3R on cell proliferation and activation of caspases was abrogated unless IGFBP-3 was co-expressed from an IGFBP-3 expression vector (FIG. 17). The upper left two panels of FIG. 17, marked "Uninfected," correspond to MCF-7 cell cultures without IGFBP-3 transfection and with the IGFBP-3R infection in the absence (−Tet) or presence (+Tet) of tetracycline. The upper right two panelsn of FIG. 17, marked "+IGFBP-3," correspond to MCF-7 cell cultures with only IGFBP-3 transfection in the absence (−Tet) or presence (+Tet) of tetracycline. The lower left two panels, marked "+IGFBP-3R," correspond to MCF-7 cell cultures with the IGFBP-3R infection in the absence (−Tet) or presence (+Tet) of tetracycline. The lower right two panels, marked "+IGFBP-3+IGFBP-3R," correspond to MCF-7 cell cultures with IGFBP-3 transfection and the IGFBP-3R infection in the absence (−Tet) or presence (+Tet) of tetracycline.

The data show that significant growth inhibition was observed in MCF-7 cancer cells when both IGFBP-3 and the IGFBP-3R were co-expressed. Thus, IGFBP-3R-mediated growth inhibition requires IGFBP-3 interaction with the IGFBP-3R, demonstrating the IGFBP-3: IGFBP-3R specificity of the response.

Therefore, according to the present invention, Ad:IGFBP-3R-mediated IGFBP-3R (P4.33) over-expression resulted in: significant growth inhibition of human breast cancer cells (Hs578t, MDA231 and IGFBP-3 expressing MCF-7), prostate cancer cells (PC-3) and non-small cell lung carcinoma cells; induction of apoptosis, as demonstrated by time-dependent increases of DNA fragmentation, and by significant increases of at least caspase-3 and -8 activities in human breast cancer cells, as well as in prostate and lung cancer cells.

Figure 18:
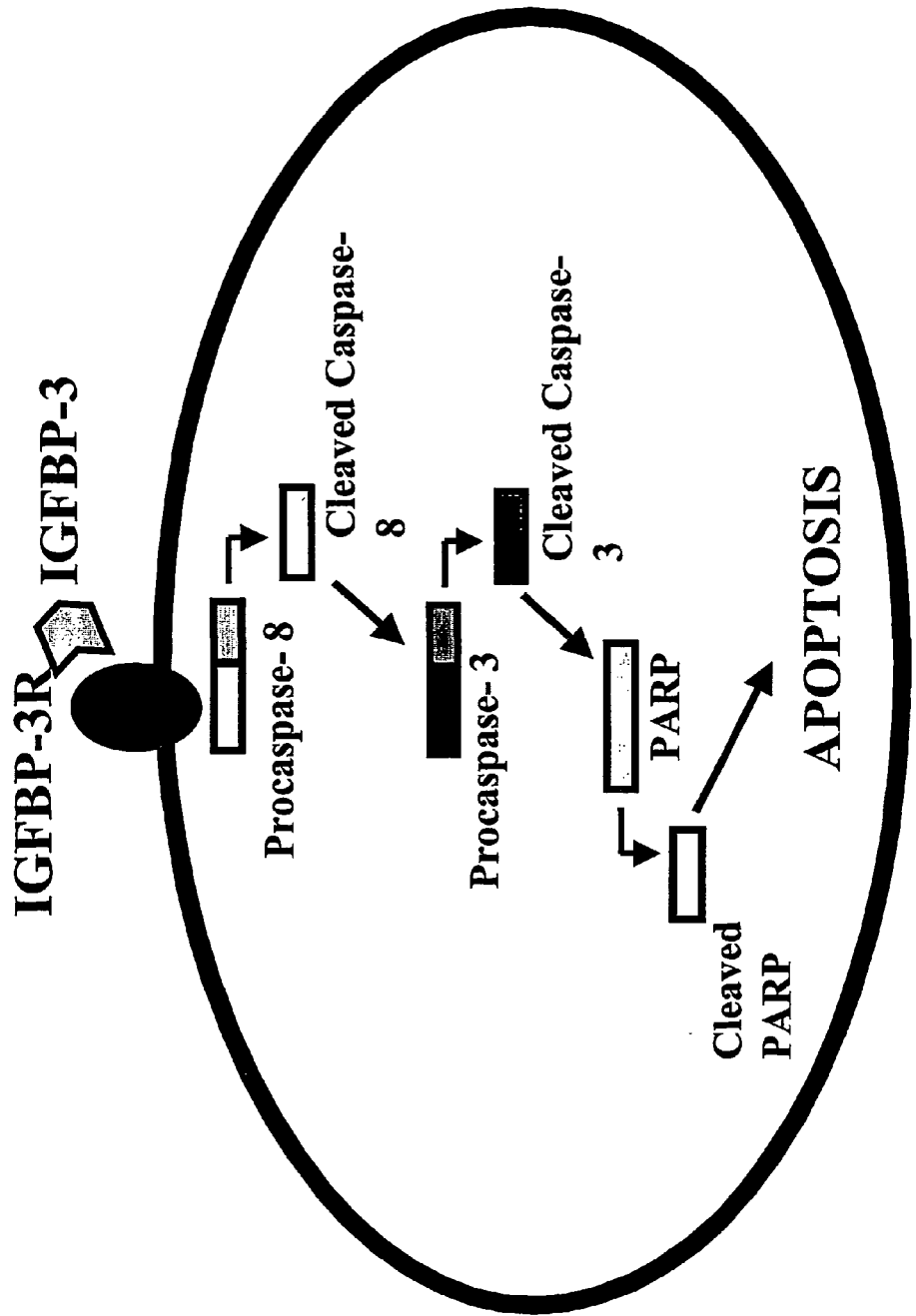
FIG. 18 shows a schematic representation of a model of the induction of apoptosis that is supported by embodiments of the present invention. According to the model P4.33 (IGFBP-3R) is a mediator of procaspase-8 activation, which in participates in procaspase-3 activation leading to the eventual cleavage of "TARP" which is implicated in the triggering of apoptosis.

Without being bound by theory, the present invention supports a mechanism whereby IGFBP-3R, among other things, functions as a novel class of mammalian cell death receptor (FIG. 18). FIG. 18 shows a schematic representation of a model of the induction of apoptosis that is supported by embodiments of the present invention. According to the model P4.33 (IGFBP-3R) is a mediator of procaspase-8 activation, which in participates in procaspase-3 activation leading to the eventual cleavage of "PARP" which is implicated in the triggering of apoptosis.

However, regardless of the precise apoptotic mechanism, IGFBP-3R (P4.33) is a novel and important cancer therapeutic target, and is part of a an expanded IGF axis (along with IGFBP-3 and potential adapter molecules) for the investigation of regulatory mechanisms involved in cancer cell proliferation, and the inhibition thereof.

In Summary

A novel P4.33 cDNA was isolated from an Hs578T human breast cancer cell cDNA library based on the ability of P4.33 to interact with IGFBP-3 in the yeast two-hybrid cloning system. The P4.33:IGFBP-3 interaction was further confirmed in a mammalian cell system by co-immunoprecipitation. The complete P4.33 cDNA, confirmed by 5'-RACE analysis, is 915 bp in length, and corresponds to a 915 nucleotide mRNA widely expressed in human tissues and cell lines. The novel P4.33 cRNA encodes a novel leucine-rich (19%) protein of 240 amino acids with a predicted molecular weight of 26 kDa, and having several potential glycosylation sites, a cAMP-dependent phosphorylation site, a single leucine zipper motif (LZ) and a transmembrane domain (TM) near the C-terminus.

Transient overexpression of IGFBP-3 P4.33 in breast cancer and insect cells resulted in enhanced specific binding to the cell surface, indicating that IGFBP-3 interacts with P4.33 on the cell surface. A polyclonal antibody was generated against the P4.33 protein, and this antibody was shown to be effective for specific immunoblotting, immunoprecipitation and immunocytochemistry. This antibody was used for western immunoblot analysis of fractionated cell lysates, and for immuncytochemical detection of P4.33 on adherent and suspended breast cancer cells. These studies showed that endogenous and transiently transfected P4.33 is located on the cell plasma membrane as well as in cytoplasmic/perinuclear intracellular locations. Furthermore, treatment of P4.33 transfected cells with exogenous OregonGreen-labeled IGFBP-3 resulted in IGFBP-3-dependent co-translocation of both P4.33 and IGFBP-3 into the nucleus.

These data show that the P4.33 protein is a functional cellular receptor for IGFBP-3, and that P4.33:IGFBP-3 complexes are translocated to the cell nucleus.

Transient overexpression of P4.33 in breast cancer cells that express IGFBP-3, resulted in a significant increase in cell detachment and/or death over time, compared to little or no effect in cells that do not produce IGFBP-3. Furthermore, transient overexpression of P4.33 in MCF-7 breast cancer cells resulted in a significant enhancement of the IGFBP-3-induced inhibition of DNA synthesis, as determined by measurement of [$^3$H]-thymidine incorporation into DNA.

Flow cytometric analysis of the cell cycle profile in Hs578T cells (expressing IGFBP-3), transiently transfected with P4.33, showed an increase in the percentage of sub-$G_1$ cells. Additionally, these cells displayed increased binding of Annexin V, an indicator of cells undergoing apoptosis. Western immunoblot analysis of lysates from these cells revealed a specific decrease in the level of Cyclin D.

Ad:IGFBP-3R-mediated IGFBP-3R (P4.33) over-expression resulted in: significant growth inhibition of human breast cancer cells (Hs578t, MDA231 and IGFBP-3 expressing MCF-7), prostate cancer cells (PC-3) and non-small cell lung carcinoma cells; induction of apoptosis, as demonstrated by time-dependent increases of DNA fragmentation, and by significant increases of at least caspase-3 and -8 activities in human breast cancer cells, as well as in prostate and lung cancer cells.

These data show that the P4.33:IGFBP-3 interaction is an important mechanism in IGFBP-3-mediated cell cycle arrest, apoptosis and growth inhibition in human cancer.

Without being bound by theory, IGFBP-3R likely represents a new class of mammalian cell death receptor. Regardless of mechanism, IGFBP-3R (P4.33) is a novel and important cancer therapeutic target, and is part of a an expanded IGF axis (along with IGFBP-3 and potential adapter molecules) for the investigation of regulatory mechanisms involved in cancer cell proliferation, and the inhibition thereof (FIG. 18).

Collectively, the disclosure, embodiments and Examples of the present invention show that P4.33 is a functional receptor for IGFBP-3 (i.e, "IGFBP-3R"), and that the interaction of IGFBP-3 with P4.33 is an important mechanism in the IGF-independent, growth inhibitory and apoptotic actions of IGFBP-3.

Accordingly, the present invention provides drug candidate screening assays, and diagnostic and therapeutic methods for the treatment of cancer and tumor suppression, utilizing a novel IGFBP-3 interacting protein called P4.33 (IGFBP-3R) as the intervention target. The present invention further provides a P4.33 cDNA sequence, a P4.33 polypeptide and fragments thereof, and an anti-P4.33 antibody.

We claim:

1. A method for treating cancer in a mammal, comprising:
   directly injecting a recombinant vector comprising a polynucleotide encoding a functional insulin-like growth factor binding protein-3 receptor (IGFBP-3R) into a tumor of a mammal such that the IGFBP-3R is expressed and tumor growth is inhibited,
   wherein the tumor is selected from the group consisting of breast, cervical, lung, non-small cell lung, colon and prostate tumors.

2. The method of claim 1, wherein the expression induces cellular apoptosis.

3. The method of claim 2, wherein the recombinant vector is an adeno or an adeno-associated virus (rAAV) vector.

4. The method of claim 2, wherein the cancer cells are prostate cancer cells.

5. The method of claim 2, wherein the recombinant vector is an adeno-associated virus (rAAV) vector, and wherein the cells are that of a prostate cancer.

6. The method of claim 2, further comprising administration of IGFBP-3, wherein said administering comprises direct introduction or injection of a recombinant IGFBP-3 expression vector into tumor tissue to afford vector-mediated expression of a therapeutically effective amount of IGFBP-3 in one or more cells of the tumor.

7. The method of claim 6, wherein the recombinant vector is an adeno-associated virus (rAAV) vector.

8. The method of claim 1, wherein the cancer is prostate cancer.

9. The method of claim 1, wherein the recombinant vector is a recombinant adeno or recombinant adeno-associated virus (rAAV) vector.

10. The method of claim 1, wherein the recombinant virus is a recombinant adeno-associated virus (rAAV) vector, and wherein said vector is administered by direct injection into a prostate tumor.

11. The method of claim 1, further comprising administration of IGFBP-3, wherein said administering comprises direct introduction or injection of a recombinant IGFBP-3 expression vector into tumor tissue to afford vector-mediated expression of a therapeutically effective amount of IGFBP-3 in one or more cells of the tumor.

12. The method of claim 11, wherein the recombinant IGFBP-3 expression vector is an adeno-associated virus (rAAV) vector, and wherein the cell is that of a prostate cancer.

\* \* \* \* \*

UNITED STATES PATENT AND TRADEMARK OFFICE
CERTIFICATE OF CORRECTION

PATENT NO. : 7,585,497 B2
APPLICATION NO. : 10/276491
DATED : September 8, 2009
INVENTOR(S) : Oh et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 476 days.

Signed and Sealed this

Fourteenth Day of September, 2010

David J. Kappos
*Director of the United States Patent and Trademark Office*